United States Patent
Klechevsky

(10) Patent No.: US 11,369,663 B2
(45) Date of Patent: Jun. 28, 2022

(54) DETECTION OF CD5 AND METHODS AND COMPOSITIONS FOR MODULATING CD5

(71) Applicant: Eynav Klechevsky, St. Louis, MO (US)

(72) Inventor: Eynav Klechevsky, St. Louis, MO (US)

(73) Assignee: Washington University, St. Louis, MO (US)

( * ) Notice: Subject to any disclaimer, the term of this patent is extended or adjusted under 35 U.S.C. 154(b) by 135 days.

(21) Appl. No.: 16/308,002

(22) PCT Filed: Jun. 7, 2017

(86) PCT No.: PCT/US2017/036377
§ 371 (c)(1),
(2) Date: Dec. 7, 2018

(87) PCT Pub. No.: WO2017/214285
PCT Pub. Date: Dec. 14, 2017

(65) Prior Publication Data
US 2019/0216897 A1    Jul. 18, 2019

Related U.S. Application Data

(60) Provisional application No. 62/346,851, filed on Jun. 7, 2016.

(51) Int. Cl.
| | |
|---|---|
| *A61K 38/20* | (2006.01) |
| *A61K 38/19* | (2006.01) |
| *A61K 45/06* | (2006.01) |
| *G01N 33/569* | (2006.01) |
| *A61P 37/02* | (2006.01) |
| *G01N 33/50* | (2006.01) |
| *A61K 38/21* | (2006.01) |
| *A61P 17/06* | (2006.01) |
| *A61P 35/00* | (2006.01) |
| *A61K 35/15* | (2015.01) |
| *A61K 39/395* | (2006.01) |
| *C12N 5/0784* | (2010.01) |

(52) U.S. Cl.
CPC .......... *A61K 38/2026* (2013.01); *A61K 35/15* (2013.01); *A61K 38/19* (2013.01); *A61K 38/191* (2013.01); *A61K 38/193* (2013.01); *A61K 38/20* (2013.01); *A61K 38/212* (2013.01); *A61K 38/217* (2013.01); *A61K 39/3955* (2013.01); *A61K 45/06* (2013.01); *A61P 17/06* (2018.01); *A61P 35/00* (2018.01); *A61P 37/02* (2018.01); *C12N 5/0639* (2013.01); *G01N 33/50* (2013.01); *G01N 33/56977* (2013.01); *C12N 2506/11* (2013.01)

(58) Field of Classification Search
CPC ..... A61K 38/20; A61K 38/2026; A61K 38/19
See application file for complete search history.

(56) References Cited

U.S. PATENT DOCUMENTS

| | | | |
|---|---|---|---|
| 5,849,589 A * | 12/1998 | Tedder | C12N 5/0639 435/377 |
| 7,341,870 B2 | 3/2008 | Plumas et al. | |
| 2009/0017076 A1 | 1/2009 | Miller et al. | |
| 2011/0250203 A1* | 10/2011 | Klitgaard | C07K 16/2896 424/136.1 |
| 2012/0121598 A1 | 5/2012 | Boumsell et al. | |

OTHER PUBLICATIONS

Kidaka et al. IL-4 down-regulates the surface expression of CD5 on B cells and inhibits spontaneous immunoglobulin and IgM-rheumatoid factor production in patients with rheumatoid arthritis. Clinical Experimental Immunology, 1992; 89:223-229 (Year: 1992).*
Fenutria et al. Transgenic Expression of Soluble Human CD5 Enhances Experimentally-Induced Autoimmune and Anti-Tumoral Immune Responses. PLoS ONE, 2014; 9(1): e84895. doi: 10.1371/journal.pone.0084895 (Year: 2014).*
Bowie et al. Deciphering the Message in Protein Sequences: Tolerance to Amino Acid Substitutions. Science, 1990, 247:1306-1310 (Year: 1990).*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138, 1990 (Year: 1990).*
Lazar et al. Transforming Growth Factor alpha: Mutation of Aspartic Acid 47 and Leucine 48 Results in Different Biological Activities. Mol. Cell. Biol., 8:1247-1252, 1988 (Year: 1988).*
Bork. Powers and Pitfalls in Sequence Analysis: The 70% Hurdle. Genome Research, 2000, 10:398-400 (Year: 2000).*
Vajdos et al. Comprehensive Functional Maps of the Antigenbinding Site of an Anti-ErbB2 Antibody Obtained with Shotgun Scanning Mutagenesis. J Mol Biol. Jul. 5, 2002;320(2):415-28 (Year: 2002).*
Brown et al. Tolerance to Single, but Not Multiple, Amino Acid Replacements in Antibody VH CDR2. J Immunol. May 1996; 156(9):3285-91 (Year: 1996).*
Guido et al. Virtual Screening and Its Integration with Modern Drug Design Technologies. Curr Med Chem. 2008; 15(1):37-46 (Year: 2008).*
Clark et al. Discovery and Development of Janus Kinase (JAK) Inhibitors for Inflammatory Diseases. J. Med. Chem., 2014, 57 (12), pp. 5023-5038 (Year: 2014).*
Aagaard et al. RNAi therapeutics: Principles, prospects and challenges. Advanced Drug Delivery Reviews 59 (2007) 75-86 (Year: 2007).*

(Continued)

*Primary Examiner* — Vanessa L. Ford
*Assistant Examiner* — Sandra Dillahunt

(57) ABSTRACT

The present disclosure provides for methods and compositions for the modulation of CD5 in a subject. Also provided are methods of detecting and monitoring diseases, such as inflammatory and autoimmune diseases.

7 Claims, 37 Drawing Sheets

Specification includes a Sequence Listing.

(56) References Cited

OTHER PUBLICATIONS

Warzocha et al. Antisense Strategy: Biological Utility and Prospects in the Treatment of Hematological Malignancies. Leukemia and Lymphoma, 1997; 24(3-4): 267-281 (Year: 1997).*
Consuegra-Fernández et al. CD5 as a Target for Immune-Based Therapies. Critical Reviews Immunology, 2015; 35(2): 85-115 (Year: 2015).*
Defrance et al. Human interleukin 4 down-regulates the surface expression of CD5 on normal and leukemic B cells. Eur. J. Immunol. 1989, 19:293-299 (Year: 1989).*
Hidaka et al. IL-4 down-regulates the surface expression of CD5 on B cells and inhibits spontaneous immunoglobulin and IgM-rheumatoid factor production in patients with rheumatoid arthritis. Clin. Exp. Immnunol., 1992; 89:223-229 (Year: 1992).*
Zhang et al. Induction of Dendritic Cell Differentiation by Granulocyte-Macrophage Colony-Stimulating Factor, Stem Cell Factor, and Tumor Necrosis Factor a In Vitro From Lineage Phenotypes-Negative c-kit+ Murine Hematopoietic Progenitor Cells. Blood, vol. 90, No. 12 (Dec. 15), 1997: pp. 4842-4853 (Year: 1997).*
Artyomov, M.N. et al. Modular expression analysis reveals functional conservation between human Langerhans cells and mouse cross-priming dendritic cells. *J Exp Med* 2015 212:743-757.
Banchereau, J. and Steinamn, R.M. Dendritic cells and the control of immunity. *Nature* 1998. 392:245-252.
Banchereau, J. et al. The differential production of cytokines by human Langerhans cells and dermal CD14(+) DCs controls CTL priming. *Blood* 2012. 119:5742-5749.
Banchereau, J. et al. Immune and clinical outcomes in patients with stage IV melanoma vaccinated with peptide-pulsed dendritic cells derived from CD34+ progenitors and activated with type I interferon. *J Immunother* 2005. 28:505-516.
Banchereau, J. et al. Immunoglobulin-like transcript receptors on human dermal CD14+ dendritic cells act as a CD8-antagonist to control cytotoxic T cell priming. *Proc Natl Acad Sci USA* 2012. 109:18885-18890.
Breton, G. et al. Defining human dendritic cell progenitors by multiparametric flow cytometry. *Nature protocols* 2015. 10:1407-1422.
Breton, G et al. Circulating precursors of human CD1c+ and CD141+ dendritic cells. *J Exp Med* 2015. 212:401-413.
Brown, M.H. and Lacey, E. A ligand for CD5 is CD5. *J Immunol* 2010.185:6068-6074.
Caux, C. et al. CD34+ hematopoietic progenitors from human cord blood differentiate along two independent dendritic cell pathways in response to granulocyte-macrophage colony-stimulating factor plus tumor necrosis factor alpha: II. Functional analysis. *Blood* 1997. 90:1458-1470.
Caux, C. et al. CD34+ hematopoietic progenitors from human cord blood differentiate along two independent dendritic cell pathways in response to GM-CSF+TNF alpha. *J Exp Med* 1996.184:695-706.
Chamian, F. et al. Alefacept reduces infiltrating T cells, activated dendritic cells, and inflammatory genes in psoriasis vulgaris. *Proc Natl Acad Sci USA* 2005.102:2075-2080.
Cheung, K.L. et al. Psoriatic T cells recognize neolipid antigens generated by mast cell phospholipase delivered by exosomes and presented by CD1a. *J Exp Med* 2016. 213:2399-2412.
Chu, C.C. et al. Resident CD141 (BDCA3)+ dendritic cells in human skin produce IL-10 and induce regulatory T cells that suppress skin inflammation. *J Exp Med* 2012. 209:935-945.
Collin, M. et al. S. Human dendritic cell deficiency: the missing ID? *Nat Rev Immunol* 2011. 11:575-583.
De Jong, A. et al. CD1a-autoreactive T cells are a normal component of the human alphabeta T cell repertoire. *Nat Immunol* 2010. 11:1102-1109.
De Wit, J. et al. CD5 costimulation induces stable Th17 development by promoting IL-23R expression and sustained STAT3 activation. *Blood* 2011.118:6107-6114.
Doulatov, S. et al. Revised map of the human progenitor hierarchy shows the origin of macrophages and dendritic cells in early lymphoid development. *Nat Immunol* 2010.11:585-593.

Flutter, B. et al. TLRs to cytokines: mechanistic insights from the imiquimod mouse model of psoriasis. *Eur J Immunol* 2013. 43:3138-3146.
Fujita, H. et al. Human Langerhans cells induce distinct IL-22-producing CD4+T cells lacking IL-17 production. *Proc Natl Acad Sci USA* 2009.106:21795-21800.
Gaublomme, J.T. et al. Single-Cell Genomics Unveils Critical Regulators of Th17 Cell Pathogenicity. *Cell* 2015.163:1400-1412.
Gimferrer, I. et al. The accessory molecules CD5 and CD6 associate on the membrane of lymphoid T cells. *J Biol Chem* 2003. 278:8564-8571.
Hope, J.L. et al. 1st International Conference on Human &Translational Immunology. *Nat Immunol* 2016.18:1-4.
International Search Report and Written Opinion dated Oct. 18, 2017 in corresponding International Application PCT/US2017/036377, filed Jun. 7, 2017,18 pages.
Klechevsky, E. Human dendritic cells—stars in the skin. *Eur J Immunol* 2013. 43:3147-3155.
Klechevsky, E. Functional Diversity of Human Dendritic Cells. *Adv Exp Med Biol Chapter* 4 2015. 850:43-54.
Klechevsky, E. et al. Functional specializations of human epidermal Langerhans cells and CD14+ dermal dendritic cells. *Immunity* 2008. 29:497-510.
Laouar, Y. et al. STAT3 is required for Flt3L-dependent dendritic cell differentiation. *Immunity* (2003) 19:903-912.
Lee, J. et al. Restricted dendritic cell and monocyte progenitors in human cord blood and bone marrow. *J Exp Med* 2015. 212:385-399.
Lenz, A. et al. Human and murine dermis contain dendritic cells. Isolation by means of a novel method and phenotypical and functional characterization. *J Clin Invest* 1993. 92:2587-2596.
Lewis, K.L. et al. Notch2 receptor signaling controls functional differentiation of dendritic cells in the spleen and intestine. *Immunity* 2011. 35:780-791.
Lowes, M.A. et al. Increase in TNF-alpha and inducible nitric oxide synthase-expressing dendritic cells in psoriasis and reduction with efalizumab (anti-CD11a). *Proc Natl Acad Sci USA* 2005.102:19057-19062.
Lowes, M.A. et al. Psoriasis vulgaris lesions contain discrete populations of Th1 and Th17 T cells. *The Journal of investigative dermatology* 2008.128:1207-1211.
Mathers, A.R. et al. Differential capability of human cutaneous dendritic cell subsets to initiate Th17 responses. *J Immunol* 2009. 182:921-933.
Mayer, C.T. et al. Selective and efficient generation of functional Batf3-dependent CD103+ dendritic cells from mouse bone marrow. *Blood* 2014.124:3081-3091.
Melillo, J.A. et al. Dendritic cell (DC)-specific targeting reveals Stat3 as a negative regulator of DC function. *J Immunol* 2010. 184:2638-2645.
Milner, J.D. et al. Early-onset lymphoproliferation and autoimmunity caused by germline STAT3 gain-of-function mutations. *Blood* 2015.125:591-599.
Nefedova, Y. et al. Activation of dendritic cells via inhibition of Jak2/STAT3 signaling. *J Immunol* 2005. 175:4338-4346.
Nestle, F.O. et al. Plasmacytoid predendritic cells initiate psoriasis through interferonalpha production. *J Exp Med* 2005. 202:135-143.
Nestle, F.O. et al. Characterization of dermal dendritic cells obtained from normal human skin reveals phenotypic and functionally distinctive subsets. *J Immunol* 1993. 151:6535-6545.
Okamura, H. et al. Cloning of a new cytokine that induces IFN-gamma production by T cells. *Nature* 1995. 378:88-91.
Penel-Sotirakis, K. et al. Differential capacity of human skin dendritic cells to polarize CD4+ T cells into IL-17, IL-21 and IL-22 producing cells. *PLoS One* 2012. 7:e45680.
Romani, N. et al. Proliferating dendritic cell progenitors in human blood. *J Exp Med* 1994.180:83-93.
Sabat, R. et al. Therapeutic opportunities of the IL-22-IL-22R1 system. *Drug discovery Nature reviews*. 2014.13:21-38.
Seneschal, J. et al. Human epidermal Langerhans cells maintain immune homeostasis in skin by activating skin resident regulatory T cells. *Immunity* 2012. 36:873-884.

(56) References Cited

OTHER PUBLICATIONS

Tortola, L. et al. Psoriasiform dermatitis is driven by IL-36-mediated DC-keratinocyte crosstalk. *J Clin Invest* 2012.122:3965-3976.

Vera, J. et al. The CD5 ectodomain interacts with conserved fungal cell wall components and protects from zymosan-induced septic shock-like syndrome. *Proc Natl Acad Sci USA* 2009.106:1506-1511.

Wang, C. et al. CD5L/AIM Regulates Lipid Biosynthesis and Restrains Th17 Cell Pathogenicity. *Cell* 2015. 163:1413-1427.

Wang, P. et al. The STAT3-binding long noncoding RNA lnc-DC controls human dendritic cell differentiation. *Science* 2014. 344:310-313.

Wohn, C. et al. Langerin(neg) conventional dendritic cells produce IL-23 to drive psoriatic plaque formation in mice. *Proc Natl Acad Sci USA* 2013.110:10723-10728.

Zaba, L.C. et al. Psoriasis is characterized by accumulation of immunostimulatory and Th1/Th17 cell-polarizing myeloid dendritic cells. *The Journal of investigative dermatology* 2009.129:79-88.

Zhang, C. et al. CD5 Binds to Interleukin-6 and Induces a Feed-Forward Loop with the Transcription Factor STAT3 in B Cells to Promote Cancer. *Immunity* 2016. 44:913-923.

\* cited by examiner

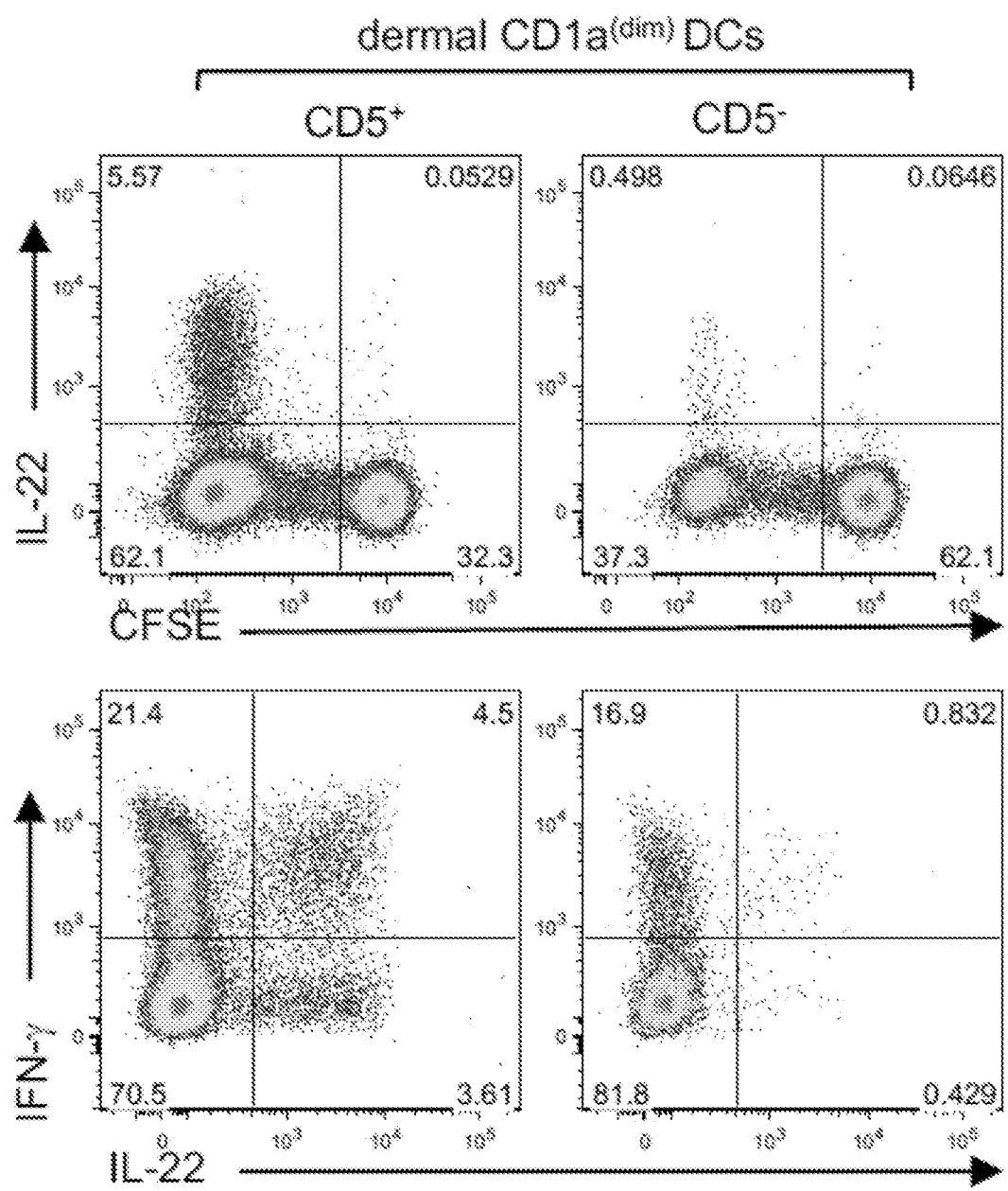

FLT3-L DCs

CD103+ DCs

SEQUENCE LISTING

```
<160> NUMBER OF SEQ ID NOS: 28

<210> SEQ ID NO 1
<211> LENGTH: 24
<212> TYPE: DNA
<213> ORGANISM: Artificial Sequence
<220> FEATURE:
<223> OTHER INFORMATION: synthetic construct

<400> SEQUENCE: 1
ccatcagcag atcattctag acaa                                              24

<210> SEQ ID NO 2
<211> LENGTH: 22
<212> TYPE: DNA
<213> ORGANISM: Artificial Sequence
<220> FEATURE:
<223> OTHER INFORMATION: synthetic construct

<400> SEQUENCE: 2
cgccattatg attcagagac tg                                                22

<210> SEQ ID NO 3
<211> LENGTH: 21
```

```
<212> TYPE: DNA
<213> ORGANISM: Artificial Sequence
<220> FEATURE:
<223> OTHER INFORMATION: synthetic construct

<400> SEQUENCE: 3
agcaacttca cacctcccta c                                              21

<210> SEQ ID NO 4
<211> LENGTH: 21
<212> TYPE: DNA
<213> ORGANISM: Artificial Sequence
<220> FEATURE:
<223> OTHER INFORMATION: synthetic construct

<400> SEQUENCE: 4
actgctgact agaactcagg c                                              21

<210> SEQ ID NO 5
<211> LENGTH: 20
<212> TYPE: DNA
<213> ORGANISM: Artificial Sequence
<220> FEATURE:
<223> OTHER INFORMATION: synthetic construct

<400> SEQUENCE: 5
actggcaaaa ggatggtgac                                                20

<210> SEQ ID NO 6
<211> LENGTH: 20
<212> TYPE: DNA
<213> ORGANISM: Artificial Sequence
<220> FEATURE:
<223> OTHER INFORMATION: synthetic construct

<400> SEQUENCE: 6
gacctgtggg ttgttgacct                                                20

<210> SEQ ID NO 7
<211> LENGTH: 20
<212> TYPE: DNA
<213> ORGANISM: Artificial Sequence
<220> FEATURE:
<223> OTHER INFORMATION: synthetic construct

<400> SEQUENCE: 7
cattctgcaa tgacctccac                                                20

<210> SEQ ID NO 8
<211> LENGTH: 19
<212> TYPE: DNA
<213> ORGANISM: Artificial Sequence
<220> FEATURE:
<223> OTHER INFORMATION: synthetic construct

<400> SEQUENCE: 8
tcaggggaaa ttcctgcac                                                 19

<210> SEQ ID NO 9
<211> LENGTH: 23
<212> TYPE: DNA
<213> ORGANISM: Artificial Sequence
<220> FEATURE:
<223> OTHER INFORMATION: synthetic construct

<400> SEQUENCE: 9
```

```
gactacctca accgttccac gtc                                            23
```

<210> SEQ ID NO 10
<211> LENGTH: 21
<212> TYPE: DNA
<213> ORGANISM: Artificial Sequence
<220> FEATURE:
<223> OTHER INFORMATION: synthetic construct

<400> SEQUENCE: 10

```
tctatcaggg tcttcattgc g                                              21
```

<210> SEQ ID NO 11
<211> LENGTH: 25
<212> TYPE: DNA
<213> ORGANISM: Artificial Sequence
<220> FEATURE:
<223> OTHER INFORMATION: synthetic construct

<400> SEQUENCE: 11

```
cccaggaaga catacttaga agaaa                                          25
```

<210> SEQ ID NO 12
<211> LENGTH: 23
<212> TYPE: DNA
<213> ORGANISM: Artificial Sequence
<220> FEATURE:
<223> OTHER INFORMATION: synthetic construct

<400> SEQUENCE: 12

```
caacagtagc aaagacttga cca                                            23
```

<210> SEQ ID NO 13
<211> LENGTH: 20
<212> TYPE: DNA
<213> ORGANISM: Artificial Sequence
<220> FEATURE:
<223> OTHER INFORMATION: synthetic construct

<400> SEQUENCE: 13

```
tttcctgacc aaactcagca                                                20
```

<210> SEQ ID NO 14
<211> LENGTH: 20
<212> TYPE: DNA
<213> ORGANISM: Artificial Sequence
<220> FEATURE:
<223> OTHER INFORMATION: synthetic construct

<400> SEQUENCE: 14

```
ctggatgttc tggtcgtcac                                                20
```

<210> SEQ ID NO 15
<211> LENGTH: 20
<212> TYPE: DNA
<213> ORGANISM: Artificial Sequence
<220> FEATURE:
<223> OTHER INFORMATION: synthetic construct

<400> SEQUENCE: 15

```
tgcgatggtg ataaaagtgg                                                20
```

<210> SEQ ID NO 16
<211> LENGTH: 20
<212> TYPE: DNA
<213> ORGANISM: Artificial Sequence

```
<220> FEATURE:
<223> OTHER INFORMATION: synthetic construct

<400> SEQUENCE: 16
ggccagaagc tctgctactc                                                    20

<210> SEQ ID NO 17
<211> LENGTH: 20
<212> TYPE: DNA
<213> ORGANISM: Artificial Sequence
<220> FEATURE:
<223> OTHER INFORMATION: synthetic construct

<400> SEQUENCE: 17
caccctgagc aagaaggaat                                                    20

<210> SEQ ID NO 18
<211> LENGTH: 23
<212> TYPE: DNA
<213> ORGANISM: Artificial Sequence
<220> FEATURE:
<223> OTHER INFORMATION: synthetic construct

<400> SEQUENCE: 18
tgtcatttat gagggcttca ttt                                                23

<210> SEQ ID NO 19
<211> LENGTH: 25
<212> TYPE: DNA
<213> ORGANISM: Artificial Sequence
<220> FEATURE:
<223> OTHER INFORMATION: synthetic construct

<400> SEQUENCE: 19
caaccaacaa gtgatattct ccatg                                              25

<210> SEQ ID NO 20
<211> LENGTH: 21
<212> TYPE: DNA
<213> ORGANISM: Artificial Sequence
<220> FEATURE:
<223> OTHER INFORMATION: synthetic construct

<400> SEQUENCE: 20
gatccacact ctccagctgc a                                                  21

<210> SEQ ID NO 21
<211> LENGTH: 22
<212> TYPE: DNA
<213> ORGANISM: Artificial Sequence
<220> FEATURE:
<223> OTHER INFORMATION: synthetic construct

<400> SEQUENCE: 21
ttgctcgaga tgtcatgaag ga                                                 22

<210> SEQ ID NO 22
<211> LENGTH: 25
<212> TYPE: DNA
<213> ORGANISM: Artificial Sequence
<220> FEATURE:
<223> OTHER INFORMATION: synthetic construct

<400> SEQUENCE: 22
agcaggtcag caaagaactt atagc                                              25
```

```
<210> SEQ ID NO 23
<211> LENGTH: 29
<212> TYPE: DNA
<213> ORGANISM: Artificial Sequence
<220> FEATURE:
<223> OTHER INFORMATION: synthetic construct

<400> SEQUENCE: 23
gcctagaggt atggctgtaa ctatctctg                                    29

<210> SEQ ID NO 24
<211> LENGTH: 26
<212> TYPE: DNA
<213> ORGANISM: Artificial Sequence
<220> FEATURE:
<223> OTHER INFORMATION: synthetic construct

<400> SEQUENCE: 24
catgtcctgg gacacttctc tgaaag                                       26

<210> SEQ ID NO 25
<211> LENGTH: 17
<212> TYPE: DNA
<213> ORGANISM: Artificial Sequence
<220> FEATURE:
<223> OTHER INFORMATION: synthetic construct

<400> SEQUENCE: 25
aggcaccagg gcgtgat                                                 17

<210> SEQ ID NO 26
<211> LENGTH: 23
<212> TYPE: DNA
<213> ORGANISM: Artificial Sequence
<220> FEATURE:
<223> OTHER INFORMATION: synthetic construct

<400> SEQUENCE: 26
gcccacatag gaatccttct gac                                          23

<210> SEQ ID NO 27
<211> LENGTH: 18
<212> TYPE: DNA
<213> ORGANISM: Artificial Sequence
<220> FEATURE:
<223> OTHER INFORMATION: synthetic construct

<400> SEQUENCE: 27
atggtgaagg tcggtgtg                                                18

<210> SEQ ID NO 28
<211> LENGTH: 18
<212> TYPE: DNA
<213> ORGANISM: Artificial Sequence
<220> FEATURE:
<223> OTHER INFORMATION: synthetic construct

<400> SEQUENCE: 28
cattctcggc cttgactg                                                18
```

DETECTION OF CD5 AND METHODS AND COMPOSITIONS FOR MODULATING CD5

CROSS-REFERENCE TO RELATED APPLICATIONS

This application claims the benefit of priority to PCT International Application No. PCT/US2017/036377 filed 7 Jun. 2017, which claims the benefit of U.S. Provisional Application Ser. No. 62/346,851 filed on 7 Jun. 2016, each of which is incorporated herein by reference in its entirety.

STATEMENT REGARDING FEDERALLY SPONSORED RESEARCH OR DEVELOPMENT

Not applicable.

MATERIAL INCORPORATED-BY-REFERENCE

The Sequence Listing, which is a part of the present disclosure, includes a computer readable form comprising nucleotide and/or amino acid sequences of the present invention. The subject matter of the Sequence Listing is incorporated herein by reference in its entirety.

FIELD OF THE INVENTION

The present disclosure generally relates to methods of treatment, methods of diagnosis and monitoring CD5 associated diseases, disorders, and conditions (e.g., inflammatory disease, autoimmune disease, malignant disease). Also provided herein are methods and compositions for the modulation of CD5 in a subject.

BACKGROUND OF THE INVENTION

Dendritic cells (DCs) comprise a heterogeneous group of antigen-presenting cells (APCs) found throughout the body that include plasmacytoid DCs (pDCs) and CD11c myeloid conventional DCs (mDCs or cDCs) (Banchereau and Steinman, 1998). DC subsets display different cell surface markers that afford each specific DC population different functions (Klechevsky, 2015). Consequently, normal immunity and tolerance is dependent on a balance between the DC subsets. In human skin, cDCs include epidermal Langerhans cells (LCs), dermal CD1a$^{(dim)}$CD141$^-$, dermal CD1a$^{(dim)}$CD141$^+$ and dermal CD14$^+$ subsets, which all have distinct functional properties (Klechevsky, 2013; Klechevsky, 2015; Lenz et al., 1993). The dermal CD14$^+$ DCs promote humoral immunity by directly priming B-cells (Caux et al., 1997; Caux et al., 1996; Klechevsky et al., 2008) and by priming the activation of CD4$^+$ T follicular helper cells to induce isotype switching and plasma cell generation. Dermal CD14$^+$ DCs also actively inhibit the cellular immune response by promoting T regulatory responses, or type 2 cytokine-producing CD8$^+$ T cells (Banchereau et al., 2012a; Banchereau et al., 2012b; Chu et al., 2012). In contrast, LCs enhance cellular immunity by inducing Th2 differentiation of naïve CD4$^+$ T cells and via priming and cross-priming of naïve CD8$^+$ T cells (Banchereau et al., 2012a; Klechevsky et al., 2008; Seneschal et al., 2012). Recently, human LCs were also shown to be responsible for directing IL-17 and IL-22-mediated responses (de Jong et al., 2010; Fujita et al., 2009; Mathers et al., 2009; Penel-Sotirakis et al., 2012), two responses indicative of inflammatory autoimmune skin diseases like psoriasis.

DCs are implicated in the loss of tolerance that occurs in psoriasis, a skin inflammatory disease. This is suggested by their increased numbers in psoriatic lesions and their role in inducing T cells to produce Th1 (IFN-$\gamma$, TNF-$\alpha$) and Th17 (IL-17, IL-22) responses (Lowes et al., 2008; Zaba et al., 2009). It is believed that the efficacy of current psoriasis therapies, such as biologic immunotherapy, psoralen or ultraviolet A (PUVA) is due to the reduction of DC numbers (Chamian et al., 2005) or their cytokine production (Lowes et al., 2005). It was shown that in the initial phase of psoriasis, the antimicrobial peptide LL37 (cathelicidin) binds DNA and activates plasmacytoid DCs (pDCs) to produce IFN-$\alpha$ (Nestle et al., 2005). Despite this progress, the role of specific cDC subsets in psoriasis is still unsettled. Previously, it has been described that inflammatory DCs in psoriasis include a subset of cells with reduced expression of CD1c and a subset of DCs that produce TNF-$\alpha$ and iNOS (Lowes et al., 2005). However, a detailed phenotype of the key DC that contributes to the priming of the inflammatory T cell response via Th1, Th17, or Th22 is still unknown (Sabat et al., 2014).

SUMMARY OF THE INVENTION

Among the various aspects of the present disclosure is the provision of compositions and methods for modulating CD5.

An aspect of the present disclosure includes methods of detecting CD5$^+$ cells (e.g., dendritic cells) in a biological sample. In some embodiments, the method includes obtaining a biological sample from a subject or detecting a CD5$^+$ cell. In some embodiments, the CD5$^+$ cell is a CD5$^+$ dendritic cell or the subject is diagnosed with or is suspected of having an inflammatory disease or an autoimmune disease. In some embodiments, the biological sample comprises a skin sample; the biological sample comprises a tissue sample, whole blood, plasma, serum, cord blood, or bone marrow; or increased CD5 expression on the cell obtained from the subject compared to a control or healthy cell indicates an increase of disease severity or disease progression. In some embodiments, the biological sample comprises a skin sample obtained from a skin biopsy from the dermis, the epidermis, or combinations thereof. In some embodiments, the method includes isolating a dendritic cell by cell sorting; detecting a CD5$^+$ cell by immunostaining or contacting the cell with a CD5 antibody; or administering a CD5 modulating agent to the subject. In some embodiments, the method includes diagnosing the subject with an inflammatory or autoimmune disease if the CD5$^+$ cells or CD5 expression on the cells are elevated compared to a control sample; or monitoring the inflammatory or autoimmune disease progression, wherein an increase in CD5 indicates an increase in disease progression or severity and a decrease in CD5 indicated a decrease in disease progression or severity. In some embodiments, the inflammatory disease or an autoimmune disease comprises psoriasis or an immune-mediated disease dependent on IFN-$\gamma$ and IL-22.

Another aspect of the present disclosure includes methods of modulating CD5 in a subject. In some embodiments, the method includes administering a CD5 modulation agent to a subject; administering CD5 modulation agent to cells obtained from a subject; administering a CD5 modulation agent to progenitor cells obtained from a subject; or genome editing cells obtained from a subject, wherein the genome editing reduces CD5 signals and results in increased or decreased expression of CD5. In some embodiments, modulating CD5$^+$ cells in a subject comprises modulating expression of CD5+ in cells with a CD5 modulating agent; modulating CD5 expressing cells; or inhibiting differentiation of progenitor cells into CD5 expressing cells. In some embodiments, the CD5 modulation agent reduces CD5 expression or reduces cells expressing CD5; the CD5 modulation agent inhibits or induces (differentiation of progenitor cells into CD5 expressing DC or LC cells; the modulation agent inhibits CD5; the CD5 modulating agent increases CD5+ DC numbers; reducing CD5 expression results in reduced Th1, Th22, and CTL responses; reducing expression of CD5 on cells or reduction in CD5+ cells for use in treatment of psoriasis, autoimmune, or an inflammatory skin disease; increasing CD5 expression on cells or increasing CD5+ cells for use in the treatment of cancer, an infectious disease, a mycobacteria related diseases, a pathogen that contains beta-glucans, a bacterial infection, a viral infection, or a fungal infection; increasing CD5 expression results in enhanced Th1, Th22, and CTL responses; increasing CD5+ or expanding CD5+ DCs results in immune system activation; the CD5 modulation agent comprises IL-4, wherein IL-4 blocks monocyte cell differentiation; the CD5 modulation agent comprises FLT3L, TNF-α, LTα/β, increasing differentiation of the CD5+ cells; or increasing CD5 induces T cell response or induces cytotoxic T-cells and Th22 cells. In some embodiments, the CD5 modulation agent modulates CD8+ T cell or CD4+ response; induces CD4+ T cell differentiation into Th1 and Th22 cells; or inhibits CD4+ T cell differentiation into Th1 and Th22 cells, wherein inducing comprises over-expression or activation of CD5 and results in enhanced CTL response. In some embodiments, the CD5 modulation agent comprises FLT3-L, SCF, GM-CSF, TNF-α, or LTα/β. In some embodiments, the CD5 modulation agent comprises FLT3-L and SCF; FLT3-L, GM-CSF, and SCF; TNF-α, FLT3-L, GM-CSF, and SCF; or LTα/β, FLT3-L, GM-CSF, and SCF. In some embodiments, the CD5 modulating agent comprises one or more agents selected from the group consisting of a CD5 inhibitor, a CD5 blocking agent, a CD5 inducing agent, or a CD5 activating agent. In some embodiments, the CD5 inhibitor comprises IL-4 or a monoclonal antibody to CD5; or the CD5 inducing agent comprises FLT3-L, GM-CSF, TNF-α, or LTα/β. In some embodiments, the method comprises administering a STAT3 inhibitor; administering a STAT3 activator; administering an IL-18 blocking agent; administering zymosan; administering PD-1, PDL1, or CTLA-4; administering TNF-α, TNF-β, IL-34, IL-6, LTα/β, GM-CSF, SCF, FLT3-L, IL-22, IL-12p70, IL-18, IL-17, IL-4, IFN-α, IFN-γ, IL-18, IL-12p35, IL-23p19, IL-1β, IL-17A, IL-17F, or TGF-β; administering IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, or IL-36; or administering a blocking agent thereof. In some embodiments, the subject has an inflammatory disease, cancer, psoriasis, an inflammatory skin disease, an infectious disease, a mycobacteria related diseases, a pathogen that contains beta-glucans, a microbial infection, a mycobacterial infection, a bacterial infection, a viral infection, or a fungal infection; an autoimmune disease selected from the group consisting of alopecia areata; autoimmune hemolytic anemia; autoimmune hepatitis; dermatomyositis; diabetes (type 1); some forms of juvenile idiopathic arthritis; glomerulonephritis; Graves' disease; Guillain-Barré syndrome; idiopathic thrombocytopenic purpura; myasthenia gravis; lichen sclerosus; dermatomyositis, lupus erythematosus some forms of myocarditis; multiple sclerosis; pemphigus/pemphigoid; pernicious anemia; polyarteritis nodosa; polymyositis; primary biliary cirrhosis; psoriasis; rheumatoid arthritis; scabies, scleroderma/systemic sclerosis; Sjögren's syndrome; systemic lupus erythematosus; some forms of thyroiditis; some forms of uveitis; vitiligo; granulomatosis with polyangiitis (Wegener's); graft versus host disease; Crohn's disease; and colitis; or atopic dermatitis; stasis dermatitis; allergic/irritant contact dermatitis; seborrheic dermatitis; lichen planus; urticarial; papular uritcaria; drug eruptions; bullous diseases; mastocytosis; eosinophilic folliculitis; or pruritic popular eruption of HIV.

Another aspect of the present disclosure includes methods of treating an inflammatory or autoimmune disease, disorder, or condition or cancer. In some embodiments, the method includes inhibiting CD5 expression or CD5+ cells with a CD5 modulation agent, wherein the CD5 modulation agent reduces pathogenesis of an inflammatory or an autoimmune disease, disorder, or condition by reducing Th1 and Th22 and CTL responses. In some embodiments, the inflammatory disease is psoriasis. In some embodiments, the CD5 modulation agent is IL-4. In some embodiments, the method includes administering an IL-18 neutralizing agent, optionally a neutralizing IL-18 mAb or a STAT3 activator.

Another aspect of the present disclosure includes methods of expanding CD5+ dendritic cells. In some embodiments, the method comprises isolating a biological sample obtained from a subject comprising progenitor cells or inducing differentiation of the progenitor cells by activating the progenitor cells with a CD5 modulation agent, wherein cytotoxic T lymphocytes (CTLs) are induced. In some embodiments, the biological sample comprises a blood sample, a biopsy sample, or a tumor sample or the CD5 modulation agent comprises FLT3-L, GMCSF, TNF-α, or LTα/β. In some embodiments, the method comprises administering the activated progenitor cell to the subject, wherein CTL response is enhanced. In some embodiments, the activated progenitor cells are administered to a target or tumor site. In some embodiments, the method includes inactivating STAT3, optionally with a STAT3 inhibitor, STAT3 siRNA, or a STAT3 small molecule inhibitor. In some embodiments, inactivating STAT3 comprises administration of a STAT3 inhibitor, STAT3 siRNA, or a STAT3 small molecule inhibitor.

Another aspect of the present disclosure includes methods of differentiating progenitor cells into CD5+ cells. In some embodiments, the method includes obtaining a progenitor cell from a subject or administering a CD5 modulation agent to the progenitor cell. In some embodiments, the CD5 modulation agent comprises FLT3-L and SCF; FLT3-L, GM-CSF, and SCF; TNF-α, FLT3-L, GM-CSF, and SCF; or LTα/β, FLT3-L, GM-CSF, and SCF. In some embodiments, the progenitor cell comprises CD34$^-$CD123$^{(hi)}$CD117$^{(dim)}$ and the progenitor cells are differentiated into CD11c+CD1c+CD5+ DCs.

Another aspect of the present disclosure includes compositions comprising a CD5 modulation agent. In some embodiments, the composition comprises FLT3-L and SCF; FLT3-L, GM-CSF, and SCF; TNF-α, FLT3-L, GM-CSF, and SCF; LTα/β, FLT3-L, GM-CSF, and SCF; TNF-α and LTα/β; or IL-4. In some embodiments, the composition induces differentiation of progenitor cells into CD5+ cells.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

(FIG. 1A) Upper: expression of CD1a and CD14 on purified skin DCs defines epidermal CD1a$^+$ LCs, dermal CD1a$^{(dim)}$ DCs, and dermal CD14$^+$ DCs subpopulations. Lower: expression of CD5 defines new subpopulations of CD1a$^{(hi)}$Langerin$^+$ LCs and dermal CD1a$^{(dim)}$CD141$^-$ DCs. (FIG. 1B) Relative representation of each human DC subset in normal skin (n=33). Percentage of individual DC subsets mean±SD±SEM out of the total migrating DCs (HLA-DR$^+$CD3/19/56$^-$) cells are plotted. Epidermal CD5$^+$ LCs: 6.0±6.15±1.05; CD5$^-$ LCs: 26.9±20.4±3.4; dermal CD1a$^{(dim)}$ DCs: CD5$^+$: 15.8±12.6±2.16; CD5$^-$: 37.6±18.9±3.2; CD141$^+$: 1.9±2±0.3; dermal CD14$^+$ DCs: 10.2±7.6±1.3. (FIG. 1C) Morphology of sorted skin CD5$^+$ LCs, CD5$^-$LCs, dermal CD1a$^{(dim)}$CD5$^+$, CD1a$^{(dim)}$CD5$^-$, CD1a$^{(dim)}$CD141$^+$, and CD14$^+$ DCs visualized by GIEMSA staining of cytospin preparations. Images were acquired using a Leica 63x/1.40 oil objective on a Leica DMIRB microscope with a Leica DFC310 FX camera. Scale bars represent 10 μm. (FIG. 1D) HLA-DR$^+$CD11c$^+$CD14$^-$CD1c$^+$ CD5$^+$ and CD5$^-$ DCs from skin epidermis, dermis, blood and in vitro-differentiated cultures were analyzed for the expression of Langerin, BDCA-2, CD11c, HLA-DR, CD141, CD11b, CD83, CD86, PD-L1, CD40, CD123, CD135, CD115, CCR7, CD103, CLA, CXC3CR1, CD1a and Sirp-α. Plot shows GeoMean intensity with values of the background staining subtracted. The mean values obtained for two to four donors were plotted. (FIG. 1E) Dermal CD1 a$^{(dim)}$ CD5$^+$ and CD5$^-$ DCs were sorted and stimulated with either a TLR agonist (Pam2, Zymosan, Poly I:C, LPS), T cell signal (T cells, CD40L) or inflammatory/DC differentiating cytokines (GM-CSF+ FLT3-L, GM-CSF+IFN-α, GM-CSF+IL-4, IFN-γ) for six days. Plot shows Geo-Mean expression of CD5 on the cells after six days of stimulation. The mean values obtained for three donors was plotted.

(FIG. 2A) Proliferation of allogeneic naive CD8$^+$ T cells primed with sorted CD40L-activated skin dermal CD5$^+$ or CD5$^-$ CD1a$^{(dim)}$ DCs, dermal CD1a$^{(dim)}$CD141$^+$ or dermal CD14$^+$ DCs was measured after seven days by CFSE-dilution using flow cytometry. Graph shows the percentage of proliferating (CFSE$^{(low)}$) CD3$^+$CD8$^+$ T cells (n=15). (FIG. 2B) Graph shows the percentage of proliferating (CFSE$^{(low)}$) CD3$^+$ CD8$^+$ T cells by different numbers of dermal DC subsets. 0.1, 0.25, 1, 3 and 7×10$^3$ DCs were cultured with 1×10$^5$ allogeneic naïve T cells. One representative experiment out of three is shown. (FIG. 2C) Allogeneic CFSE-labeled naïve CD8$^+$ T cells primed for seven days by each dermal skin mDC subset were stained and analyzed by flow cytometry for the expression of granzyme B. The percentage of cells that diluted CFSE and expressed granzyme B is shown. One out of eight experiments is shown. (FIG. 2D) Plot shows the percentage of cells that primed by each of the mDC subsets and expressed granzyme B (n=8). (FIG. 2E) Plots show the expression of IFN-γ and TNF-α by naïve CD8$^+$ T cells that were primed by either dermal CD5$^+$ or CD5$^-$ DCs. CD8$^+$ T cells primed by the dermal CD14$^+$ DCs are shown as a control. One out of five experiments is shown. (FIG. 2F) CFSE$^{(low)}$CD8$^+$ T cells that were primed by either dermal CD1a$^{(dim)}$CD5$^+$ or CD5$^-$ were reactivated by anti-CD3 and anti-CD28 mAbs for 18 hours. IFN-γ was measured in the culture supernatant by a Luminex magnetic bead assay. Graph shows pulled results of four experiments.

FIG. 3A-FIG. 3E is a series of plots and graphs showing dermal CD5$^+$ DCs are superior to dermal CD5$^-$ DCs at inducing the proliferation and differentiation of Th22 cells. (FIG. 3A) Proliferation of allogeneic naive CD4$^+$ T cells primed with sorted CD40L-activated dermal CD5$^+$ or CD5$^-$ CD1a$^{(dim)}$ DCs, dermal CD1a$^{(dim)}$CD141$^+$, or dermal CD14$^+$ DCs was measured after seven days by CFSE-dilution using flow cytometry. Graph shows the percentage of proliferating (CFSE$^{(low)}$) CD3$^+$CD4$^+$ T cells (n=10). (FIG. 3B) Proliferation of allogeneic naive CD4$^+$ T cells, primed with different numbers of sorted CD40L-activated dermal CD5$^+$ or CD5$^-$ CD1a$^{(dim)}$ DCs, or dermal CD14$^+$ DC (0.03, 0.1, 0.25, 1, 3 and 7×10$^3$ DCs), was measured after seven days by CFSE dilution using flow cytometry. Graph shows percentage of cells that diluted CFSE in response to different numbers of DCs. One representative experiment out of four is shown. (FIG. 3C) CFSE-labeled sorted naive CD4$^+$ T cells cultured for six days with CD40L-activated dermal CD1a$^{(dim)}$CD5$^+$ or CD1a$^{(dim)}$CD5$^-$ DCs. CFSE dilution and intracytoplasmic expression of IFN-γ and IL-22 was analyzed by flow cytometry after five hour stimulation with PMA and ionomycin. Upper panel: plots show the frequency CD4$^+$ T cells that diluted CFSE and express IL-22. lower panel: plots show the frequency of IFN-γ and IL-22-producing CFSE$^{(low)}$CD4$^+$ T cells. Data are representative of seven independent experiments. (FIG. 3D) Plot shows the frequency of IL-22-producing CD4$^+$ T cells that were primed by the different skin DC subsets in fourteen independent experiments. Values are normalized 100% was set to the highest value in each dataset. Dataset includes epidermal and dermal DC subsets (see also FIG. 4F). (FIG. 3E) CFSE$^{(low)}$ CD4$^+$ T cells, primed by either dermal CD1a$^{(dim)}$CD5$^+$ or CD5$^-$ DCs, were sorted and restimulated with anti-CD3 and anti-CD28 mAbs for 18 hours. IL-22 and IFN-γ were measured by a Luminex multiplex bead assay. One out of three experiments is shown.

(FIG. 4A) Normalized percentage of CFSE$^{(low)}$ allogeneic naïve CD8$^+$ T cells that were primed for six to eight days by sorted activated CD5$^+$, CD5$^-$ LCs, dermal CD5$^+$, CD5$^-$, CD141$^+$ CD1a$^{(dim)}$ DCs, or dermal CD14$^+$ DC. Results of ten independent experiments are shown. (FIG. 4B) Allogeneic CFSE-labeled naïve CD8$^+$ T cells primed for seven days by each LC subset were stained and analyzed by flow cytometry for the expression of granzyme B. The percentage of cells that diluted CFSE and expressed granzyme B is shown. One out of eight experiments is shown. (FIG. 4C) Plot shows the percentage of cells that primed by each of the mDC subsets and expressed granzyme B (n=8). (FIG. 4D) Plots show the expression of IFN-γ and TNF-α by naïve CD8$^+$ T cells that were primed by either CD5$^+$ or CD5$^-$ LCs. CD8$^+$ T cells primed by the dermal CD14$^+$ DCs are shown as a control. (FIG. 4E) Normalized percentage of CFSE$^{(low)}$ allogeneic naïve CD4$^+$ T cells that were primed for six to eight days by sorted activated CD5$^+$ or CD5$^-$ LCs, dermal CD5$^+$, CD5$^-$, CD141$^+$ CD1a$^{(dim)}$ DCs, or dermal CD14$^+$ DC. Results of >nine independent experiments are shown. (FIG. 4F) CFSE-labeled sorted naive CD4$^+$ T cells cultured for six days with TLR7/8 (CLO75) and CD40L-activated CD5$^+$ LCs or CD5$^-$ LCs. Intracytoplasmic expression of IFN-γ and IL-22 was analyzed by flow cytometry after five-hour stimulation with PMA and ionomycin. Plots show the frequency of IFN-γ and IL-22-producing CFSE$^{(low)}$CD4$^+$ T cells. (FIG. 4G) Plot shows the frequency of IL-22-producing CD4$^+$ T cells that were primed by the different LC subsets in fourteen independent experiments. Values are normalized 100% to the highest value.

(FIG. 5A) Expression of CD5 and CD14 on epidermal (left) and dermal (right) DCs from involved (left forearm) and uninvolved (left arm) lesions of psoriasis patient 025 (see TABLE 1). (FIG. 5B) Percentage of CD5$^+$ DCs in the epidermis (left) and dermis (right) of involved and uninvolved skin lesions of seven and eight patients, respectively. Percentage shown is of the total migrating DCs (HLA-DR$^+$CD3/19/56$^-$) cells. Mean±SEM: epidermal CD5$^+$ DCs: Involved: 35.7±4.7%; uninvolved: 23.4±4.6% Dermal CD5$^+$ DCs: Involved: 52.2±7.8%; uninvolved: 32.7±5.2%. Dashed lines marked the levels of CD5$^+$ DCs as measured in healthy skin. (FIG. 5C) Immunofluoresence staining of CD5 and CD1a on healthy skin and psoriasis uninvolved and involved skin lesions. The range of the epidermis thickness in the three tissues was measured as 68-92 μm in healthy skin and 102-180 μm in psoriatic uninvolved, and 595-868 μm in psoriatic involved skin lesions. (FIG. 5D) CD5 and CD1a expression in psoriasis, cutaneous lupus, Langerhans cell histiocytosis, and graft versus host diseased skin. Magnitude: upper panel 20×, lower panel 40×.

(FIG. 6A) Gating strategy for cord blood progenitors were sorted as Lin$^{neg}$(CD3$^-$CD19$^-$CD56$^-$CD14$^-$CD66b$^-$)DC$^{neg}$ (CD1c, BDCA2, CD141)$^-$CD10$^-$ (see also FIG. 12): CD34$^+$ CD117$^+$; CD34$^-$CD117$^+$ or CD34$^-$CD123$^+$. Histograms show the expression of CD5 on the different progenitor subsets CD34$^+$CD117$^+$CD123$^-$ (blue); CD34$^-$CD117$^{(dim)}$ CD123$^+$ (red); CD34$^-$ CD117$^+$CD123$^-$ (orange). Expression of CD5 on lineage-positive cells is shown as a control (grey). (FIG. 6B) Flow cytometry plots show DCs obtained from cultures of cord blood CD45$^+$Lin$^{neg}$(CD3$^-$CD19$^-$CD56$^-$CD14$^-$CD66b$^-$)DC$^{neg}$(CD1c, BDCA2, CD141) CD10$^-$ CD34$^+$CD117$^+$CD123$^-$ cells on MS-5 cells with FLT3-L$^+$SCF$^+$GM-CSF$^+$ and in the presence of TNF-α or LTα/β. Plots show the frequency of CD11c$^+$CD1a$^+$CD5$^+$ and CD11c$^+$CD1c$^+$CD5$^+$ DCs on day seven. Flow cytometry plots are gated on live, CD45$^+$HLA-DR$^+$CD11c$^+$ cells. (FIG. 6C) Similar to B, but CD34$^+$ progenitors were cultured in the absence of GM-CSF with SCF and FLT3-L. Graph shows the frequency of live HLA-DR CD1c$^+$CD5$^+$ and CD1a$^+$ CD5$^+$ DCs on day ten. Flow cytometry plots are gated on live, CD45$^+$HLA-DR$^+$ cells. (FIG. 6D) Graph shows the number of CD1c$^+$CD5$^+$ DCs out of live, CD45$^+$HLA-DR$^+$ CD11c$^+$ on day seven. Six independent experiments are shown. (FIG. 6E) CD34$^+$ DCs were differentiated in vitro for twelve days in the presence of GM-CSF, FLT3-L and SCF and with TNFα or LTα1/β2. CD1c$^+$CD5$^+$, CD1c$^+$CD5$^-$ or CD14$^+$ DCs were sorted and co-cultured with naïve T cells. Graph shows the number of CD8$^+$ T cells that diluted CFSE in response to different numbers of DCs from the different culture conditions. (FIG. 6F) DCs were differentiated from CD34$^-$CD117$^+$ for 12 days. The distinct CD1c$^+$CD5$^+$, CD1c$^+$CD5$^-$ or CD14$^+$ DC subsets were then sorted and co-cultured with naïve Allogeneic CFSE-labeled T cells for seven days (300 DCs: 1×10$^5$ T cells). CFSE$^{low}$ were then stained and analyzed by flow cytometry for the expression of granzyme B and perforin. One of three experiments is shown. (FIG. 6G) Like F, Plots show the expression of IFN-γ and TNF-α by naïve CD8$^+$ T cells that were primed by either CD5$^+$ or CD5$^-$ or CD14$^-$ in vitro DC subsets. One of three experiments is shown. (FIG. 6H) CD34$^+$ DCs were differentiated in vitro for twelve days in the presence of GM-CSF, FLT3-L and SCF and with TNFα or LTα1/β2. CD1c$^+$CD5$^+$, CD1c$^+$CD5$^-$ or CD14$^+$ DCs were sorted and co-cultured with naïve T cells. Graph shows the number of CD4$^+$ T cells that diluted CFSE in response to different numbers of DCs from the different culture conditions. (FIG. 6I) DCs were differentiated from CD34$^-$CD117$^+$ for 12 days. The distinct CD1c$^+$CD5$^+$, CD1c$^+$CD5$^-$ or CD14$^+$ DC subsets were then sorted and co-cultured with naïve T cells for seven days (300 DCs: 1×10$^5$ T cells). Plots show the fraction of CD4$^+$ T cells that diluted CFSE and produced IL-22 following six days of priming with the different DCs subsets. One of three experiments is shown. (FIG. 6J) CFSE$^{(low)}$CD4$^+$ T cells that were primed by either in vitro CD1c$^+$CD5$^+$, CD1c$^+$CD5$^-$ or CD14$^+$ DCs were reactivated by anti-CD3 and anti-CD28 mAbs for 18 hours. IL-22 was measured in the culture supernatant by a Luminex magnetic bead assay (n=6).

(FIG. 7A) Sorted cord blood CD34$^+$CD117$^+$, CD34$^-$CD117$^{dim}$CD123$^+$ or CD34$^-$CD117$^+$CD123$^-$ progenitors were cultured in the presence of FLT3-L$^+$SCF$^+$GM-CSF$^+$ and LTα1/β2. Flow cytometry plots, gated on live, CD45$^+$HLA-DR$^+$CD11c$^+$ cells, show culture output of CD1a$^+$CD5$^+$ DCs on day seven. Representative results of three independent experiments are shown. (FIG. 7B) CD34$^+$ CD117$^+$, CD34$^-$CD117$^+$CD123$^-$ or CD34$^-$ CD117$^{dim}$CD123$^+$ were isolated from human dermis, in a similar manner to cord blood progenitor isolation (FIG. 6A) and cultured in the presence of FLT3-L$^+$SCF$^+$GM-CSF$^+$. Flow cytometry plots are gated on live, CD45$^+$ cells and show the expression of HLA-DR$^+$ or Lineage (CD3/CD19/CD56)$^+$ cells that were differentiated from the different progenitors. (FIG. 7C) plots show the expression of CD1c and CD5 on HLA-DR+ cells that differentiated from CD34$^-$ CD117$^{dim}$CD123$^+$ for seven days in the presence of FLT3-L$^+$SCF$^+$GM-CSF$^+$ and with either TNF-α or LTα1/β2. Representative results of two independent experiments are shown.

(FIG. 8A) CD5 expression on DCs were derived from wild-type or CD5$^{-/-}$ BM cells (bone marrow cells) using FLT3-L. (FIG. 8B and FIG. 8C) DCs were stimulation with Poly I:C or Zymosan. Graph shows the expression of IL-6 (FIG. 8B) and TNF-α (FIG. 8C) and that were measured in the culture supernatant by either WT or CD5$^{-/-}$ DCs after 24 hours by flow cytometry using BD Cytometric Bead Array (CBA). (FIG. 8D) CD5 expression on CD103$^+$ DCs that were derived from WT or CD5$^{-/-}$ BM using GM-CSF and FLT3-L. (FIG. 8E) sorted DC cultures were stimulated with Poly I:C or Zymosan. Graph shows the levels of IL-12p70 production by the different DC types, as measured by flow cytometry using CBA.

(FIG. 9A) Ear-skin thickness of wild-type (B6/NCI) and CD5$^{-/-}$ mice treated daily for seven days with Imiquimod (+IMQ) or left untreated (n=3). (FIG. 9B) Ear-skin thickness of wild-type (B6/NCI) and CD5$^{-/-}$ mice treated daily for seven days with Imiquimod (+IMQ) or left untreated. Hematoxylin-and-eosin staining of ear skin from wild-type and CD5$^{-/-}$ mice treated for seven days. Scale bar is shown as 25 μm one of three experiments with three to five mice each. (FIG. 9C) Quantification of viable CD45$^+$ cells in suspensions of ear skin cells from wild-type and CD5$^{-/-}$ mice treated for seven days and control untreated ears. Each symbol represents an individual mouse; small horizontal lines indicate the mean (±SEM). (FIG. 9D) Quantification of CD11c$^+$CD5$^+$ DCs in suspensions of ear skin cells from wild-type that were untreated or treated with Imiquimod for seven days. Each symbol represents an individual experiment (n=3) with three to five mice per group; small horizontal lines indicate the mean (±SEM). (FIG. 9E) Representative plots of CD11b and CD5 expression on the CD11c$^+$ DCs that were purified from a mouse ears that were treated with Imiquimod or left untreated. One of three representative experiments. (FIG. 9F) RT-PCR analysis of mRNA in ear skin from wild-type and CD5$^{-/-}$ mice treated with Imiquimod for seven days or control untreated mice. Each symbol represents an individual mouse; small horizontal lines indicate the mean (±SEM). Data are pooled results of two experiments with three to five mice per group (FIG. 9G) Left panel: Expression of CD5 on CD11b$^-$ DCs that were sorted from skin of wild type or CD5 mice treated for seven days. Right panel: Cytokines were measured in the culture supernatants of CD11b$^-$ DCs obtained from wild-type and CD5$^{-/-}$ mice skin and activated overnight with zymosan. *P≤0.05 and **P≤0.01. Data are representative of four experiments with three to five mice.

(FIG. 10A) Plots show CD5 and CD1c expression on the surface of Left: skin LCs (population 1), dermal CD1a(dim) DCs (population 2), FIG. 10B: cord blood and adults peripheral blood CD11c+CD1c+ DCs and CD11c+CD141+ DCs. One out of more than three independent donors is shown. (FIG. 10C) Plots show CD5 and CD6 expression on the surface of skin LCs (population 1), dermal CD1a(dim) DCs (population 2), dermal CD14$^+$ DCs (population 3) and on resident T cells.

(FIG. 14A) The plot shows fold change mRNA expression of IL-18 in sorted epidermal or dermal CD5$^+$ and CD5$^-$ DCs as assessed by qPCR, epidermal (n=3) dermal (n=4). The expression in CD5$^+$ DCs was normalized to that of the CD5$^-$ DC within the same skin compartment. (FIG. 14B) Confocal microscopy analysis of IL-18 expression by epidermal and dermal CD1a$^+$CD5$^+$ DCs in a steady state or upon IFN-α and CD40L activation. (FIG. 14C) Naïve allogeneic T cells were labeled with CFSE and primed for seven days with CD40L-activated CD5$^+$ LCs and a neutralizing IL-18 mAb or an isotype-matched control. Dot plots show the proportion of cells that diluted CFSE (CFSE$^{(low)}$) as assessed by flow cytometry. Data shown is one of five independent experiments. (FIG. 14D) Graph shows the proportions of IFN-γ-producing CD8$^+$ T cells that were primed by allogeneic CD40L-activated CD5$^+$ DCs (from epidermis and dermis) in the presence of neutralizing mAb to IL-18 or an isotype-matched control, N=5 P<0.05.

(FIG. 17A) DCs were differentiated from monocytes using GMCSF and with either IL-4, TNF-α, LTα/β or IL-34. The frequency of CD5$^+$ DCs was measured on day 6. (FIG. 17B) DCs were differentiated from monocytes using GMCSF (black) or MCSF (grey) and with either IL-6 or IL-4. The fluorescence intensity of CD5 was measured on the DCs on day 6.

DETAILED DESCRIPTION OF THE INVENTION

The present disclosure is based, at least in part, on the discovery that CD5$^+$ DCs are highly potent inducers of T cell responses.

As described herein, CD5 itself is important for the cell's ability to secrete proinflammatory cytokines. As such, DCs can also be used as a biomarker as their numbers is increased with disease severity (see e.g., Example 1). In particular, it has been shown herein that examination of healthy human epidermal and dermal skin cells revealed a novel CD5-expressing DC subtype. The CD5$^+$ DCs are shown to be potent inducers of cytotoxic T cells and Th22 cells, a hallmark response in psoriasis. Remarkably, it is shown herein that CD5$^+$ DCs were significantly enriched in inflamed psoriatic skin compared to distal tissue, suggesting their involvement in the disease.

Furthermore, it has been discovered that a unique progenitor population found in human cord blood and in the dermal skin layer marked as CD34$^-$ CD123$^{(hi)}$CD117$^{(dim)}$ was an immediate precursor of this unprecedented CD11c$^+$CD1c$^+$CD5$^+$ DCs.

As described herein, it has been shown that using DCs from CD5 knockout (KO) or WT mice, CD5 expression on DCs is important for their ability to secrete proinflammatory cytokines following activation. In an experimental mouse model of psoriasis-like disease, CD11c$^+$CD5$^+$ DCs expanded markedly in inflamed skin and CD5 KO mice were protected from psoriasis-like skin changes, identifying a role for CD5-dependent immune activation in this inflammatory condition (see e.g., Example 1).

Furthermore, the present disclosure shows CD5$^+$ DCs also expresses IL-18 which contributes to their ability to prime cytolytic T cell responses (see e.g., Example 3). A critical cell required to induce cancer immunity and fight infections (e.g., microbial infection), IL-18, has also been shown to be highly expressed in inflamed psoriasis skin (where there are an increased amount of CD5$^+$ DCs).

Figure 13A:
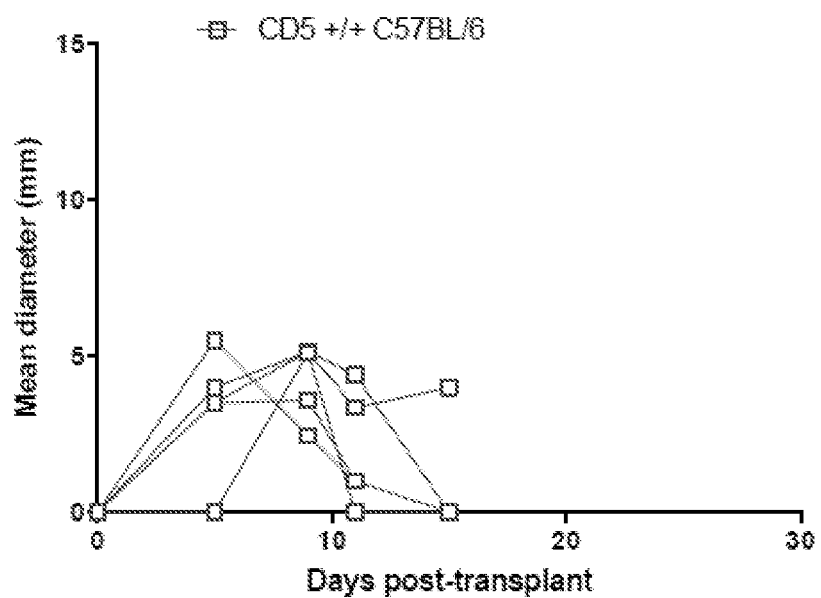
FIG. 13A-FIG. 13C is a series of graphs showing the tumor growth data from the CD5 knockout mice injected with 1969. 1969 is a regressor tumor derived from a female C57BL6 Rag2$^{-/-}$ mouse. 5 female B6 CD5 KO mice (FIG. 13B); 5 female B6 WT mice (FIG. 13A). 3 male 129S6 Rag2$^{-/-}$ mice compared to the WT and KO mice (FIG. 13C).
Figure 13B:
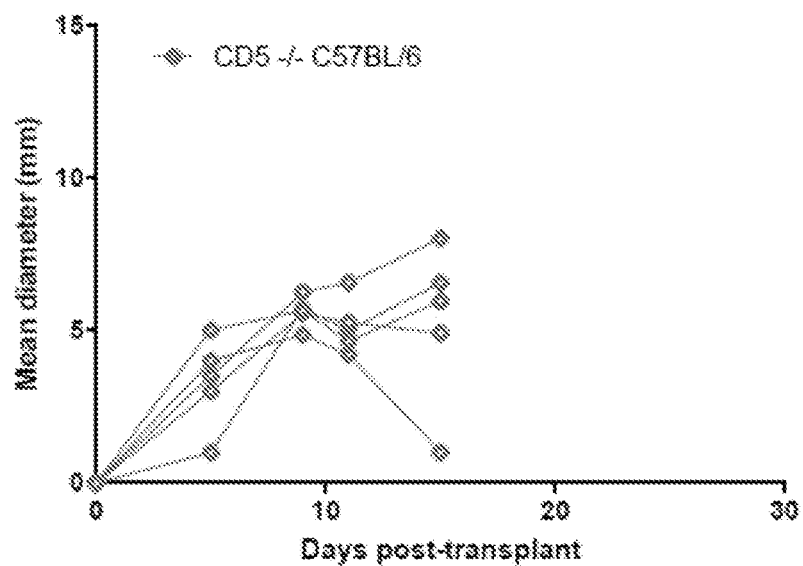
Figure 13C:
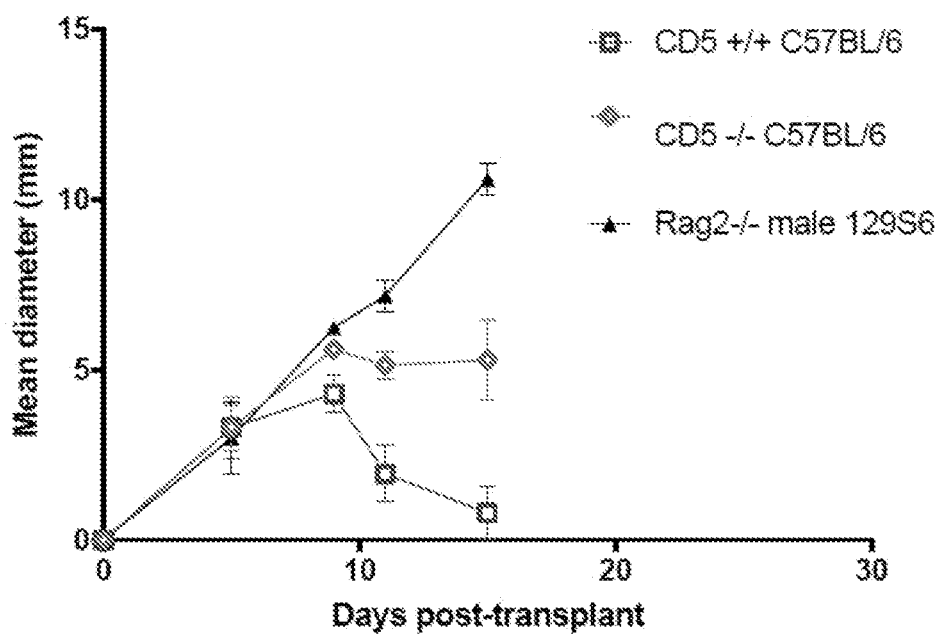

As also described herein, CD5 deficient mice (see e.g., FIG. 13) did not reject a tumor (see e.g., Example 2). As such, it is presently believed that CD5 is critical for tumor rejection and enhancing CD5+ DC differentiation (elaborated in the Example 1) can provide another tool for cancer therapies.

As described herein, because dendritic cells don't respond to beta-glucans (Zymosan) if the DCs lack CD5 (see e.g., Example 1, FIG. 8), the methods as described herein can be translated to not only psoriasis and other inflammatory skin diseases, but also infectious diseases such as mycobacteria related diseases and other pathogens that contain beta-glucans, such as fungus. Furthermore, the present disclosure demonstrates that CD5+ DCs are associated with inflammation (e.g., inflammatory skin disease, psoriasis), autoimmune disease, bacterial, fungal, and viral infection (patients with activating STAT3 mutations—implicated in dysfunction in T-cell generation in autoimmune disease and viral infection—showed reduced numbers of the CD5+ DCs). As such, the present disclosure demonstrates that modulating the cytokine milieu in the skin or activating STAT3 can be a treatment for inflammatory skin diseases (e.g., psoriasis). In contrast, reducing STAT3 expression or blocking STAT3 can be a suitable treatment for diseases such as cancer.

In addition it was discovered that cell supernatant from inflamed psoriatic skin promote the differentiation of the CD5+ DCs.

The methods and compositions as described herein can be used for treatments of autoimmune disease, inflammatory disease, and cancer. The methods and compositions as described herein can be used for autologous vaccine strategies.

Langerhans Cells (LCs)

Langerhans cells (LCs) (aka epidermal DCs) are dendritic cells that reside in the epidermis that play a central role in T-lymphocyte mediated skin immunity. Upon activation with antigenic stimuli, they differentiate drastically into mature dendritic cells while migrating from the epidermis to regional lymph nodes, where they prime T cell responses. As described herein, a novel subset of LCs was discovered to express CD5, ie., CD5+ LCs Dendritic Cells (DCs)

Dendritic cells (DCs) are important in regulating immunity and tolerance and consist of functionally distinct subsets. Examination of healthy human epidermal and dermal skin cells revealed a novel CD5-expressing DC subtype. The CD5+ DCs were potent inducers of cytotoxic T cells and Th22 cells a hallmark response in psoriasis. Remarkably, CD5+ DCs were significantly enriched in inflamed psoriatic skin compared to distal tissue, suggesting their involvement in the disease. A unique progenitor population found in human cord blood and in the dermal skin layer marked as CD34−CD123$^{(hi)}$CD117$^{(dim)}$ was an immediate precursor of this unprecedented CD11c+CD1c+CD5+ DCs. Using DCs from CD5 knockout (KO) or WT mice, it is shown herein that CD5 expression on DCs is important for their ability to secrete proinflammatory cytokines following activation. In an experimental mouse model of psoriasis-like disease, CD11c+CD5+ DCs expanded markedly in inflamed skin and CD5 KO mice were protected from psoriasis-like skin changes, identifying a role for CD5-dependent immune activation in this inflammatory condition.

DCs are also important for tumor rejection by mediating the priming of tumor specific cytotoxic T cells. Mice lacking DCs, are not able to reject tumors. In addition, some DCs are more proficient at mediating cytotoxic CD8+ T cells.

Figure 16:
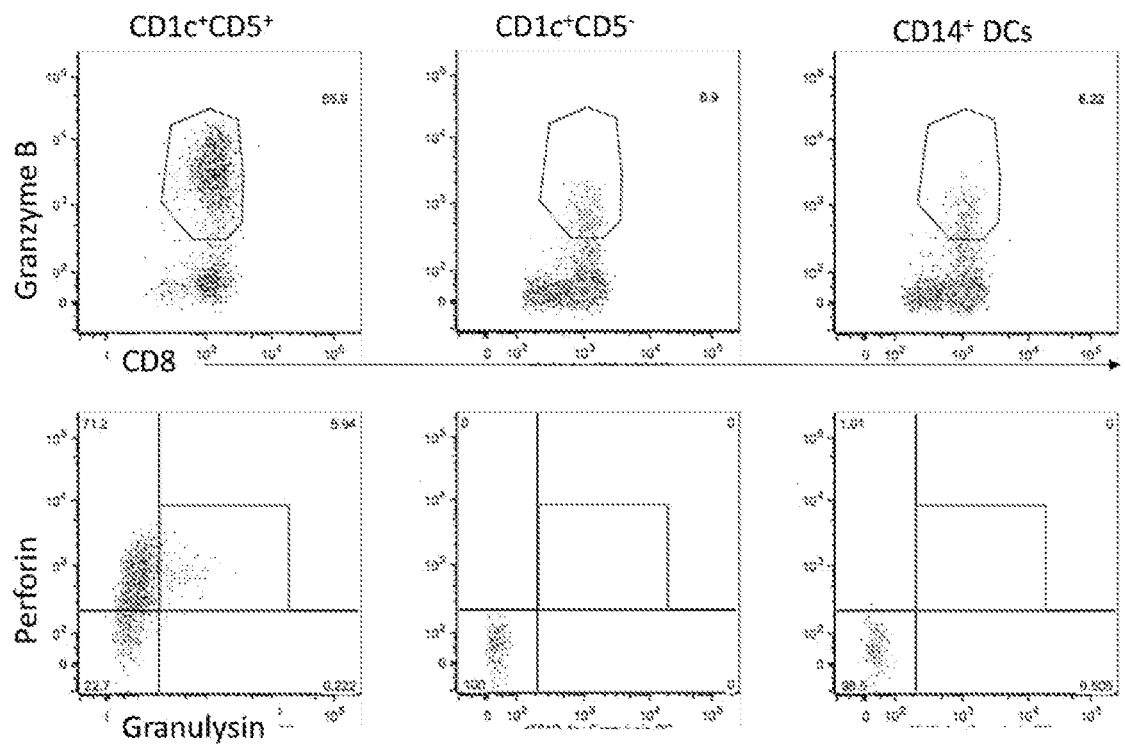
FIG. 16 is a series of plots showing CD5$^+$ DCs are able to prime polycytotoxic T cells that express granzyme B perforin and granulysin more efficiently than the CD5$^-$ DCs or CD14$^+$ DCs.

Likewise, bacterial infections requires the induction of Th1 (IFN-γ, TNF-α) and Th17 (IL-17, IL-22) responses as well as the induction of multifunctional CD8+ T cells expressing Granzyme B and perforin and granulysin (see e.g., FIG. 16.

CD5 Modulation Agents

As described herein, CD5 expression has been implicated in various diseases, disorders, and conditions. As such, modulation of CD5 (e.g., modulation of CD5 or CD5+ DCs) can be used for treatment of such conditions. A CD5 modulation agent can modulate CD8+ T cell or CD4+ response or induce or inhibit CD4+ T cell differentiation into Th1 and Th22 cells. CD5 modulation can comprise modulating the expression of CD5 on cells, modulating the quantity of cells that express CD5, or modulating the quality of the CD5+ DCs.

CD5 modulation agents can be any composition or method that can modulate CD5 expression on cells (e.g., DCs, LCs). For example, a CD5 modulation agent can be an activator, an inhibitor, an agonist, or an antagonist. As another example, the CD5 modulation can be the result of gene editing.

A CD5 modulation agent can be a CD5 antibody (e.g., a monoclonal antibody to CD5).

Figure 17A:
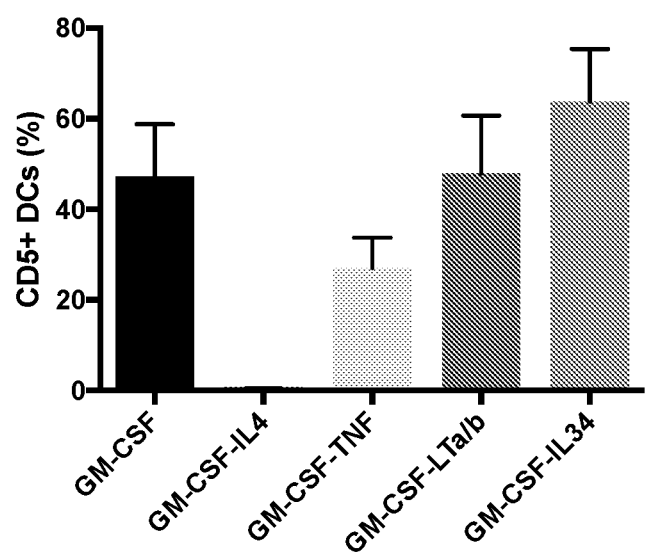
FIG. 17A-FIG. 17B is a series of bar graphs showing DCs differentiated from monocytes with the addition of cytokines.
Figure 17B:
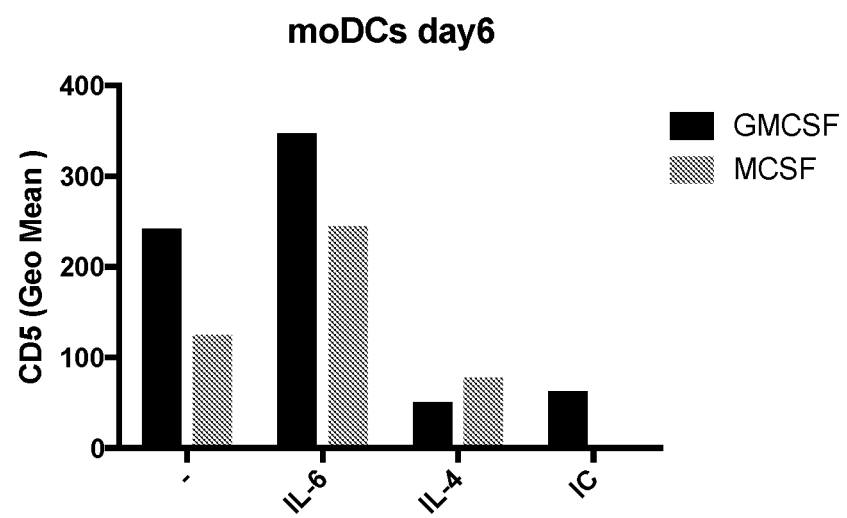

A CD5 modulating agent can be an agent that induces or inhibits progenitor cell differentiation into CD5 expressing cells (e.g., DCs or LCs). For example IL-4 can be used to block differentiation of monocytes (see e.g., FIG. 17). Monocytes can often differentiate to DCs in the body under inflammatory conditions.

As described herein, over-expression or activation of CD5 can result in enhanced CTL response. Cytokines, such as GMCSF and TNF-α are shown herein as an agent to expand CD5+ cells from progenitor cells.

Furthermore, it was discovered that TNF-α and LTα/β could significantly enhance CD5+ DC numbers.

Additionally, it was shown that TNF-α and LTα/β supported the differentiation of the CD5+ cells, while IL-4 blocked their differentiation.

Cytokines or Co-Stimulatory Molecules

Cytokines and other co-stimulatory molecules can be targeted for inhibition, activation, or expression for use in the treatment of diseases described herein.

As described herein, CD5 signals cells, such as DCs, to produce cytokines. Cytokines that can be targeted alone or in combination with an above CD5 modulating agent can be selected from one or more agents selected from the group consisting of: TNF-α, TNF-β, IL-34, IL-6, LTα/β, GM-CSF, SCF, FLT3-L, IL-22, IL-12p70, IL-18, IL-17, IL-4, IFN-α, IFN-γ, IL-18, IL-12p35, IL-23p19, IL-1β, IL-17A, IL-17F, or TGF-β.

Other interleukins that can be targeted can be IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, or IL-36.

For example, it was shown herein that the inhibition of IL-18 with anti-IL-18 inhibited the proliferation of CD8+ T cells primed with CD5+ DCs. For example, inhibition of IL-18 can be accomplished using an anti-IL-18 monoclonal antibody.

Other targets for CD5 modulation can include those that modulate STAT3. STAT3 can become activated after phosphorylation of tyrosine 705 in response to such ligands as interferons, epidermal growth factor (EGF), Interleukins (e.g., IL-5 and IL-6). A STAT3 inhibitor can be a JAK inhibitor. Inactivating STAT3 can be accomplished with a STAT3 inhibitor, STAT3 siRNA, or a STAT3 small molecule inhibitor.

CD45+ cells were shown to be increased in a model of inflammation. As such, CD45+ can be another therapeutic target.

Enhancement of CD5+ DC differentiation can be used in combination for checkpoint blockade therapy such as PD-1, PDL1, and/or CTLA-4 in cancer immunotherapy.

CD5 Signal Reduction, Elimination, or Inhibition by Small Molecule Inhibitors, shRNA, or siRNA As described herein, a CD5 modulation agent can be used (e.g., in combination with cytokines (e.g., interleukins)) for use in adoptive cellular therapy. A CD5 modulation agent can be used to reduce/eliminate or enhance/increase CD5 signals. For example, a CD5 modulation agent can be a small molecule inhibitor of CD5. As another example, a CD5 modulation agent can be a short hairpin RNA (shRNA). As another example, a CD5 modulation agent can be a short interfering RNA (siRNA). Manipulations can be done in progenitors and the differentiated DCs can be used as a tolerogenic vaccine (this is also relevant to the crispr cas9 manipulation method below).

Genome Editing

As described herein, CD5 signals can be modulated (e.g., reduced, eliminated, or enhanced) using genome editing. For example, genome editing can comprise CRISPR/Cas9. Adequate blockage of CD5 by genome editing can result in protection from autoimmune or inflammatory diseases. Because the CD5−/− mouse showed reduced ability to reject tumors and increase in CD5 expression results in increasing Th1, Th22, and CTL responses, enhancing CD5 expression with genome editing can be used to treat cancer.

Clustered regularly interspaced short palindromic repeats (CRISPR)/CRISPR-associated (Cas) systems are a new class of genome-editing tools that target desired genomic sites in mammalian cells. Recently published type II CRISPR/Cas systems use Cas9 nuclease that is targeted to a genomic site by complexing with a synthetic guide RNA that hybridizes to a 20-nucleotide DNA sequence and immediately preceding an NGG motif recognized by Cas9 (thus, a $(N)_{20}$NGG target DNA sequence). This results in a double-strand break three nucleotides upstream of the NGG motif. The double strand break instigates either non-homologous end-joining, which is error-prone and conducive to frameshift mutations that knock out gene alleles, or homology-directed repair, which can be exploited with the use of an exogenously introduced double-strand or single-strand DNA repair template to knock in or correct a mutation in the genome. Thus, CRISPR/Cas systems could be useful tools for therapeutic applications for attenuating inflammatory T cell responses to target cells by the removal of CD5 signals.

For example, the methods as described herein can comprise a method for altering a target polynucleotide sequence in a cell comprising contacting the polynucleotide sequence with a clustered regularly interspaced short palindromic repeats-associated (Cas) protein.

Treatment of Diseases, Disorders, and Conditions Using CD5 Modulation

The methods as described herein can be used in the treatment of diseases, disorders, or conditions that can be treated by modulating CD5 expression on cells.

For example, the methods as described herein can treat a disease disorder, or condition can be any disease disorder or condition associated with an increase in CD5, a pathogen or infectious disease that contains beta-glucan by expanding CD5 cells or expression of CD5.

Furthermore, the methods as described herein can treat an immune-mediated disorder dependent on IFN-γ and/or IL-22. Aberrant IFNγ expression is associated with a number of autoinflammatory and autoimmune diseases. IFN-γ associated diseases disorders, or conditions, can be an autoimmune disease, such as alopecia areata; autoimmune hemolytic anemia; autoimmune hepatitis; dermatomyositis; diabetes (type 1); some forms of juvenile idiopathic arthritis; glomerulonephritis; Graves' disease; Guillain-Barré syndrome; idiopathic thrombocytopenic purpura; myasthenia gravis; some forms of myocarditis; multiple sclerosis; pemphigus/pemphigoid; pernicious anemia; polyarteritis nodosa; polymyositis; primary biliary cirrhosis; psoriasis; rheumatoid arthritis; scleroderma/systemic sclerosis; Sjögren's syndrome; systemic lupus erythematosus; some forms of thyroiditis; some forms of uveitis; vitiligo; granulomatosis with polyangiitis (Wegener's); graft versus host disease; Crohn's disease; or colitis.

As another example, expansion of CD5+ DCs can induce a CTL response. As such, the methods as described herein can induce an immune response useful in a vaccine. Processes of immune inductions for vaccines are well known (see e.g., Wollard et al., Viral Vaccines and CTL Response Journal of Biomedicine and Biotechnology, Volume 2010 (2010)). Except as otherwise noted herein, therefore, the process of the present disclosure can be carried out in accordance with such processes.

The role of CD5 in inflammatory skin diseases is supported by elevated CD5 in psoriasis plaques and enhanced ability to drive Th1 and Th22 cell responses. As described herein, the present disclosure describes the discovery that Langerhans cells (LCs) and dermal $CD1a^{(dim)}CD141^-$ DCs are heterogeneous, containing terminally differentiating DCs that express CD5.

The present disclosure also demonstrates that CD5 KO mice were protected from psoriasis-like disease, demonstrating that CD5 is required for psoriasis inflammation. As such, CD5+ DCs can contribute to exacerbating inflammation in human psoriasis.

A CD5 associated disease (or disease associated with CD5) can be any disease that can be treated with, is affected by, or benefits from the modulation of CD5. For example, modulation of CD5 can be the activation of CD5, inhibition of CD5, induction of CD5, blocking CD5, upregulation of CD5, down regulation of CD5, increase or decrease in number of cells expressing CD5, increase or decrease in CD5 expression on cells, genome editing, modulating a factor in the CD5 signaling pathway, modulating monocytes or progenitor cells that can differentiate into CD5 expressing cells, or combination thereof. As described herein, a CD5 associated disease, disorder, or condition can be an inflammatory disease, an immune-mediated disorder, an inflammatory skin disease (e.g., psoriasis, atopic dermatitis, stasis dermatitis, allergic/irritant contact dermatitis, seborrheic dermatitis, lichen planus, urticarial, papular uritcaria, drug eruptions, bullous diseases, mastocytosis, eosinophilic folliculitis, pruritic popular eruption of HIV), or an autoimmune associated disease (e.g., scabies, lichen sclerosus, dermatomyositis, lupus erythematosus, graft versus host disease, Crohn's and colitis).

As described herein, increasing CD5 expression increased IL-6, TNFα, and IL-12p70. As such, modulation of CD5 can be used for TNF associated conditions, such as autoimmune disorders such as rheumatoid arthritis, ankylosing spondylitis, inflammatory bowel disease, psoriasis, hidradenitis suppurativa, or refractory asthma. IL-12 is associated with autoimmune diseases, psoriasis, and inflammatory bowel disease.

As another example, disease, disorder, or condition that can be treated by enhancing the CTL response (i.e., by expansion of CD5+ DCs with, e.g., cytokines GMCSF and TNFα) as well as IL-12 production can comprise cancer. For example, the cancer can be head and neck cancer, metastatic cancer, pancreatic cancer, prostate cancer, breast cancer, basal cell, melanoma, colon cancer, lung cancer, leukemia, or lymphoma.

The compositions and methods as described herein provide for an autologous cancer vaccine (or an autologous tumor cell vaccine) can be a therapeutic agent produced by isolating cells (e.g., tumor cells) from an individual and processing these cells into a vaccine formulation in vitro; the vaccine is then administered to the individual from whom the tumor cells were isolated. Typically combined with an adjuvant immunostimulant, an autologous cell vaccine may elicit a cytotoxic T-lymphocytic immune response to cell surface-expressed tumor-associated antigens (TAAs), resulting in tumor cell death. As an example, tumor or cancer cells can be isolated from a biological sample (e.g., blood) and treating the cells with a CD5 modulation agent (e.g., GMCSF, FLT3L, TNF-α, LTα/β). The activated cells could then be administered directly to the patient (e.g., to a target site or tumor).

As another example, the methods can treat an IL-18 associated disease, disorder, or condition. Because CD5+ DCs are also highly express IL-18, CD5+ associated diseases, disorders, and conditions can also comprise diseases, disorders, and conditions associated with IL-18. IL-18 has been shown to induce severe inflammatory reactions, signifying its role in certain inflammatory disorders. For example, IL-18 has been implicated in age-related macular degeneration, Hashimoto's thyroiditis, and Alzheimer's disease and psoriasis. Other diseases associated with IL18 include Adult-Onset Still's Disease and Sapho Syndrome.

A beta-glucan associated disease, disorder, or condition can be any pathogen or infectious disease that contains beta-glucans. For example, infectious diseases or pathogens that contain beta glucans can include bacteria (e.g., mycobacteria, such as mycobacteria tuberculosis, mycobacteria bovis) and fungi. For example, the species of *mycobacterium* can be *M. abscessus; M. africanum; M. agri; M. aichiense; M. alvei; M. arosiense; M. arupense; M. asiaticum; M. aubagnense; M. aurum; M. austroafricanum; M. avium; M. avium "hominissuis"; M. avium paratuberculosis; M. avium silvaticum; M. boenickei; M. bohemicum; M. bolletii; M. botniense; M. bovis; M. bovis BCG; M. branderi; M. brisbanense; M. brumae; M. canariasense; M. canetti; M. caprae; M. celatum; M. chelonae; M. chimaera; M. chitae; M. chlorophenolicum; M. chubuense; M. colombiense; M. conceptionense; M. confluentis; M. conspicuum; M. cookii; M. cosmeticum; M. diernhoferi; M. doricum; M. duvalii; M. elephantis; M. fallax; M. farcinogenes; M. flavescens; M. florentinum; M. fluoroanthenivorans; M. fortuitum; M. fortuitum subsp. acetamidolyticum; M. frederiksbergense; M. gadium; M. gastri; M. genavense; M. gilvum; M. goodii; M. gordonae; M. haemophilum; M. hassiacum; M. heckeshornense; M. heidelbergense; M. hiberniae; M. hodleri; M. holsaticum; M. houstonense; M. immunogenum; M. indicus pranii; M. interjectum; M. intermedium; M. intracellulare; M. kansasii; M. komossense; M. kubicae; M. kumamotonense; M. lacus; M. lentiflavum; M. leprae; M. lepraemurium; M. lepromatosis; M. madagascariense; M. mageritense; M. malmoense; M. marinum; M. massiliense; M. microti; M. monacense; M. montefiorense; M. moriokaense; M. mucogenicum; M. murale; M. nebraskense; M. neoaurum; M. neworleansense; M. non-chromogenicum; M. novocastrense; M. obuense; M. palustre; M. parafortuitum; M. parascrofulaceum; M. parmense; M. peregrinum; M. phlei; M. phocaicum; M. pinnipedii; M. porcinum; M. poriferae; M. pseudoshottsii; M. psychrotolerans; M. pulveris; M. pyrenivorans; M. rhodesiae; M. saskatchewanense; M. scrofulaceum; M. senegalense; M. seoulense; M. septicum; M. shimoidei; M. shottsii; M. simiae; M. smegmatis; M. sphagni; M. szulgai; M. terrae; M. thermoresistibile; M. tokaiense; M. triplex; M. triviale; M. tuberculosis; M. tusciae; M. ulcerans; M. vaccae; M. vanbaalenii; M. wolinskyi; M. xenopi*; or *M. yongonense*.

Molecular Engineering

The following definitions and methods are provided to better define the present invention and to guide those of ordinary skill in the art in the practice of the present invention. Unless otherwise noted, terms are to be understood according to conventional usage by those of ordinary skill in the relevant art.

The terms "heterologous DNA sequence", "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

Expression vector, expression construct, plasmid, or recombinant DNA construct is generally understood to refer to a nucleic acid that has been generated via human intervention, including by recombinant means or direct chemical synthesis, with a series of specified nucleic acid elements that permit transcription or translation of a particular nucleic acid in, for example, a host cell. The expression vector can be part of a plasmid, virus, or nucleic acid fragment. Typically, the expression vector can include a nucleic acid to be transcribed operably linked to a promoter.

A "promoter" is generally understood as a nucleic acid control sequence that directs transcription of a nucleic acid. An inducible promoter is generally understood as a promoter that mediates transcription of an operably linked gene in response to a particular stimulus. A promoter can include necessary nucleic acid sequences near the start site of transcription, such as, in the case of a polymerase II type promoter, a TATA element. A promoter can optionally include distal enhancer or repressor elements, which can be located as much as several thousand base pairs from the start site of transcription.

A "transcribable nucleic acid molecule" as used herein refers to any nucleic acid molecule capable of being transcribed into a RNA molecule. Methods are known for introducing constructs into a cell in such a manner that the transcribable nucleic acid molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present disclosure, conventional compositions and methods for preparing and using constructs and host cells are well known to one skilled in the art (see e.g., Sambrook and Russel (2006)

Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754).

The "transcription start site" or "initiation site" is the position surrounding the first nucleotide that is part of the transcribed sequence, which is also defined as position +1. With respect to this site all other sequences of the gene and its controlling regions can be numbered. Downstream sequences (i.e., further protein encoding sequences in the 3' direction) can be denominated positive, while upstream sequences (mostly of the controlling regions in the 5' direction) are denominated negative.

"Operably-linked" or "functionally linked" refers preferably to the association of nucleic acid sequences on a single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. The two nucleic acid molecules may be part of a single contiguous nucleic acid molecule and may be adjacent. For example, a promoter is operably linked to a gene of interest if the promoter regulates or mediates transcription of the gene of interest in a cell.

A "construct" is generally understood as any recombinant nucleic acid molecule such as a plasmid, cosmid, virus, autonomously replicating nucleic acid molecule, phage, or linear or circular single-stranded or double-stranded DNA or RNA nucleic acid molecule, derived from any source, capable of genomic integration or autonomous replication, comprising a nucleic acid molecule where one or more nucleic acid molecule has been operably linked.

A constructs of the present disclosure can contain a promoter operably linked to a transcribable nucleic acid molecule operably linked to a 3' transcription termination nucleic acid molecule. In addition, constructs can include but are not limited to additional regulatory nucleic acid molecules from, e.g., the 3'-untranslated region (3' UTR). Constructs can include but are not limited to the 5' untranslated regions (5' UTR) of an mRNA nucleic acid molecule which can play an important role in translation initiation and can also be a genetic component in an expression construct. These additional upstream and downstream regulatory nucleic acid molecules may be derived from a source that is native or heterologous with respect to the other elements present on the promoter construct.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism such as a bacterium, cyanobacterium, animal or a plant into which a heterologous nucleic acid molecule has been introduced. The nucleic acid molecule can be stably integrated into the genome as generally known in the art and disclosed (Sambrook 1989; Innis 1995; Gelfand 1995; Innis & Gelfand 1999). Known methods of PCR include, but are not limited to, methods using paired primers, nested primers, single specific primers, degenerate primers, gene-specific primers, vector-specific primers, partially mismatched primers, and the like. The term "untransformed" refers to normal cells that have not been through the transformation process.

"Wild-type" refers to a virus or organism found in nature without any known mutation.

Design, generation, and testing of the variant nucleotides, and their encoded polypeptides, having the above required percent identities and retaining a required activity of the expressed protein is within the skill of the art. For example, directed evolution and rapid isolation of mutants can be according to methods described in references including, but not limited to, Link et al. (2007) Nature Reviews 5(9), 680-688; Sanger et al. (1991) Gene 97(1), 119-123; Ghadessy et al. (2001) Proc Natl Acad Sci USA 98(8) 4552-4557. Thus, one skilled in the art could generate a large number of nucleotide and/or polypeptide variants having, for example, at least 95-99% identity to the reference sequence described herein and screen such for desired phenotypes according to methods routine in the art.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

Generally, conservative substitutions can be made at any position so long as the required activity is retained. So-called conservative exchanges can be carried out in which the amino acid which is replaced has a similar property as the original amino acid, for example the exchange of Glu by Asp, Gln by Asn, Val by Ile, Leu by Ile, and Ser by Thr. For example, amino acids with similar properties can be Aliphatic amino acids (e.g., Glycine, Alanine, Valine, Leucine, Isoleucine); Hydroxyl or sulfur/selenium-containing amino acids (e.g., Serine, Cysteine, Selenocysteine, Threonine, Methionine); Cyclic amino acids (e.g., Proline); Aromatic amino acids (e.g., Phenylalanine, Tyrosine, Tryptophan); Basic amino acids (e.g., Histidine, Lysine, Arginine); or Acidic and their Amide (e.g., Aspartate, Glutamate, Asparagine, Glutamine). Deletion is the replacement of an amino acid by a direct bond. Positions for deletions include the termini of a polypeptide and linkages between individual protein domains. Insertions are introductions of amino acids into the polypeptide chain, a direct bond formally being replaced by one or more amino acids. Amino acid sequence can be modulated with the help of art-known computer simulation programs that can produce a polypeptide with, for example, improved activity or altered regulation. On the basis of this artificially generated polypeptide sequences, a corresponding nucleic acid molecule coding for such a modulated polypeptide can be synthesized in-vitro using the specific codon-usage of the desired host cell.

"Highly stringent hybridization conditions" are defined as hybridization at 65° C. in a 6×SSC buffer (i.e., 0.9 M sodium chloride and 0.09 M sodium citrate). Given these conditions, a determination can be made as to whether a given set of sequences will hybridize by calculating the melting temperature ($T_m$) of a DNA duplex between the two sequences. If a particular duplex has a melting temperature lower than 65° C. in the salt conditions of a 6×SSC, then the two sequences will not hybridize. On the other hand, if the melting temperature is above 65° C. in the same salt conditions, then the sequences will hybridize. In general, the melting temperature for any hybridized DNA:DNA sequence can be determined using the following formula: $T_m = 81.5°$ C.$+16.6(\log_{10} [Na^+])+0.41$(fraction G/C content)$-0.63$(% formamide)$-(600/l)$. Furthermore, the $T_m$ of a DNA:DNA hybrid is decreased by 1-1.5° C. for every 1% decrease in nucleotide identity (see e.g., Sambrook and Russel, 2006).

Host cells can be transformed using a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754). Such techniques include, but are not limited to, viral infection, calcium phosphate transfection, liposome-mediated transfection, microprojectile-mediated delivery, receptor-mediated uptake, cell fusion, electroporation, and the like. The transfected cells can be selected and propagated to provide recombinant host cells that comprise the expression vector stably integrated in the host cell genome.

Exemplary nucleic acids which may be introduced to a host cell include, for example, DNA sequences or genes from another species, or even genes or sequences which originate with or are present in the same species, but are incorporated into recipient cells by genetic engineering methods. The term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the cell, DNA from another individual of the same type of organism, DNA from a different organism, or a DNA generated externally, such as a DNA sequence containing an antisense message of a gene, or a DNA sequence encoding a synthetic or modified version of a gene.

Host strains developed according to the approaches described herein can be evaluated by a number of means known in the art (see e.g., Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Methods of down-regulation or silencing genes are known in the art. For example, expressed protein activity can be down-regulated or eliminated using antisense oligonucleotides, protein aptamers, nucleotide aptamers, and RNA interference (RNAi) (e.g., small interfering RNAs (siRNA), short hairpin RNA (shRNA), and micro RNAs (miRNA) (see e.g., Fanning and Symonds (2006) Handb Exp Pharmacol. 173, 289-303G, describing hammerhead ribozymes and small hairpin RNA; Helene, C., et al. (1992) Ann. N.Y. Acad. Sci. 660, 27-36; Maher (1992) Bioassays 14(12): 807-15, describing targeting deoxyribonucleotide sequences; Lee et al. (2006) Curr Opin Chem Biol. 10, 1-8, describing aptamers; Reynolds et al. (2004) Nature Biotechnology 22(3), 326-330, describing RNAi; Pushparaj and Melendez (2006) Clinical and Experimental Pharmacology and Physiology 33(5-6), 504-510, describing RNAi; Dillon et al. (2005) Annual Review of Physiology 67, 147-173, describing RNAi; Dykxhoorn and Lieberman (2005) Annual Review of Medicine 56, 401-423, describing RNAi). RNAi molecules are commercially available from a variety of sources (e.g., Ambion, TX; Sigma Aldrich, MO; Invitrogen). Several siRNA molecule design programs using a variety of algorithms are known to the art (see e.g., Cenix algorithm, Ambion; BLOCK-iT™ RNAi Designer, Invitrogen; siRNA Whitehead Institute Design Tools, Bioinofrmatics & Research Computing). Traits influential in defining optimal siRNA sequences include G/C content at the termini of the siRNAs, Tm of specific internal domains of the siRNA, siRNA length, position of the target sequence within the CDS (coding region), and nucleotide content of the 3' overhangs.

Formulation

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Md., 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutical active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intramuscular, intraperitoneal, intravenous, subcutaneous, intranasal, epidural, ophthalmic, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Therapeutic Methods

Also provided is a process of treating a CD5 associated disease, disorder, or condition in a subject in need administration of a therapeutically effective amount of a CD5 modulation agent, so as to modulate CD5 expression on dendritic cells, modulate the number of CD5$^+$ cells, or modulate the expansion of CD5$^+$ cells by modulation of differentiation of progenitors to CD5 expressing dendritic cells.

Methods described herein are generally performed on a subject in need thereof. A subject in need of the therapeutic methods described herein can be a subject having, diagnosed with, suspected of having, or at risk for developing a CD5 associated disease, disorder, or condition. A determination of the need for treatment will typically be assessed by a history and physical exam consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and chickens, and humans. For example, the subject can be a human subject.

Generally, a safe and effective amount of a CD5 modulation agent is, for example, that amount that would cause the desired therapeutic effect in a subject while minimizing undesired side effects. In various embodiments, an effective amount of a CD5 modulation agent described herein can substantially inhibit a CD5 associated disease, disorder, or condition; slow the progress of a CD5 associated disease, disorder, or condition; limit the development of a CD5 associated disease, disorder, or condition; or enhance therapeutic effect in the case of cancer upon induction of CD5$^+$ DCs.

According to the methods described herein, administration can be parenteral, pulmonary, oral, topical, intradermal, intramuscular, intraperitoneal, intravenous, subcutaneous, intranasal, epidural, ophthalmic, buccal, or rectal administration.

When used in the treatments described herein, a therapeutically effective amount of a CD5 modulation agent can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to modulate CD5 expression or substantially inhibit a CD5 associated disease, disorder, or condition, slow the progress of a CD5 associated disease, disorder, or condition, or limit the development of a CD5 associated disease, disorder, or condition.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, $4^{th}$ ed., Lippincott Williams & Wilkins, ISBN 0781741475; Shargel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of a CD5 modulation agent (which can include CD5$^+$ DCs in the form of a vaccine or targeting reagents specific to the CD5$^+$ DCs that can activate it specifically) can occur as a single event or over a time course of treatment. For example, a CD5 modulation agent can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities for a CD5 associated disease, disorder, or condition.

A CD5 modulation agent (e.g., an agent that can enhance, induce, eliminate, or reduce the expression of CD5) can be administered simultaneously or sequentially with another agent, such as a cancer therapeutic, an antibiotic, an anti-inflammatory, a checkpoint blockade therapy, or another agent used for the treatment of a CD5 associated disease, disorder, or condition. For example, a CD5 modulation agent can be administered simultaneously with another agent, such as an antibiotic or an anti-inflammatory. Simultaneous administration can occur through administration of separate compositions, each containing one or more of a CD5 modulation agent, an antibiotic, an anti-inflammatory, or another agent used for the treatment of a CD5 associated disease, disorder, or condition. Simultaneous administration can occur through administration of one composition containing two or more of a CD5 modulation agent, an antibiotic, an anti-inflammatory, or another agent used for the treatment of a CD5 associated disease, disorder, or condition. A CD5 modulation agent can be administered sequentially with an antibiotic, an anti-inflammatory, or another agent used for the treatment of a CD5 associated disease, disorder, or condition. For example, a CD5 modulation agent can be administered before or after administration of an antibiotic, an anti-inflammatory, or another agent used for the treatment of a CD5 associated disease, disorder, or condition.

Administration

Agents and compositions described herein can be administered according to methods described herein in a variety of means known to the art. The agents and compositions can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, intramuscular, implanted, intratumoral, intraperitoneal, intravenous, subcutaneous, intranasal, epidural, ophthalmic, buccal, or rectal administration.

Agents and compositions described herein can be administered in a variety of methods well known in the arts. Administration can include, for example, methods involving oral ingestion, direct injection (e.g., systemic or stereotactic), implantation of cells treated or engineered to express or secrete a factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 µm), nanospheres (e.g., less than 1 µm), microspheres (e.g., 1-100 µm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can:

provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to one or more CD5 modulating agents. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Identification of a Novel Skin Inflammatory Dendritic Cell Marked by CD5 that Dominates Psoriatic Plaques The following example describes the discovery that Langerhans cells and dermal $CD1a^{(dim)}CD141^-$ DCs are heterogeneous, containing terminally differentiating DCs that express CD5. CD5 signals DCs to produce cytokines, their role in inflammatory skin diseases is supported by their elevated numbers in psoriasis plaques and enhanced ability to drive Th1 and Th22 cell responses. Our findings also show that CD5 KO mice were protected from psoriasis-like disease, demonstrating that CD5 is required for psoriasis inflammation. As such, it is believed that $CD5^+$ DCs contribute to exacerbate inflammation in human psoriasis.

Figure 1A:
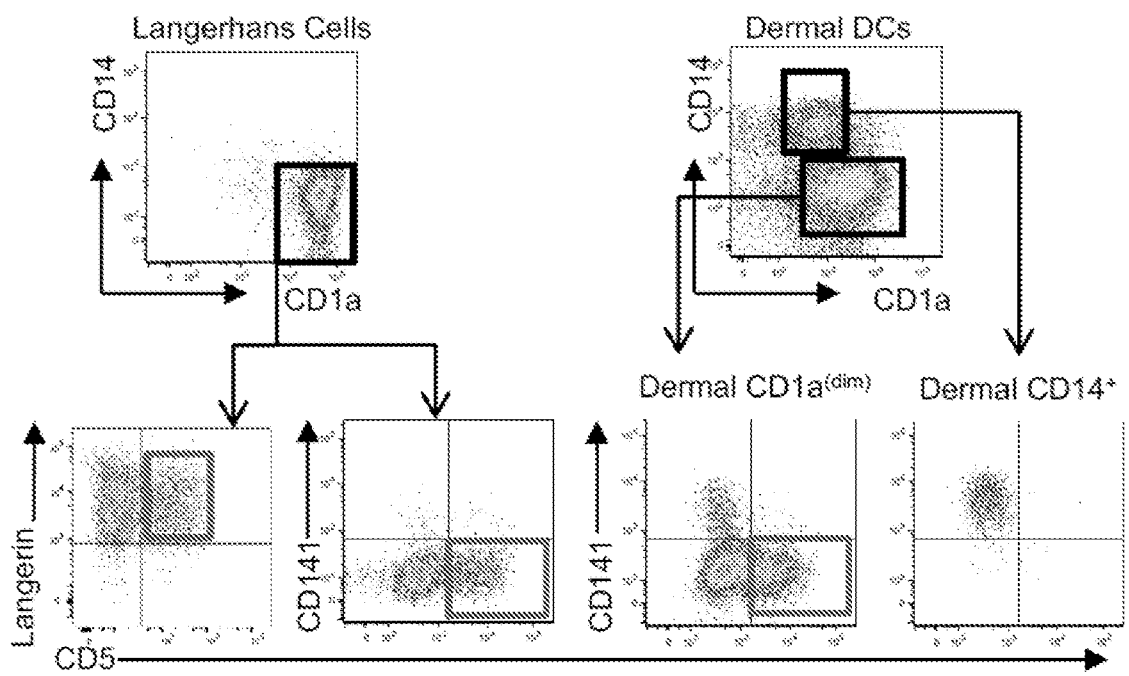
FIG. 1A-1E is a series of plots graphs and images showing the identification of new Langerhans Cells and dermal DC subsets in human skin.
Figure 1B:
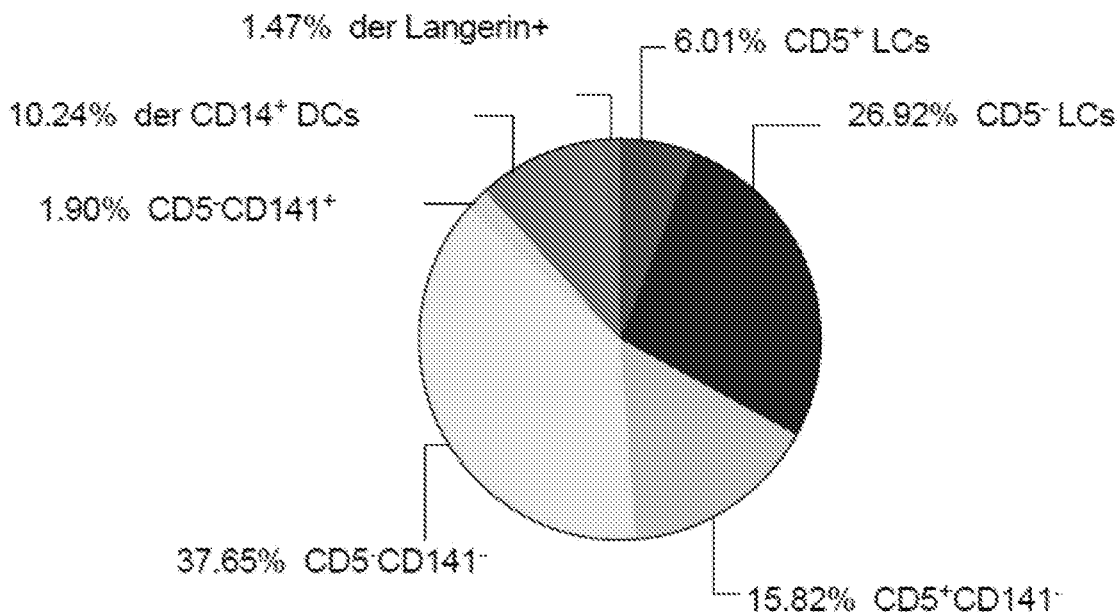
Figure 1C:
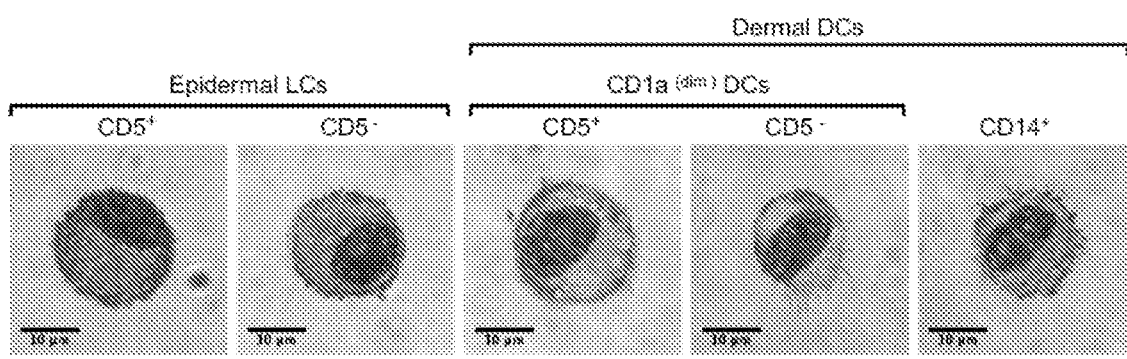
Figure 1D:
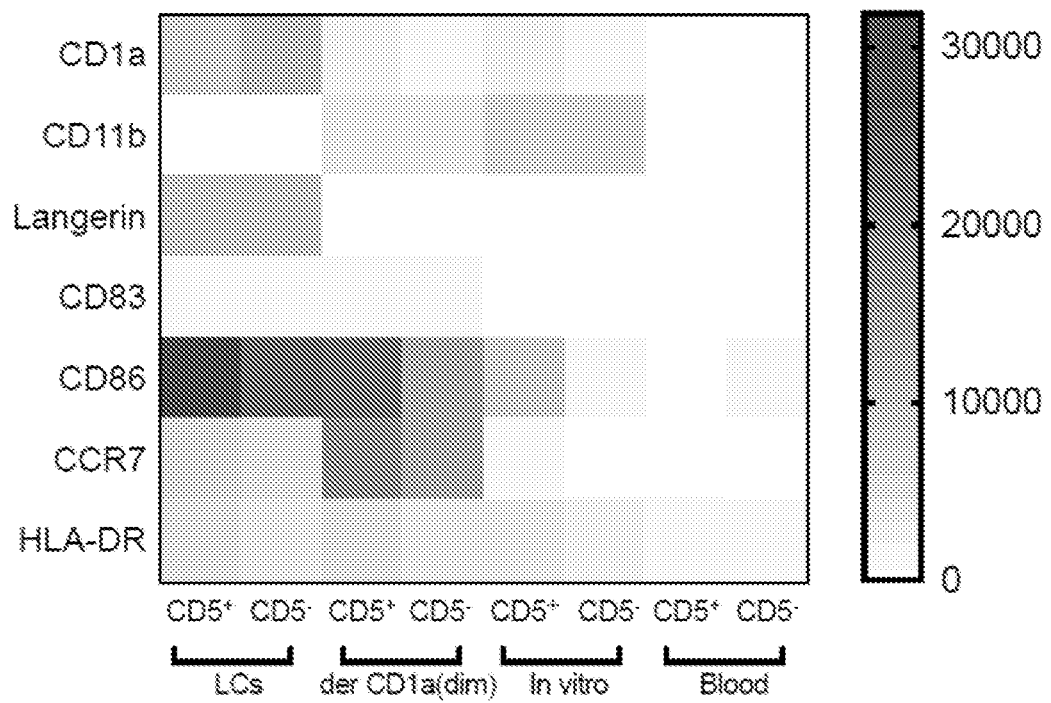
Figure 10A:
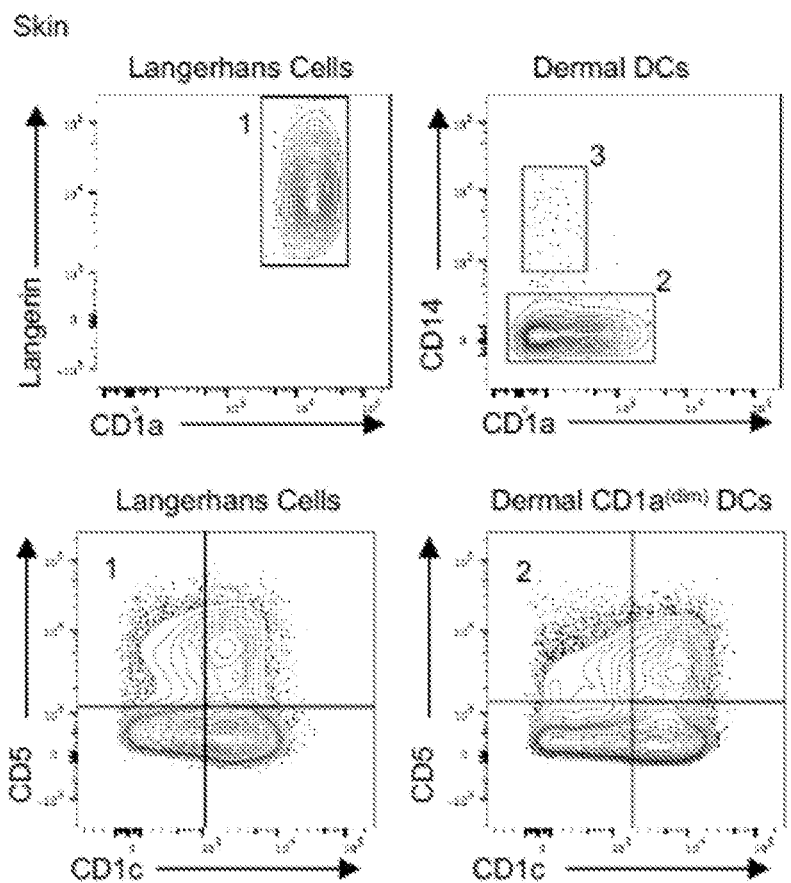
FIG. 10A-FIG. 10C is a series of flow cytometry plots showing the gating strategy used for and characterization of skin and blood CD5+ DCs.
Figure 10B:
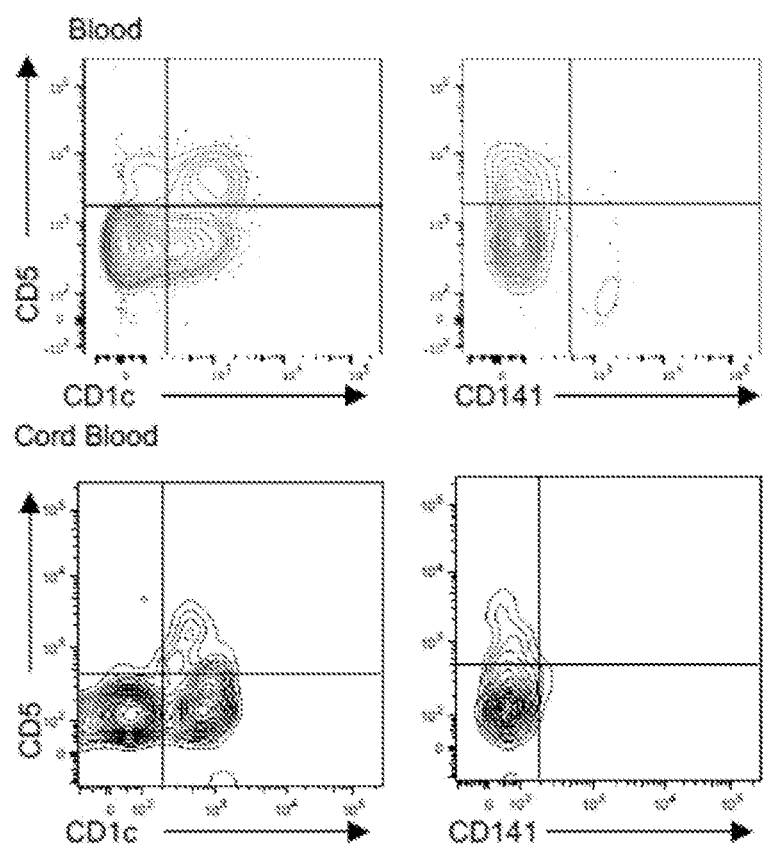
Figure 10C:
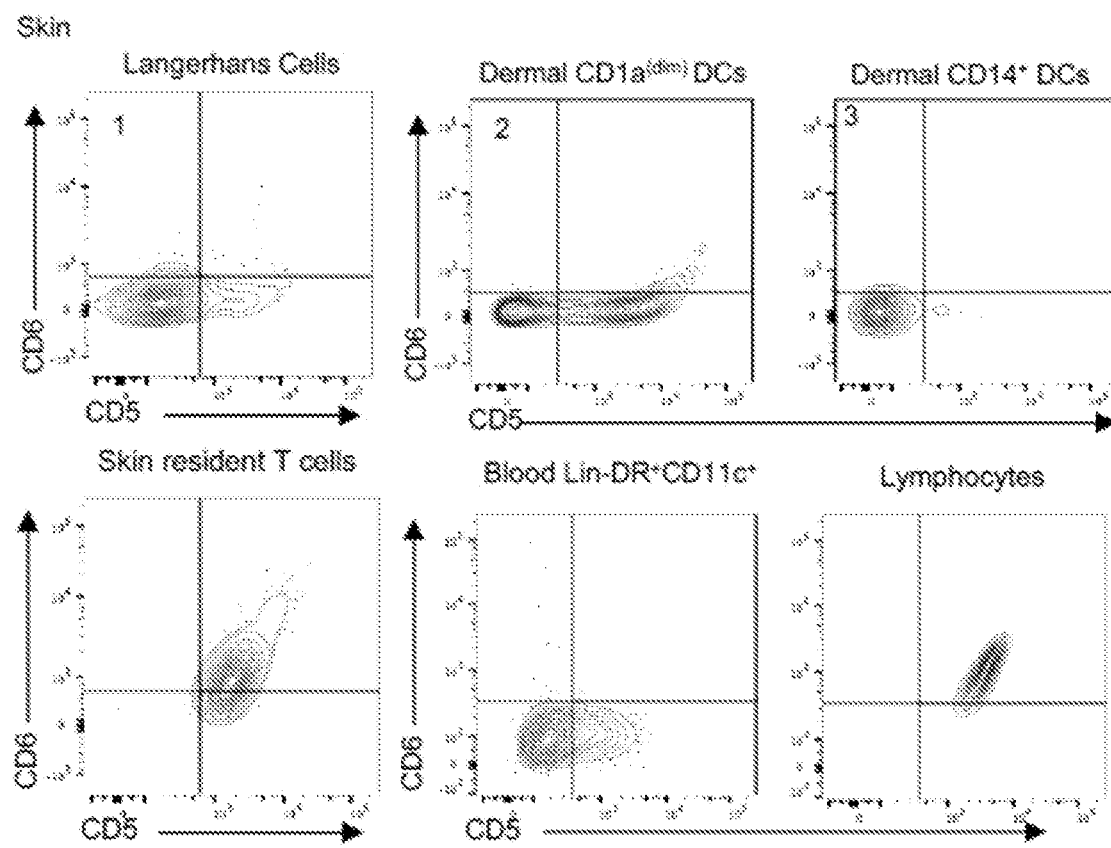

CD5 Marks a Subset of Epidermal LCs and Dermal $CD1a^{(dim)}$ DCs in Healthy Skin Human skin is known to contain four distinct myeloid DC subsets. Three of these, marked as $CD1a^{(dim)}CD141^-$, $CD1a^{(dim)}CD141^+$, or $CD1a^-CD14^+$, are found in the dermis, while $CD1a^{(hi)}Langerin^+$ LCs are found in the epidermis (Klechevsky, 2013; Nestle et al., 1993). To define unique surface markers and to fully characterize expression patterns of each epidermal and dermal subset, we performed a flow cytometry analysis of 332 different DC surface proteins. After gating on each DC subset, strikingly, we found that both LCs and dermal $CD1a^{(dim)}CD141^-$ DCs are heterogeneous in 33 tested donors containing distinct $CD5^+$ and $CD5^-$ populations (FIG. 1A). The $CD5^+$ LCs fraction comprised an average±SEM of 6±1.05% and the $CD5^+$ DCs fraction comprised an average±SEM of 15.8±2.1% of skin DCs (FIG. 1B). The CD5-positive cells in both the epidermis and the dermis displayed DC morphology, and were undistinguishable from their negative counterparts (FIG. 10). The $CD5^+$ cells in both epidermis and dermis expressed CD1c (FIG. 10A) and the epidermis $CD5^+$ LCs expressed higher amounts of CD1a and Langerin (FIG. 1A; left and FIG. 1D). CD5 was not expressed on skin CD141-expressing cells, including dermal $CD1a^{(dim)}CD141^+$ or dermal $CD14^+$ DCs (FIG. 1A; right). In the skin only dermal $CD5^+$ and $CD5^-$ but not epidermal $CD5^+$ and $CD5^-$ expressed CD11b, conversely, only epidermal $CD5^+$ and $CD5^-$ but not dermal $CD5^+$ and $CD5^-$ expressed CD11b (FIG. 1D). Interestingly, CD5 was also expressed on a subset of peripheral blood and cord blood $CD11c^+CD1c^+$ DCs but not on the $CD11c^+CD141^+$ DCs (FIG. 10A). While skin $CD5^+$ DCs express higher amounts of CD83, CD86 and CCR7 than blood DCs, the expression of these markers was comparable to their skin $CD5^-$ DCs counterparts. Both blood and skin $CD5^+$ DCs lacked the expression of CD14, CD141 (BDCA-3) (FIG. 10A) CD103, Sirp-α, CLA, CX3CR1, CD40, CD123 and BDCA-2 (not shown). Because CD5 and CD6 are often co-expressed on the surface of T cells or B cells (Gimferrer et al., 2003), the expression of CD6 on the surface of skin $CD5^+$ DCs or skin-resident T cells was assessed. Interestingly, CD6 was absent from the surface of the DCs in the skin, but was expressed on the surface of skin-resident T cells (FIG. 10B). This feature was shared with the blood $CD1c^+CD5^+$ DCs Thus, CD5 marks a novel population of human blood $CD1c^+$ and skin LCs and dermal $CD1a^{(dim)}$ DCs.

CD5 Marks a Stable Terminally Differentiated DC Subset

Figure 1E:
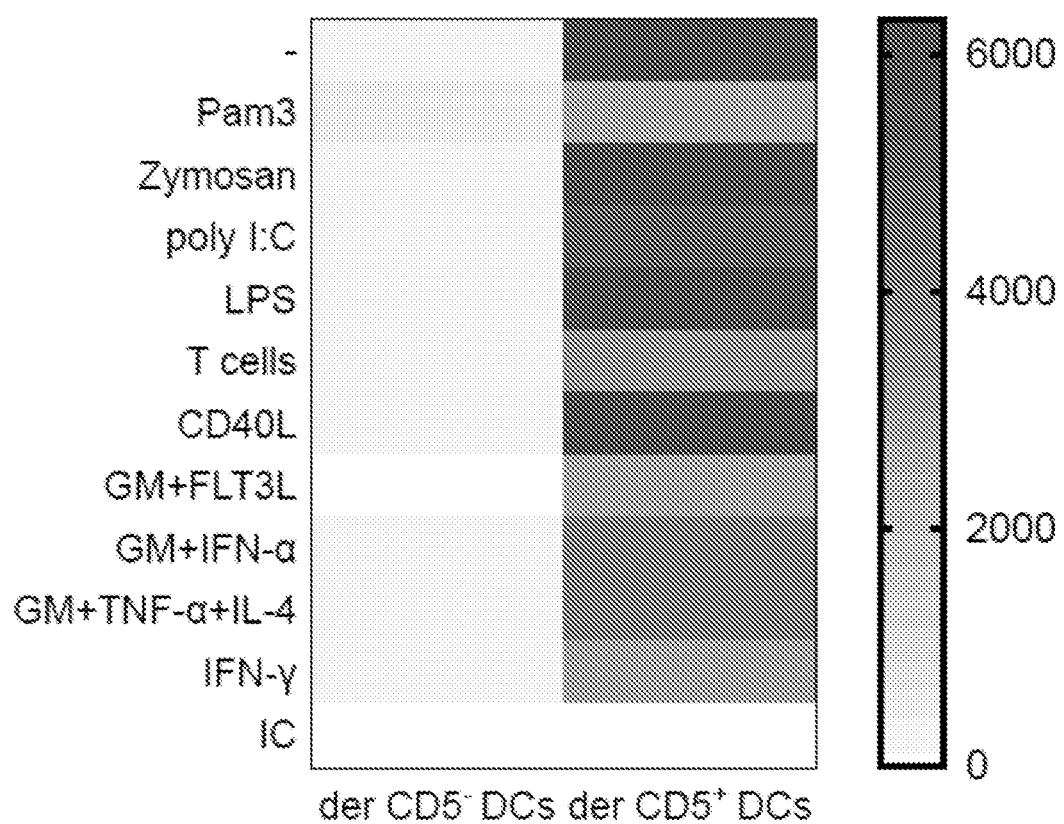

One indication of whether CD5 demarcates a distinct cell fate of DCs rather than just constituting an activation marker would be its stability on the surface of a cell. Thus, the stability of CD5 expression on the DC was tested in culture. Indeed, after six days in culture, CD5 was present on the cell surface of $CD5^+$ DCs and remained negative on the $CD5^-$ DC subset (FIG. 1E). To further assess whether CD5 marks a specific terminally differentiated cell fate, $CD5^+$ and $CD5^-$ DCs were sorted from human dermis and exposed for six days to a variety of stimuli (including Toll-like receptors (TLR-2, 3, 4)-agonists, inflammatory, or DC differentiating cytokines (IFN-γ, IFN-α, FLT3-L, GM-CSF, IL-4) or a T cell signal (T cells or T cell helper co-stimulation (CD40L)). Under these conditions, as well, CD5 remained on the surface of the positive cells and its level of expression did not change significantly (FIG. 1E; right). Moreover, CD5-expression was not detected on the stimulated $CD5^-$ DCs (FIG. 1E; left). Overall, this data demonstrates that CD5 marks a distinct and stable terminally differentiated DCs.

Dermal $CD5^+$ DCs Efficiently Prime Allogeneic Naïve $CD8^+$ T Cells

Figure 2A:
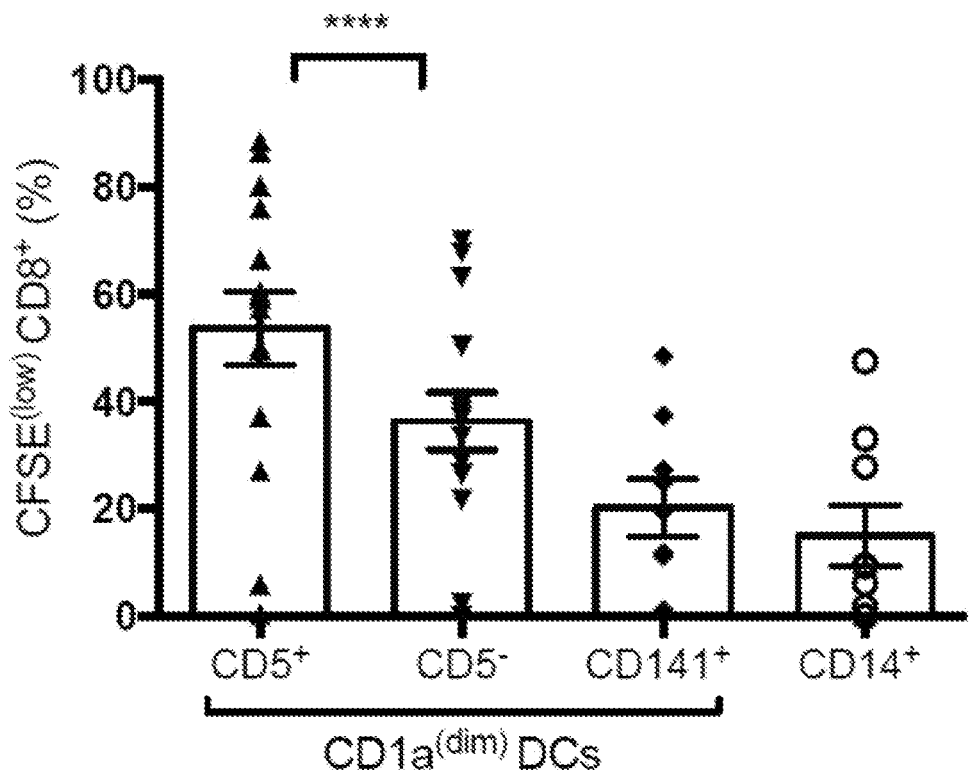
FIG. 2A-FIG. 2F is a series of bar graphs and plots showing dermal CD5$^+$ DCs are more efficient than their CD5$^-$ counterparts at priming CTLs.
Figure 2B:
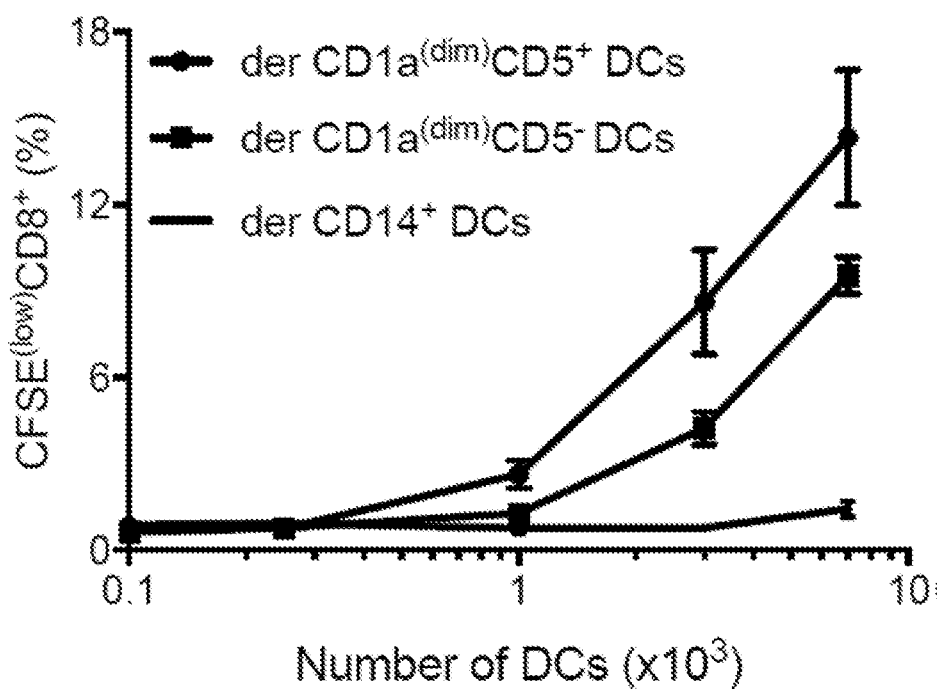
Figure 2C:
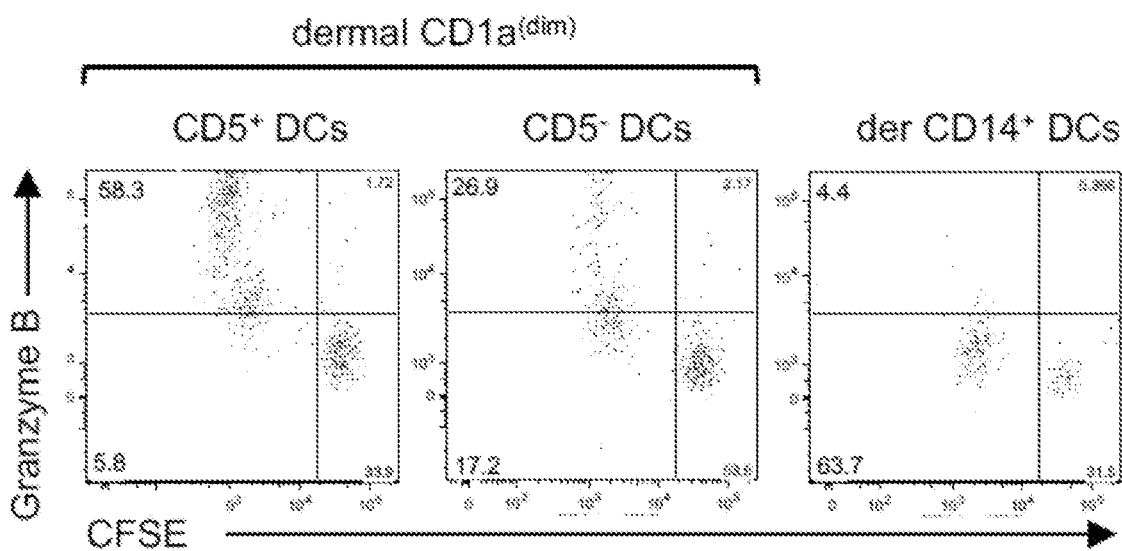

We initially assessed the biological properties of $CD5^+$ DCs from the dermis by measuring their capacity to activate allogeneic naive $CD8^+$ T cells ($CCR7^+CD45RA^+CD45RO^-$). Sorted live $HLA-DR^+CD1a^{(dim)}CD5^+$ DCs or the $CD5^-$ counterparts were co-cultured with allogeneic naïve T cells and analyzed after seven days for T cell proliferation. As shown in FIG. 2A, $CD5^+$ DCs were more powerful stimulators of naive $CD8^+$ T cell proliferation than the $CD5^-$ DCs, as measured by the dilution of CFSE (FIG. 2A-FIG. 2C). Dermal $CD1a^{(dim)}CD141^+$ and $CD14^+$ DCs served as controls and induced only weak CTL responses.

Figure 2D:
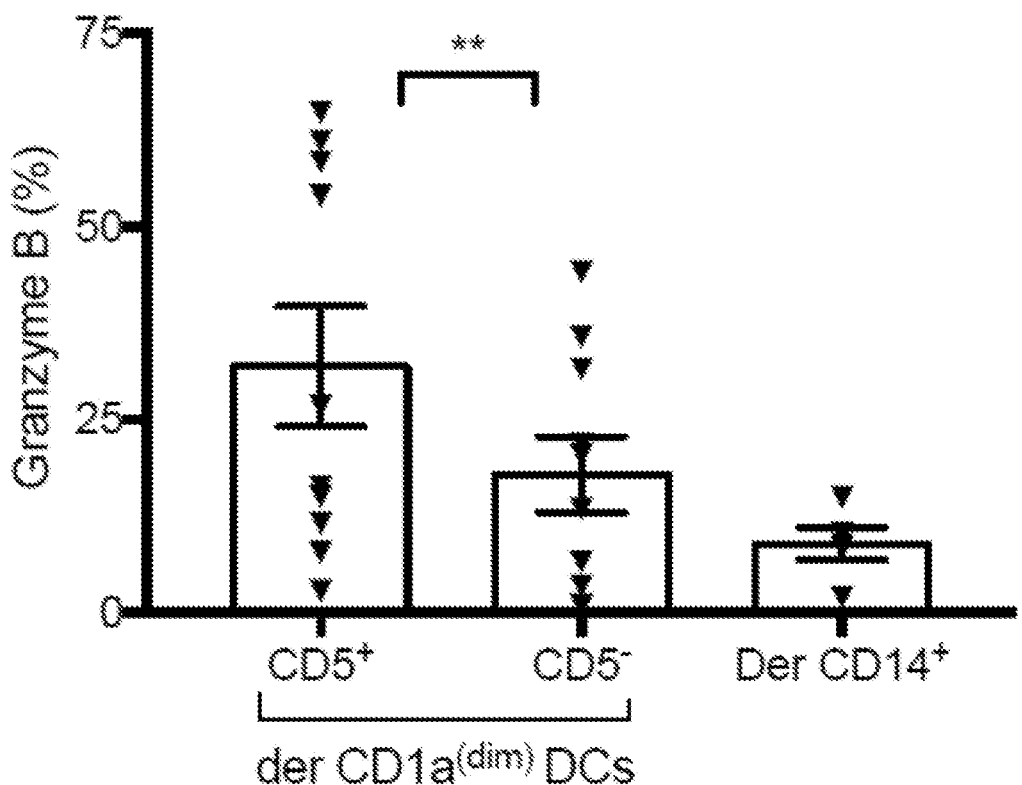
Figure 2E:
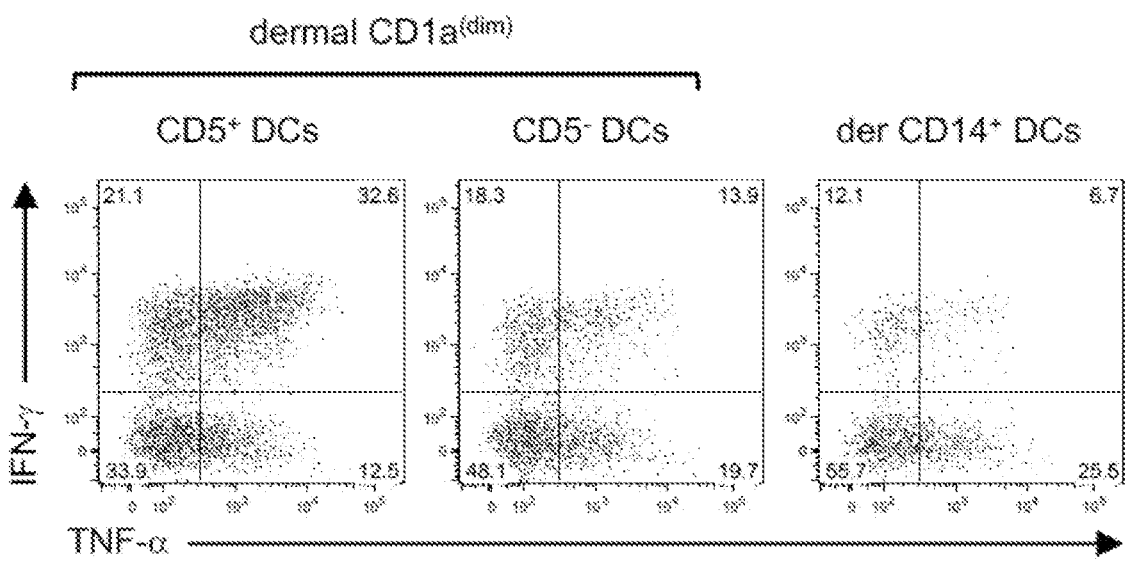
Figure 2F:
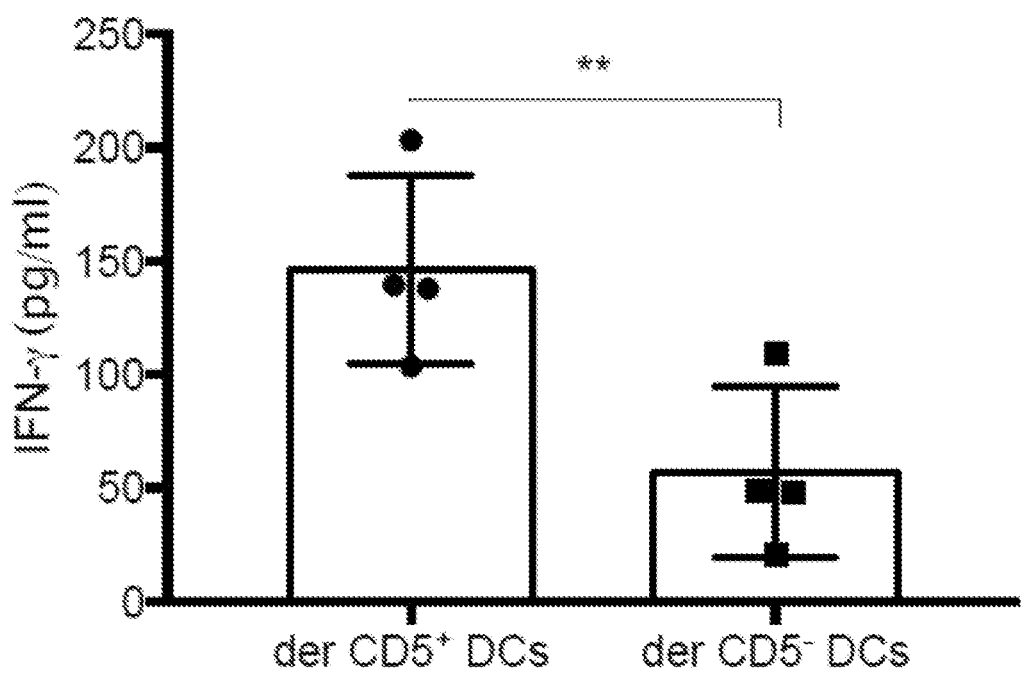

This is consistent with previous reports (Artyomov et al., 2015; Klechevsky et al., 2008). $CD8^+$ T cells primed with $CD5^+$ dermal DCs expressed higher levels of granzyme B compared to $CD8^+$ naïve T cells primed with matched $CD5^-$ DCs (FIG. 2C and FIG. 2D). Moreover, we observed greater expansion of IFN-γ and TNF-α-producing $CD8^+$ T cells by $CD5^+$ dermal DCs as measured intracellularly by flow cytometry (FIG. 2E). Furthermore, $CD8^+$ T cells that were primed by $CD5^+$ dermal $CD1a^{(dim)}$ DCs produced less IFN-γ compared to the one primed by the $CD5^-$ dermal $CD1a^{(dim)}$ DCs as measured in culture supernatant per cell (FIG. 2F). Overall, our data show that the $CD5^+$ DC subset has a specialized capacity to prime multifunctional $CD8^+$ T cell immunity.

Dermal $CD5^+$ DCs Polarize Naïve $CD4^+$ T Cells into Th1 and Th22 Cells

Figure 3A:
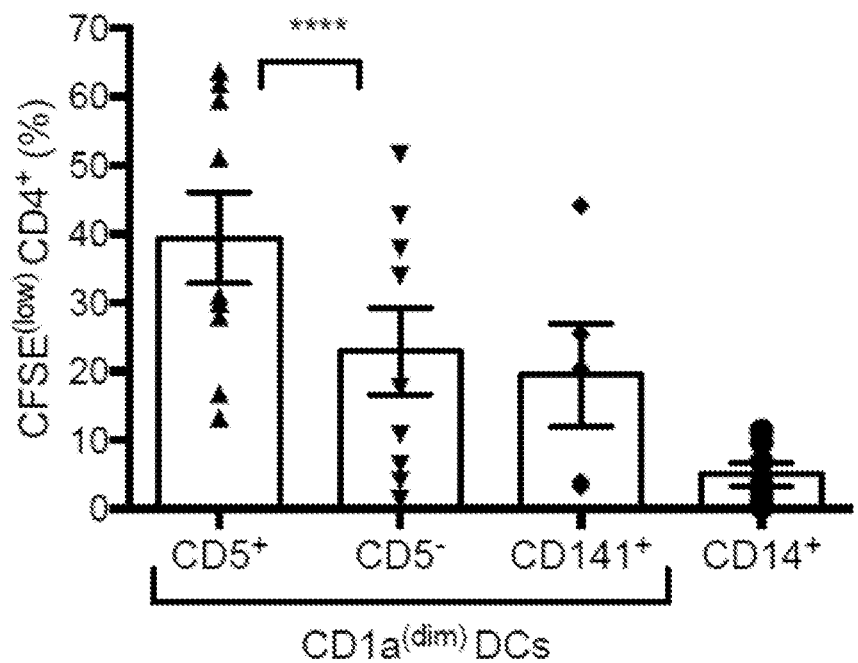
Figure 3B:
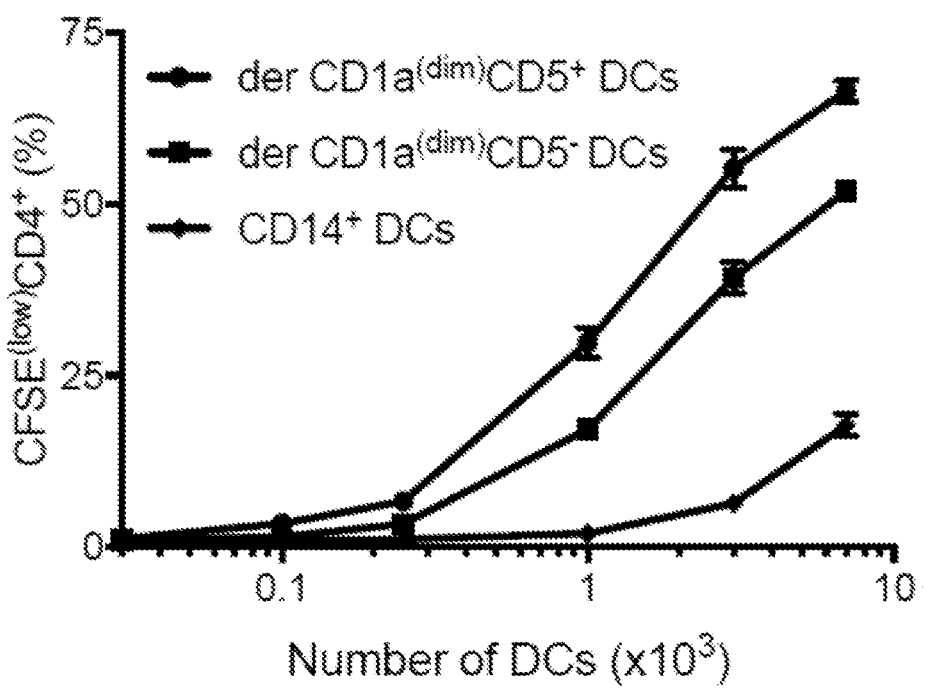

To address whether $CD5^+$ DC populations play a specific role in inducing the differentiation of T-helper cell subsets, we co-cultured sorted dermal $CD5^+$ or $CD5^-$ DCs with allogeneic naïve T cells. After six to eight days, dermal $CD5^+$ DCs induced higher levels of CFSE dilution compared to their $CD5^-$ counterparts (FIG. 3A-FIG. 3C). Dermal $CD14^+$ DCs as well as dermal $CD1a^{(dim)}CD141^+$ served as a control and were the weakest stimuli for proliferation (FIG. 3 A-FIG. 3C).

Figure 3D:
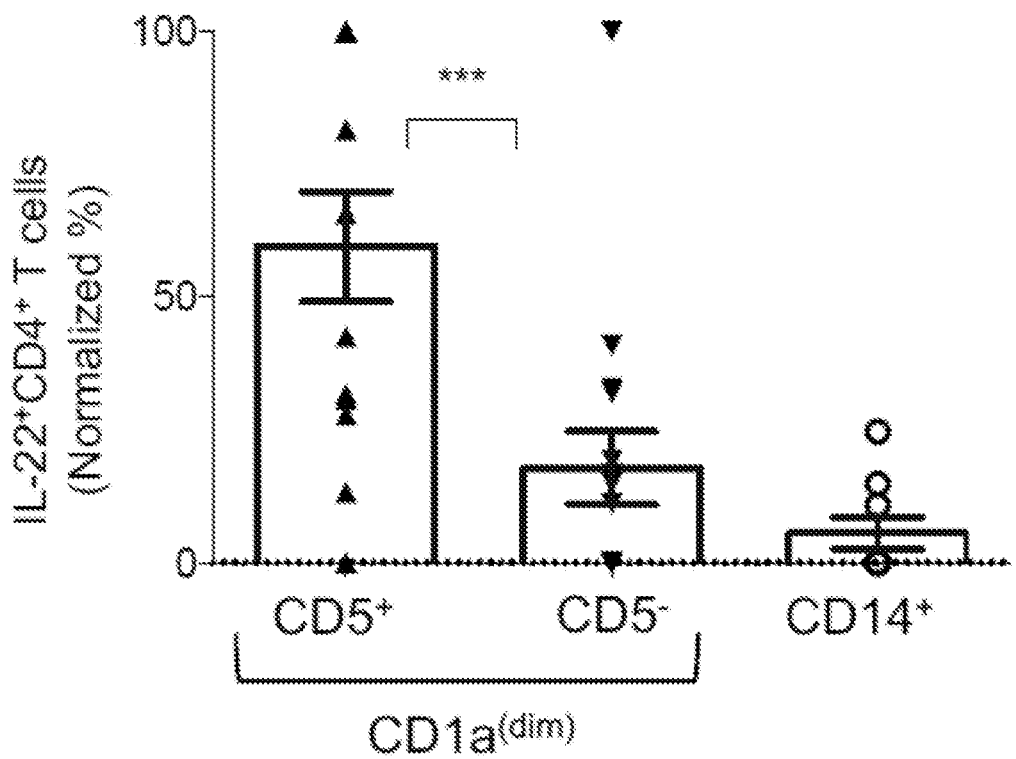
Figure 3E:
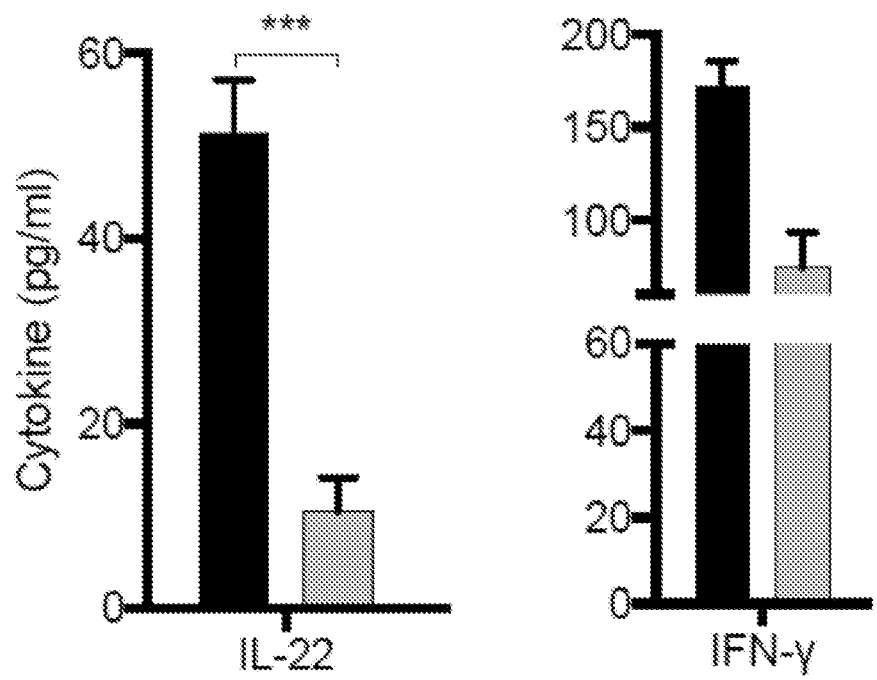

Subsequently, the capacity of DCs to polarize $CD4^+$ T cells was examined by measuring their cytokine production. Dermal $CD5^+$ DCs induced a significant difference in the proportion of polarized IL-22-expressing T cells ($p<0.05$) when compared to $CD5^-$ DCs or those primed by $CD14^+$ DCs, as detected by intracellular cytokine staining (FIG. 3C-FIG. 3D). In addition, the amount of IL-22 produced by each T cell was higher in those primed by dermal $CD5^+$ DCs compared to those primed by dermal $CD5^-$ DCs (FIG. 3E; left). Although both $CD5^+$ and $CD5^-$ DCs could polarize IFN-γ-producing $CD4^+$ T cells, $CD5^+$ DCs were more efficient in this process (FIG. 3E; right). Thus, dermal $CD5^+$ DCs are more efficient than $CD5^-$ DCs in inducing the proliferation and polarization of naïve $CD4^+$ T cells into IFN-γ and IL-22 cytokine-secreting cells.

Functional Analysis of $CD5^+$ and $CD5^-$ LCs

Figure 4A:
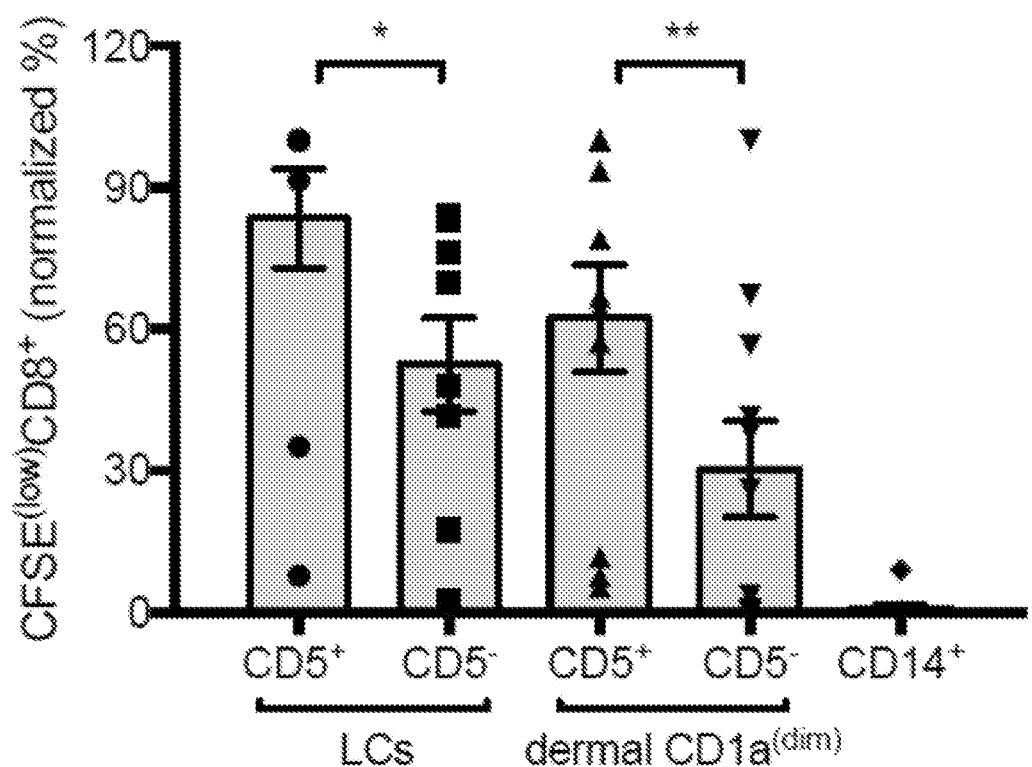
FIG. 4A-FIG. 4G is a series of graphs and plots showing the functional characterization of CD5$^+$ and CD5$^-$ LC subsets.
Figure 4B:
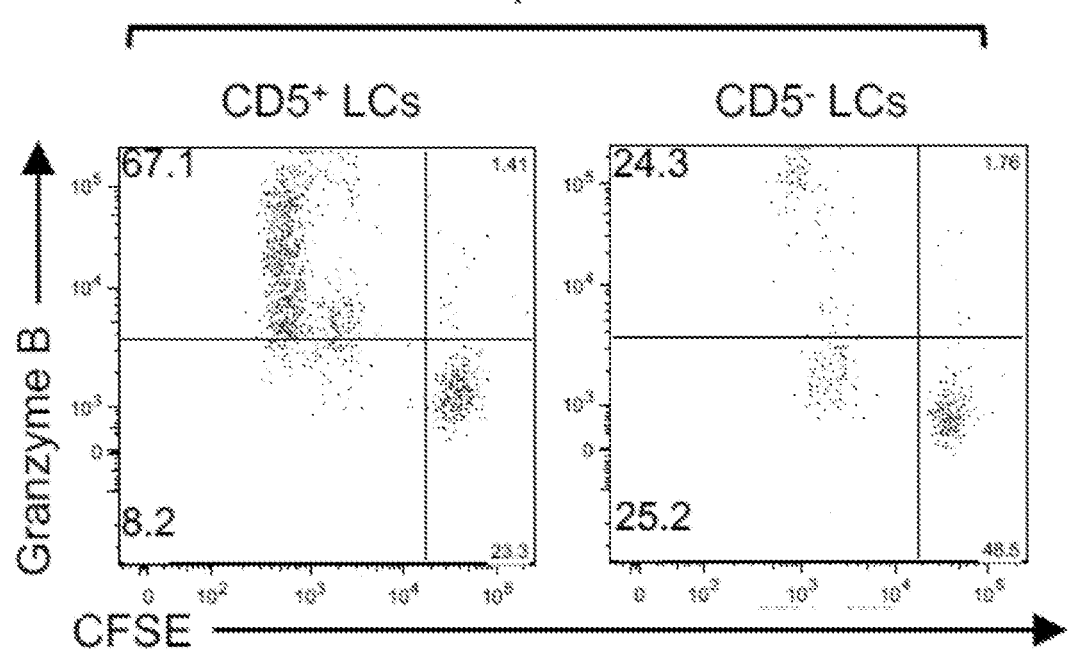
Figure 4C:
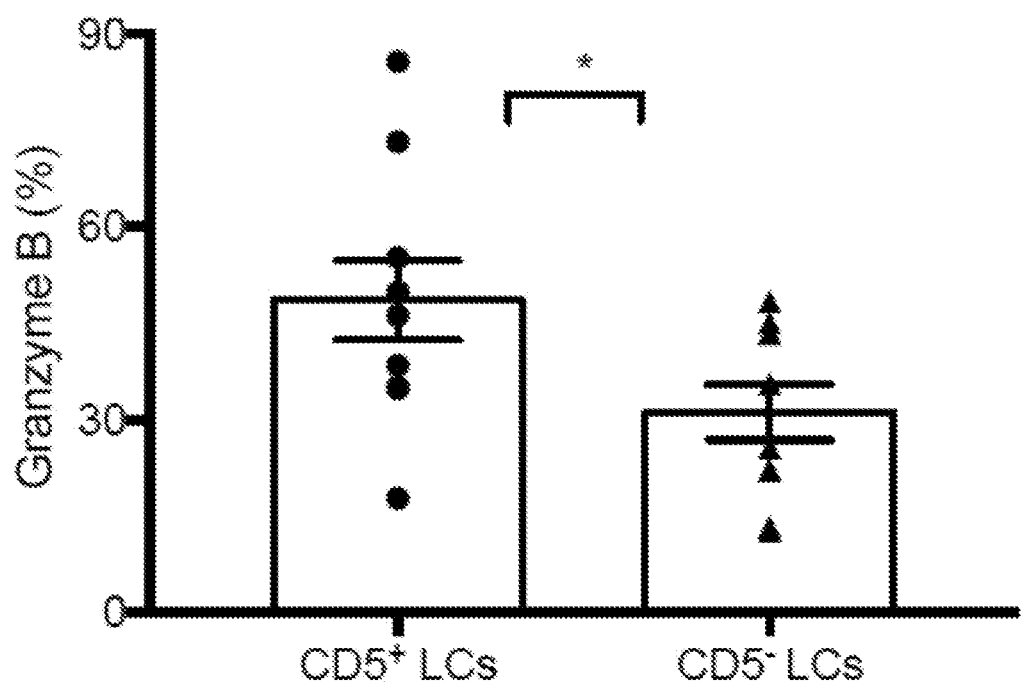
Figure 4D:
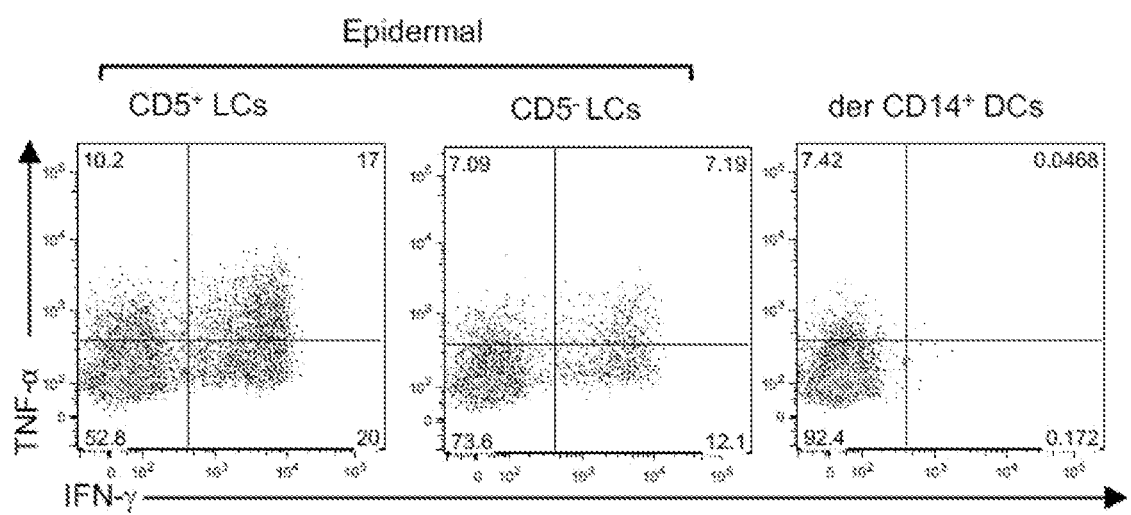
Figure 4E:
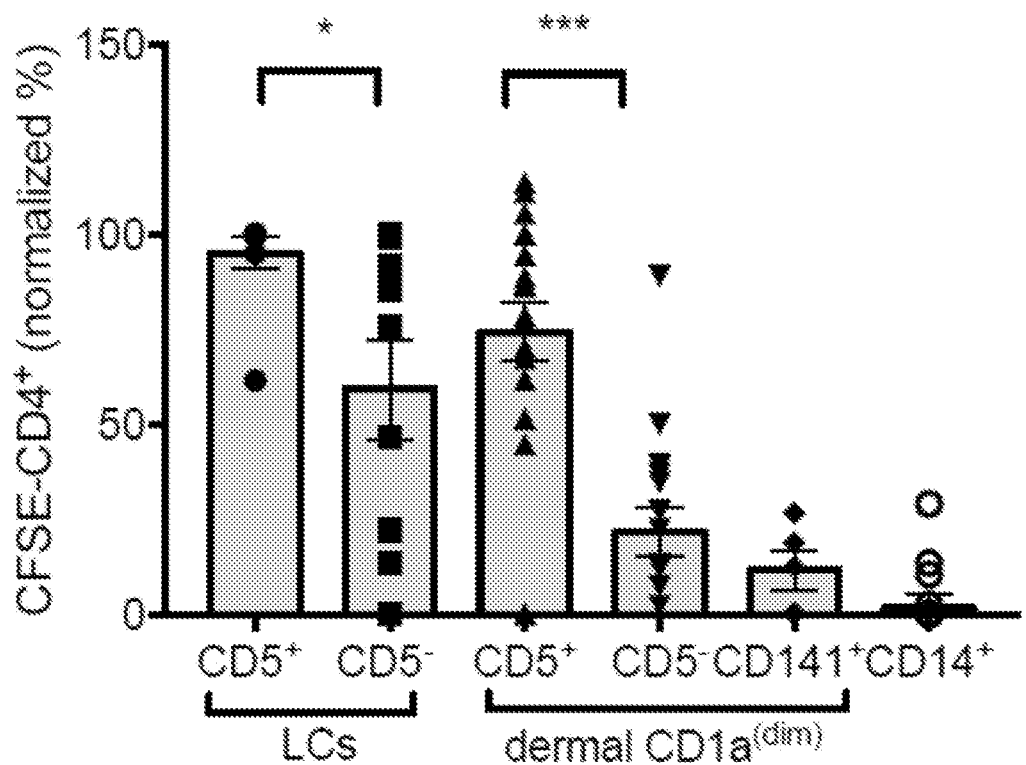
Figure 4F:
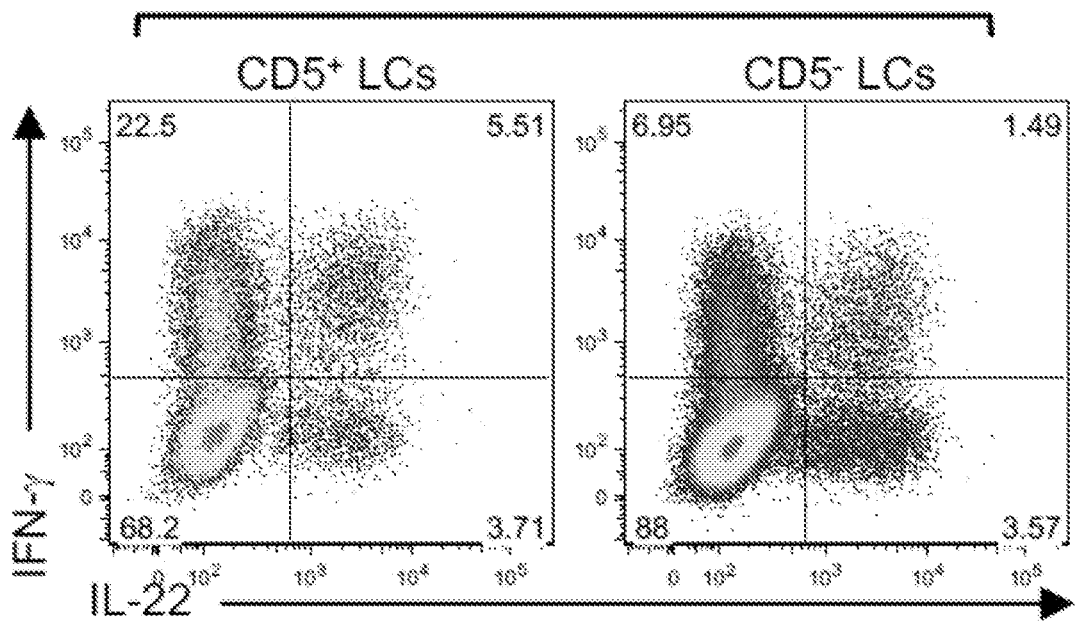
Figure 4G:
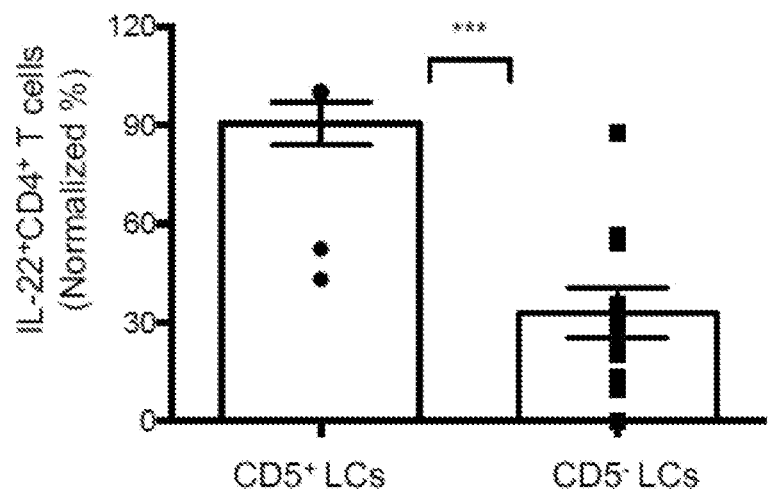

Because we also found CD5-expressing cells within the epidermis, we assessed their capacity to activate allogeneic naïve $CD8^+$ and $CD4^+$ T cell responses. Sorted live HLA-$DR^+CD1a^{(hi)}$ $CD5^+$ and $CD5^-$ LCs were co-cultured with allogeneic naïve T cells and analyzed after seven days for T cell proliferation. As shown in FIG. 4A, we found that both LC subsets were more efficient than the dermal subsets at inducing allogeneic $CD8^+$ T cell proliferation. Interestingly, while the percentage of cells that diluted CFSE in response to the two LC subsets was relatively close (FIG. 4A). The number of Granzyme B-producing primed $CD8^+$ T cells (FIG. 4B and FIG. 4C), as well as the number of multifunctional IFN-α and TNF-α-producing $CD8^+$ T cells (FIG. 4D) was higher in cultures primed by the $CD5^+$ LCs compared to the $CD5^-$ LCs. However, the amounts of IFN-γ produced per cell was similar between the two LC subsets (data not shown). Similar to the $CD8^+$ T cell responses, we found that both LC subsets were more efficient than the dermal subsets at inducing allogeneic $CD4^+$ T cell proliferation and that the number of primed $CD4^+$ T cells that produced IL-22 was higher when the cells were primed by $CD5^+$ LCs compared to those primed by $CD5^-$ LCs (FIG. 4E-FIG. 4F). In addition, the amount of IL-22 produced by each T cell was higher in those primed by $CD5^+$ LCs compared to those primed by $CD5^-$ LCs (FIG. 4G) Overall, CD5 expression on LCs further potentiate their capacity to prime CTLs and Th22 cells.

$CD5^+$ DCs are Enriched in the Epidermis and the Dermis of Psoriasis Patients

Figure 5A:
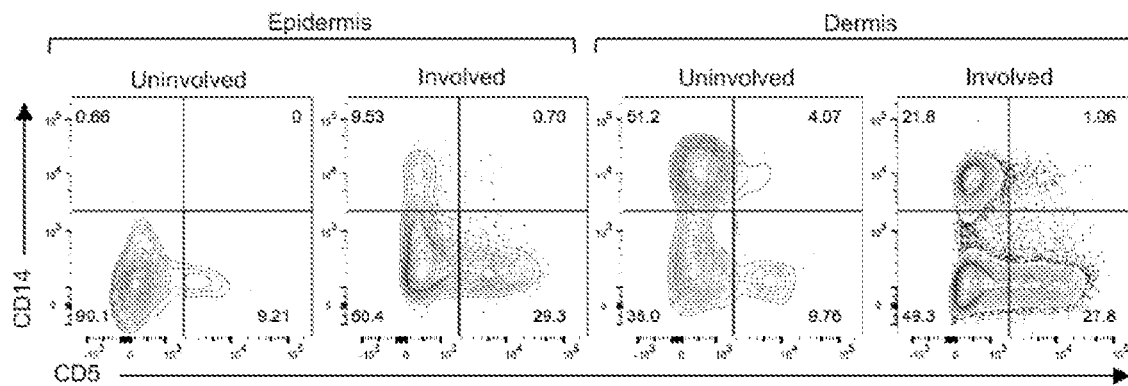
FIG. 5A-FIG. 5D is a series of plots, graphs, and images showing CD5$^+$ LCs and dermal DCs are increased in involved psoriatic skin plaques compared to non-lesional psoriatic skin.
Figure 5B:
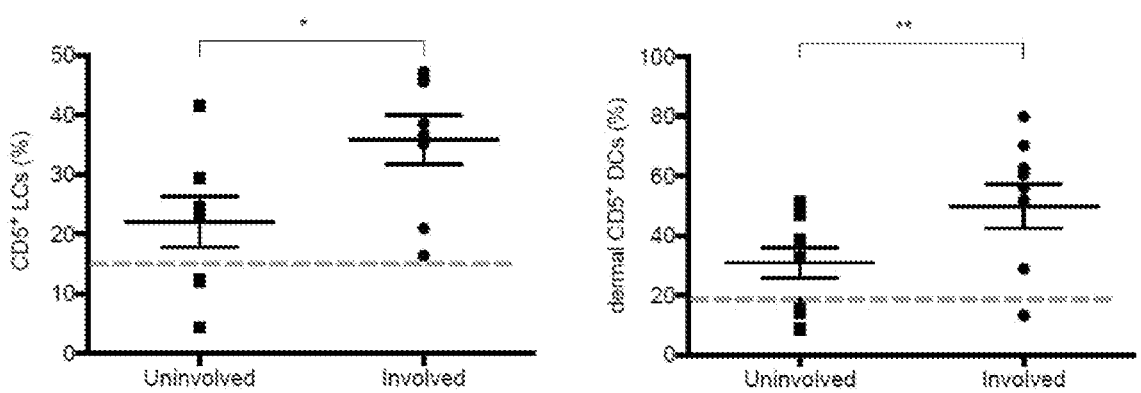
Figure 5C:
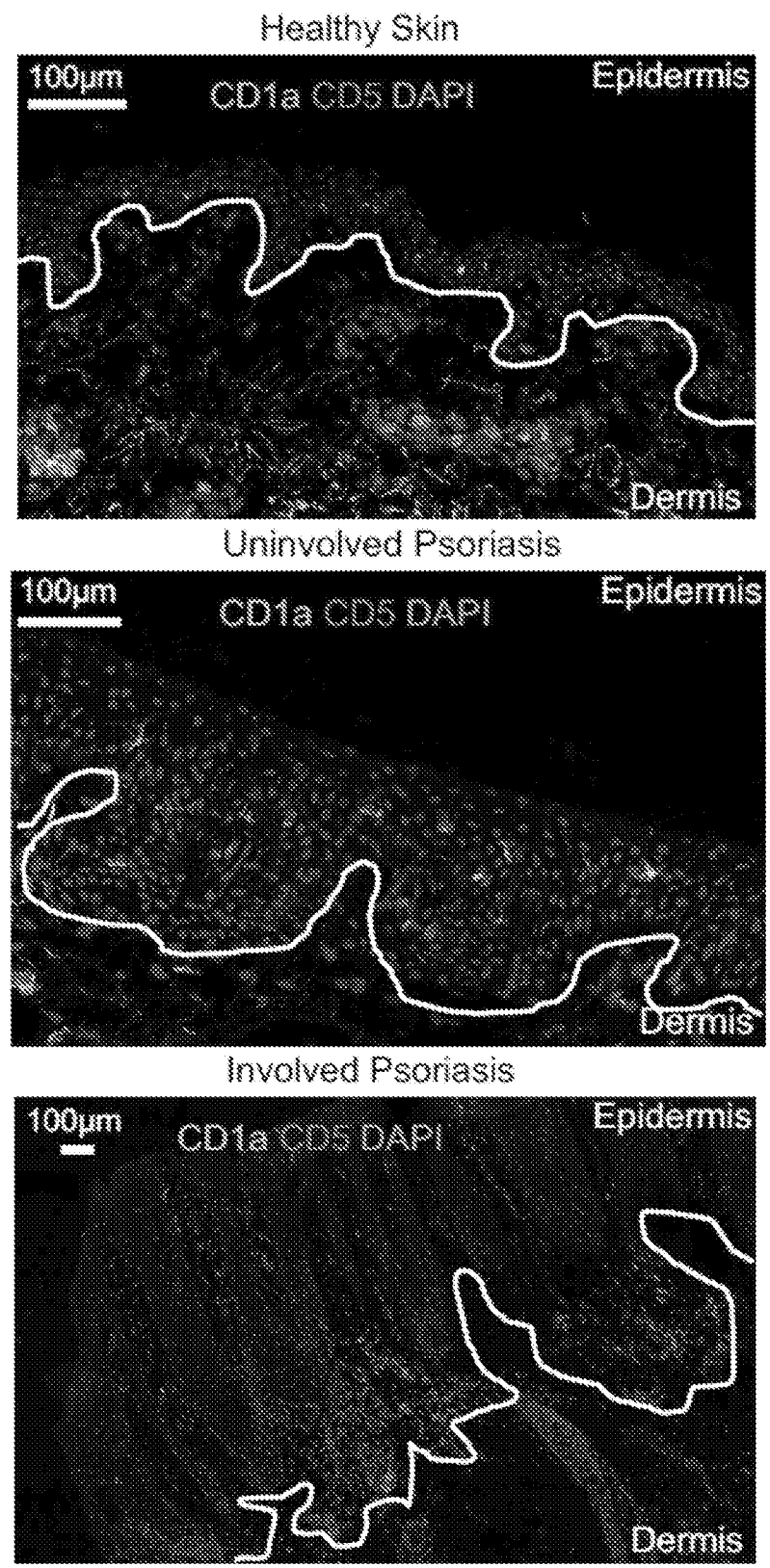
Figure 5D:
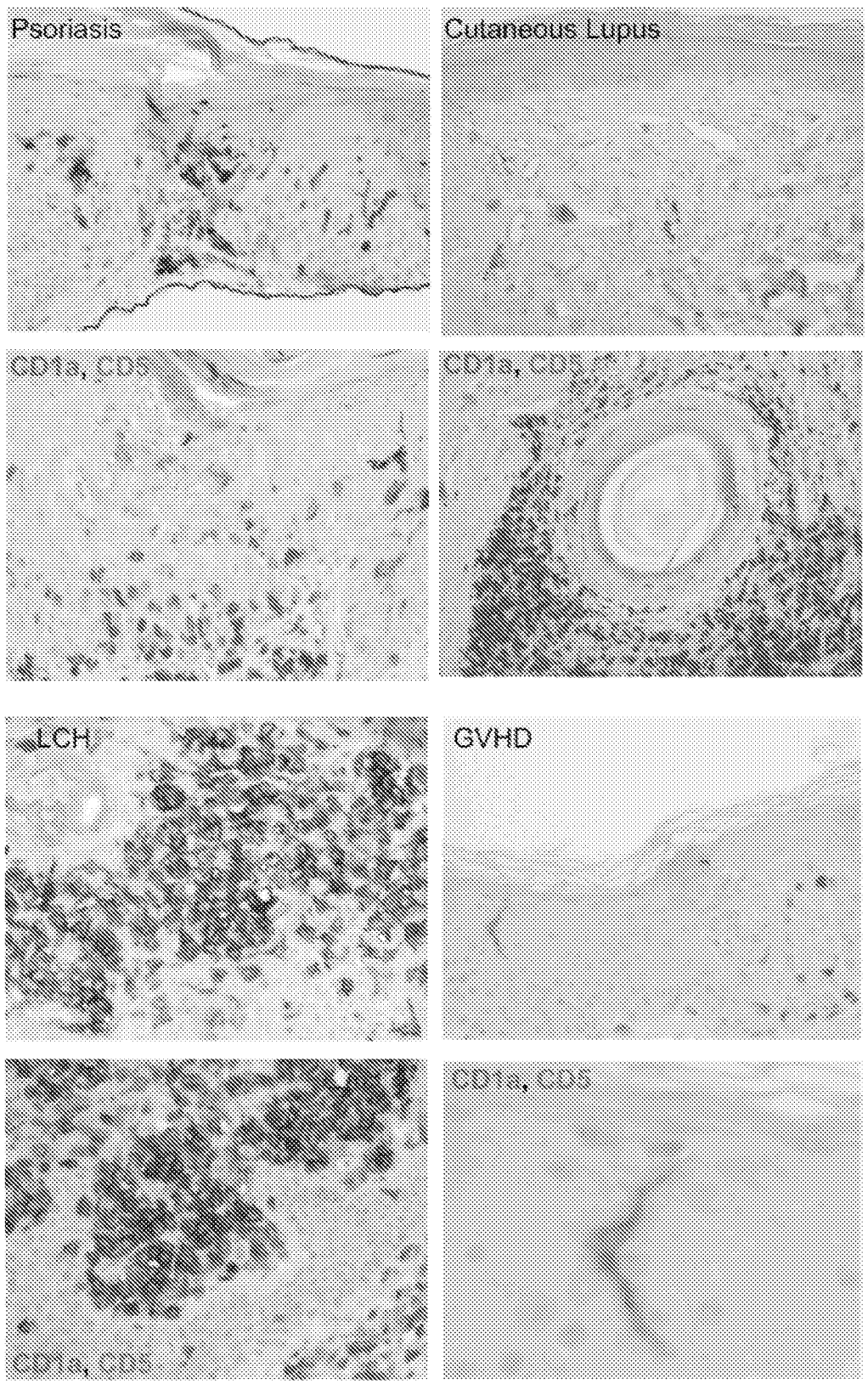
Figure 11:
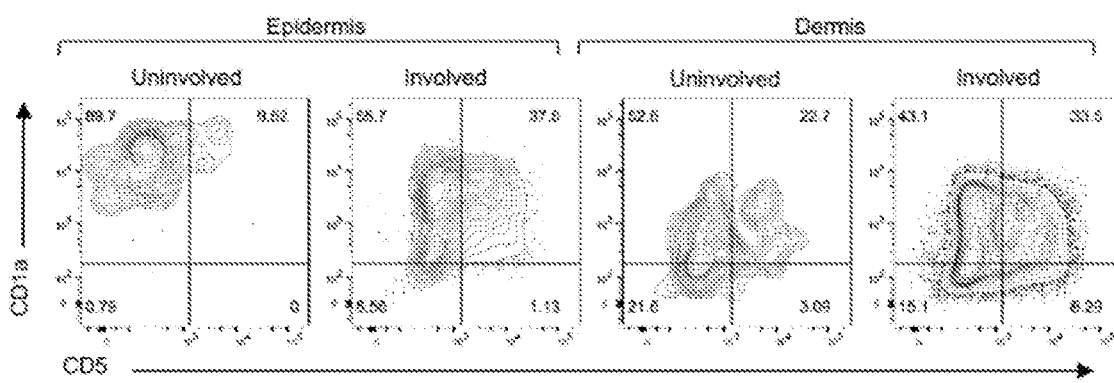
FIG. 11 is a series of plots showing the expression of CD1a and CD5 in involved and uninvolved psoriatic plaques. CD5 expression on epidermal and dermal DCs isolated from involved (left forearm) and uninvolved (left arm) lesions of psoriasis patient's 025 (see TABLE 1) skin. Graphs show the expression of CD1a and CD5 on the gated live HLA-DR$^+$CD3/19$^-$ DCs.
Figure 12:
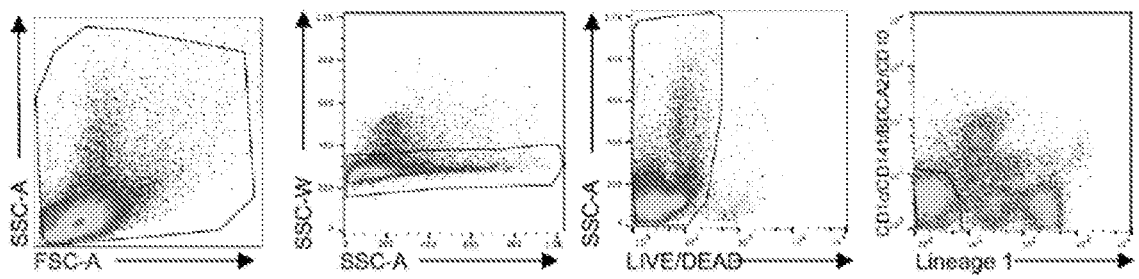
FIG. 12 shows the gating strategy for purifying cord blood and dermal DC progenitors. Progenitors were sorted after gating on the Lin$^{neg}$(CD3$^-$CD19$^-$CD56$^-$CD14$^-$CD66b$^-$) DC$^{neg}$(CD1c, BDCA2, CD141)$^-$CD10$^-$ cells.

Given the ability of skin $CD5^+$ DCs to activate Th1 and Th22 cells, the hallmark of psoriasis pathogenesis, we hypothesized that the CD5-expressing DCs might promote disease. Skin biopsies were obtained from involved psoriatic plaques and adjacent non-lesional skin from patients with psoriasis. Dermal and epidermal DCs were purified in a similar manner to that done with healthy skin and analyzed by multicolor flow cytometry. The percentage of $CD5^+$ DCs in both the dermis and the epidermis was found to be two-fold higher in the psoriatic skin plaque as compared to the non-lesional skin in all patients examined. Interestingly, the uninvolved lesions presented with higher amounts of $CD5^+$ DCs compared to healthy skin, by an average of 1.6 times, (FIG. 5A and FIG. 5B and FIG. 1B). The $CD5^+$ DCs seen in the epidermis expressed lower amounts of CD1a (FIG. 11), suggesting that they might be newly differentiated bone marrow cells that migrated to the epidermis or dermal DCs that migrated to the epidermis. Increased numbers of $CD5^+$ DCs were also observed in the epidermis and dermis in situ, using tissue immuno-staining (FIG. 5C and FIG. 5D). This phenomenon was not observed in cutaneous lupus or Langerhans cell histocytosis. However, $CD5^+$ LCs were strikingly the only detected cell type in the skin of graft-versus-host patient (FIG. 5D), suggesting their contribution to this inflammatory skin condition and consistent with the greater capacity of the $CD5^+$ DCs to induce allogeneic T cell responses (FIG. 4A and FIG. 4E). Overall, our data suggest that $CD5^+$ DCs could play a key role in the pathogenesis of psoriasis by promoting IFN-γ and IL-22-mediated T cell responses.

$CD34^+$ Hematopoietic Progenitors Give Rise to $CD1c^+$ $CD5^+$ DCs

Figure 6A:
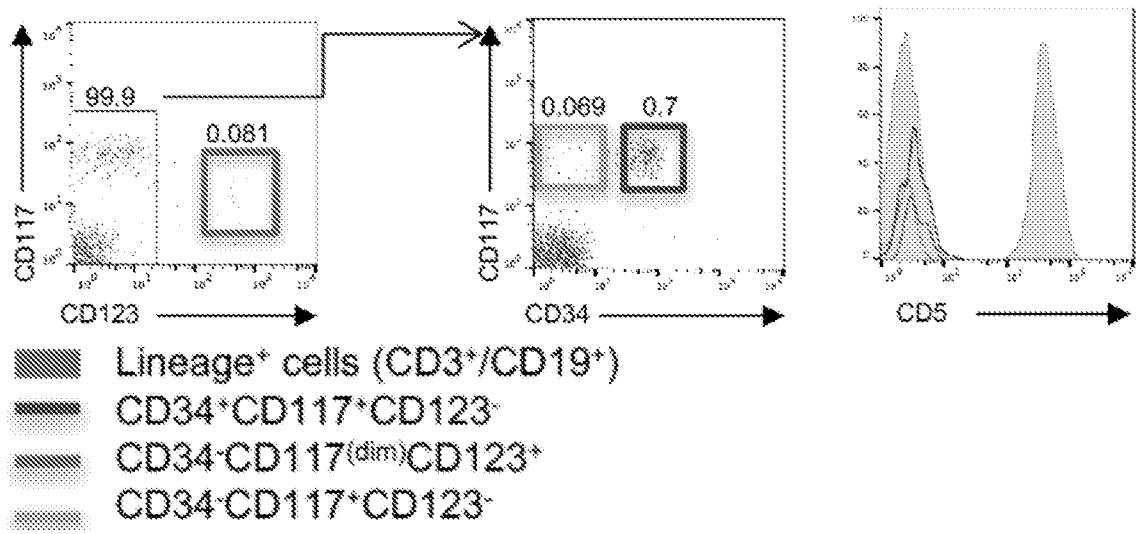
FIG. 6A-FIG. 6J is a series of plots and graphs showing CD5 marks a functional terminally differentiated DC subset.
Figure 6B:
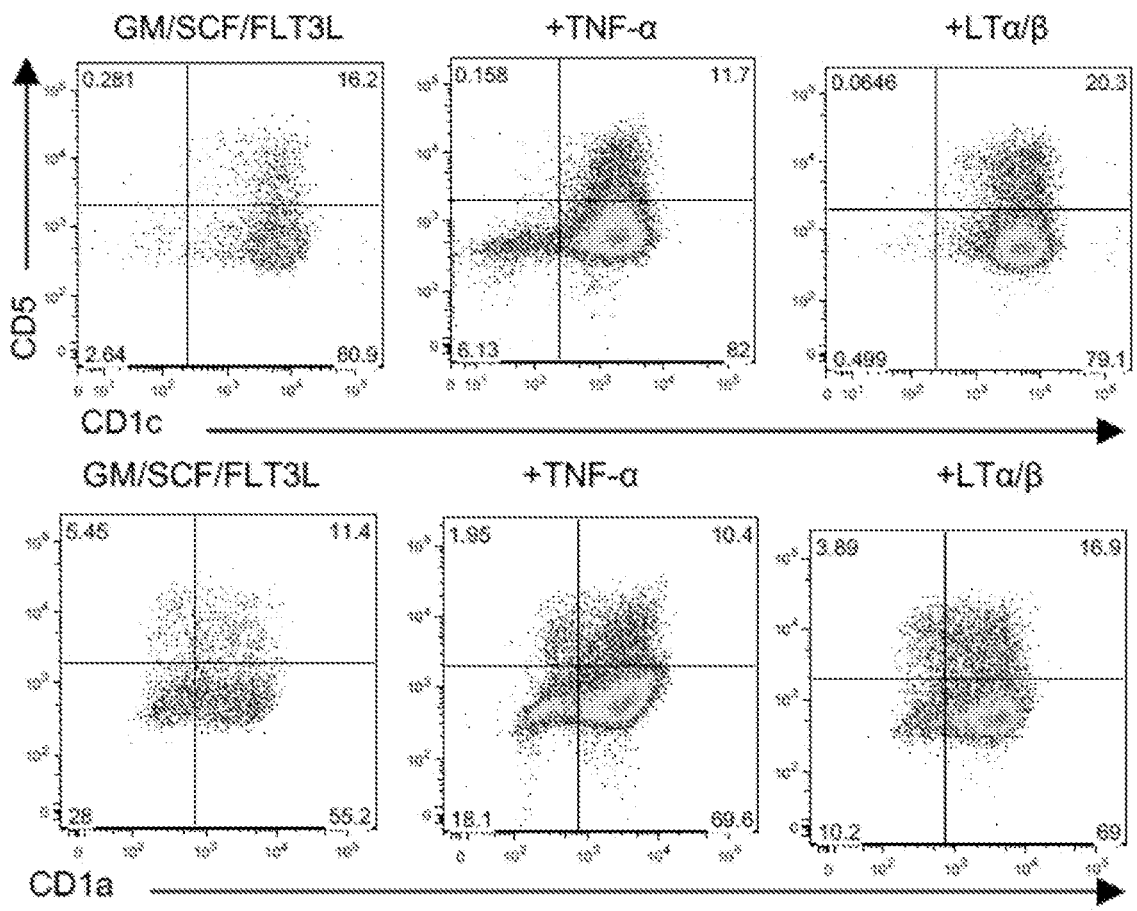
Figure 6C:
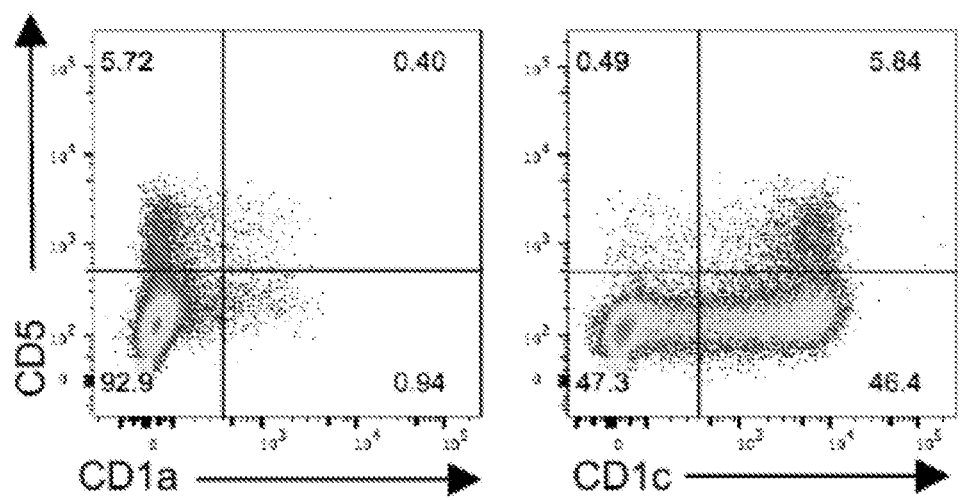
Figure 6D:
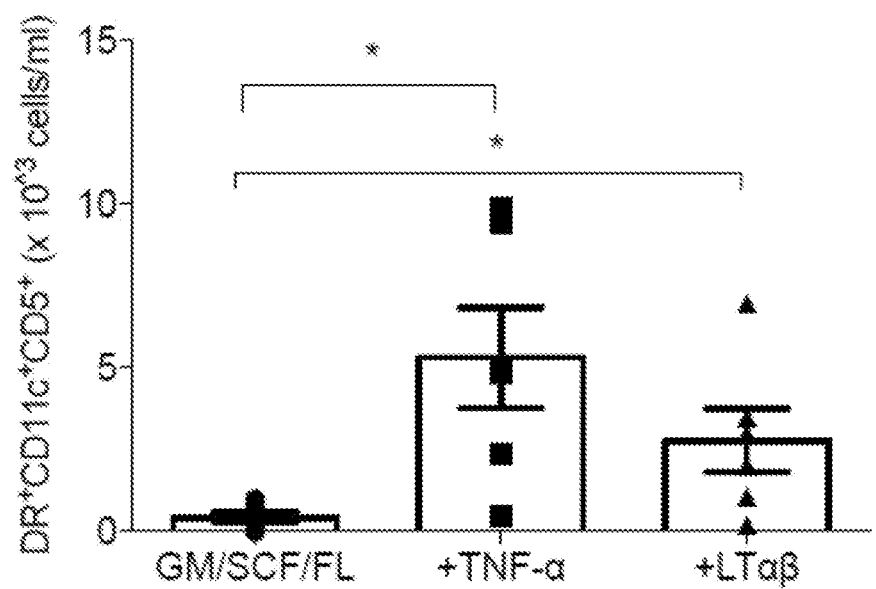
Figure 6E:
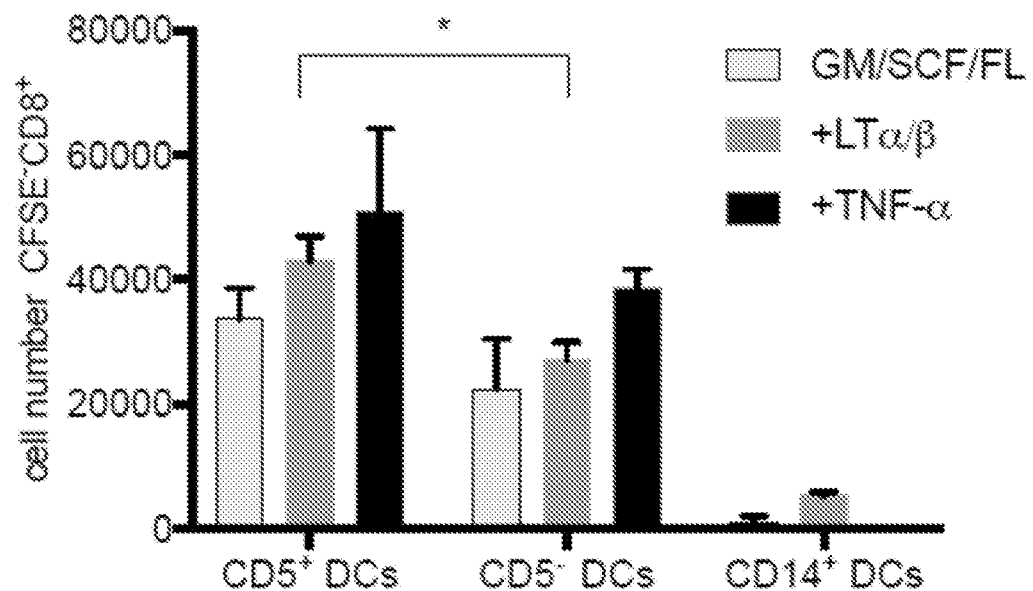
Figure 6F:
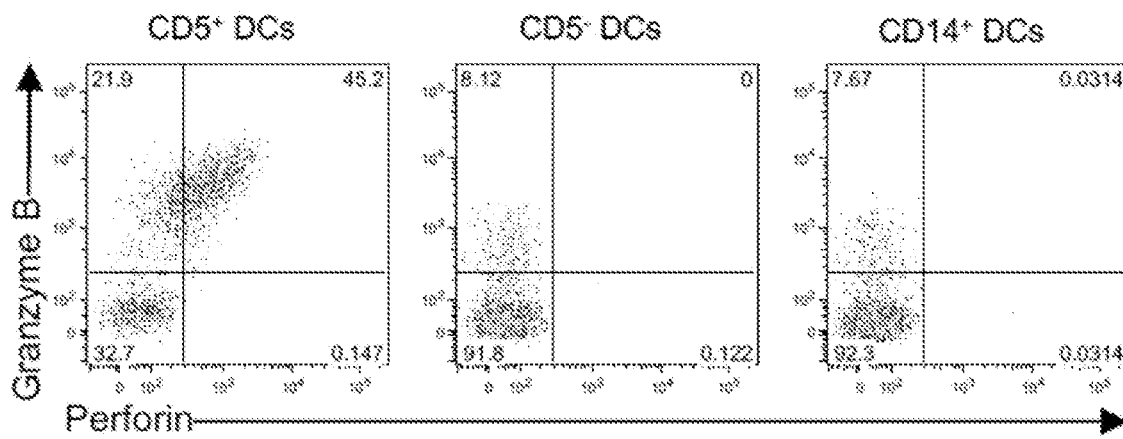
Figure 6G:
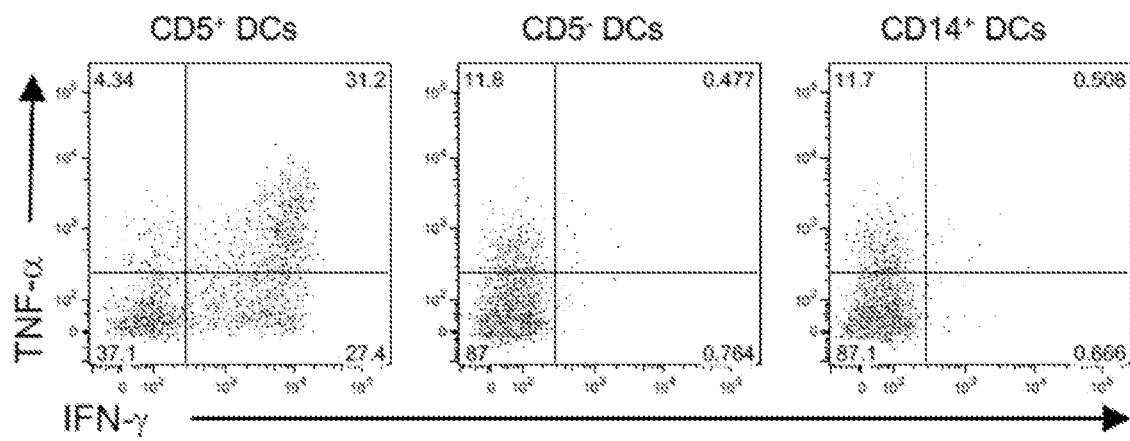
Figure 6H:
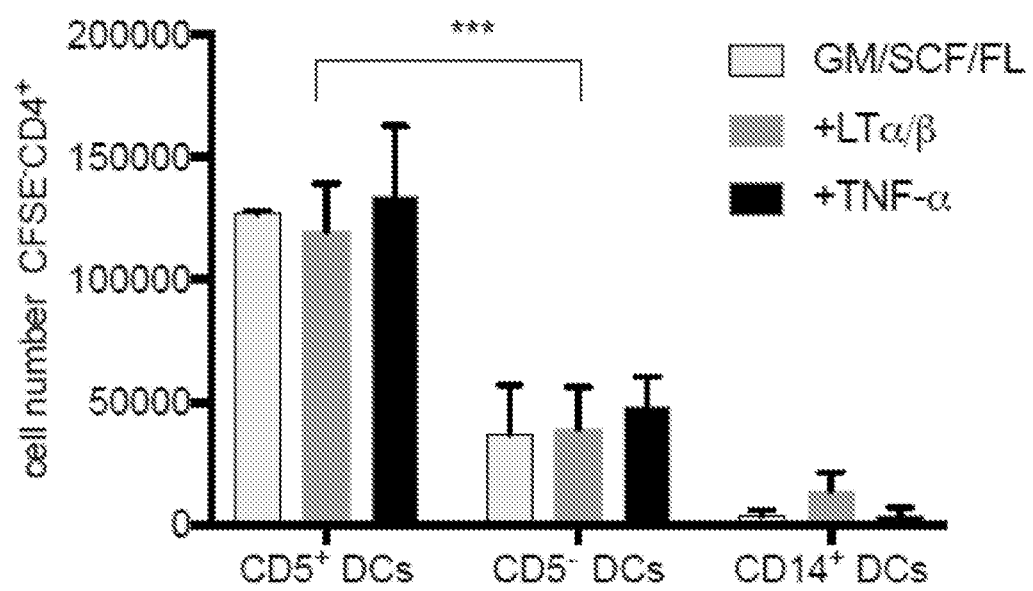
Figure 6I:
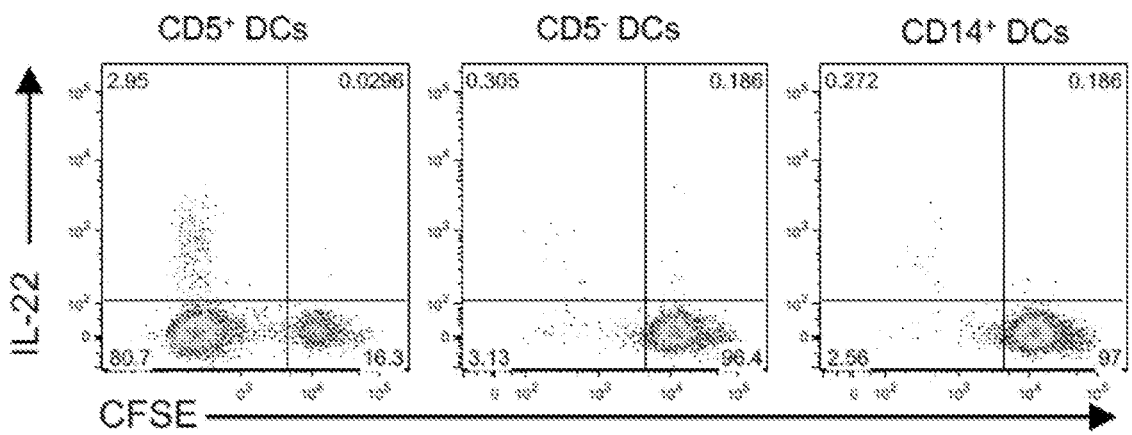
Figure 6J:
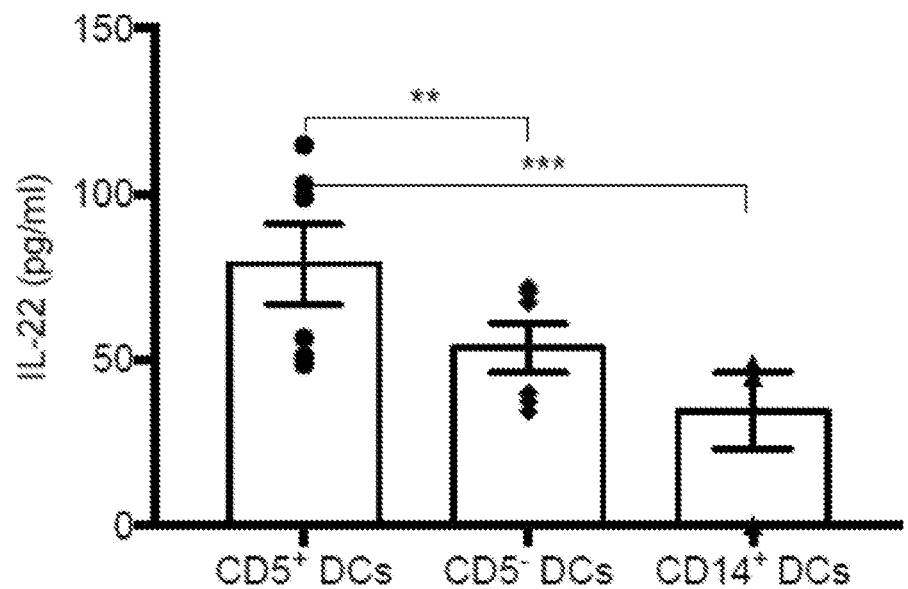

To define the developmental relationship between the $CD5^+$ and the $CD5^-$ subset, $CD34^+CD117^+$ Hematopoietic progenitor cells (HPCs) from cord blood were differentiated into DCs on the mouse stromal cell line, MS-5, and in the presence of the cytokines FLT3-Ligand (FLT3-L), GM-CSF, and stem cell factor (SCF), as previously described (Breton et al., 2015a). The expression of CD5 during DC differentiation was followed for several days. CD5 was not expressed on cord blood HPCs (FIG. 6A). However, after five days of culture we could clearly detect CD5 expression on $CD1c^+CD1a^+$ and $CD1c^+CD1a^-$ DCs (not shown), with CD5 expression further expanded by day seven (FIG. 6B). These results are consistent with the characterization of skin DCs, where the $CD5^+$ DCs branch out as a subset of the $CD1c^+CD1a^{(hi)}$ DCs in the epidermis (LCs) and $CD1c^+$ $CD1a^{(dim)}$ in the dermis (Klechevsky et al., 2008) (FIG. 1A and FIG. 10A). CD11b expression was shared between the in-vitro $CD5^+$ DCs and dermal $CD5^+$ DCs. In addition to sharing the expression of CD1c and CD1a, we found that both in vitro and ex vivo $CD5^+$ DCs lacked CD103 and Sirp-α, CLA, CX3CR1, CD40, CD123 and BDCA-2 (not shown). Langerin was only expressed on a small fraction of the in-vitro $CD1a^+$ DCs and by LCs. In-vitro $CD5^+$ DCs expressed lower levels of the activation markers CD83, CD86 and CCR7 than skin DCs, but higher than the levels expressed by blood $CD5^+$ DCs. (FIG. 1D). Functionally, like the skin $CD5^+$ DCs, in-vitro $CD5^+$ DCs were also more efficient than the $CD5^-$ DCs or $CD14^+$ DCs at inducing the proliferation of allogeneic $CD8^+$ T cells (FIG. 6E) and priming into effector CTLs that produced granzyme B and perforin (FIG. 6F), as well as IFN-γ and TNF-α (FIG. 6G). Moreover, CD5+ DCs that differentiated from CD34+ HPCs were more efficient than the CD5− DCs or CD14+ DCs at inducing the proliferation of allogeneic CD4+ T cells (FIG. 6H and FIG. 6I) and their priming into IL-22-producing cells (FIG. 6I). In addition, the amount of IL-22 produced by each T cell was higher in those primed by in vitro CD5+ DCs compared to those primed by in vitro CD5− DCs (FIG. 6J) Thus, CD5+ DCs develop from BM independently of the CD5− fraction and resemble their ex-vivo counterparts.

TNF-Signaling Enhances the Development of CD5+ DCs from CD34+ Hematopoietic Progenitors Next, we assessed whether the differentiation state of the CD1c+CD5+ DCs is dependent on certain cytokine signals. Purified CD34+CD117+ HPCs from cord blood were cultured with either one or a combination of the cytokines GM-CSF, FLT3-L, and SCF, as described (Breton et al., 2015a; Breton et al., 2015b; Klechevsky et al., 2008; Lee et al., 2015). We found that FLT3-L and SCF were sufficient to induce the differentiation of the CD5+ DCs from CD34+ HPCs (FIG. 6C). Next, we assessed whether the differentiation of CD5+ DCs would be altered in the presence of cytokines that are abundant in inflamed psoriatic skin such as TNF-α and Lymphotoxin α/β (LTα/β). Indeed, we found that addition of TNF-α or LTα/β to FLT3-L, GM-CSF and SCF, promoted the differentiation of the CD11c+CD1c+CD5+ DCs (FIG. 6B and FIG. 6D). The number of CD5+ DCs measured on day seven increased from (mean±S.D.) $0.419 \times 10^3 \pm 0.4$ cells/mL with FLT3-L, GM-CSF and SCF to $5.309 \times 10^3 \pm 3.7$ cells/mL with addition of TNF-α and to $2.78 \times 10^3 \pm 0.4$ cells/mL with the addition of LTα/β (FIG. 6D). The ability of the CD5+ DCs to expand allogeneic CD4+ and CD8+ T cells was higher than the one of the CD5− DCs and CD14+ DCs even when the cells were cultured in the presence of TNF-α or LT α/β. Overall, CD5+ DCs branch out from the CD1c+ DCs and their differentiation potential is enhanced by TNF-α signaling, including TNF-α and LTα/β.

CD34−CD123+CD117$^{(dim)}$Cells are an Immediate Precursor to Human CD5+ DCs

Figure 7A:
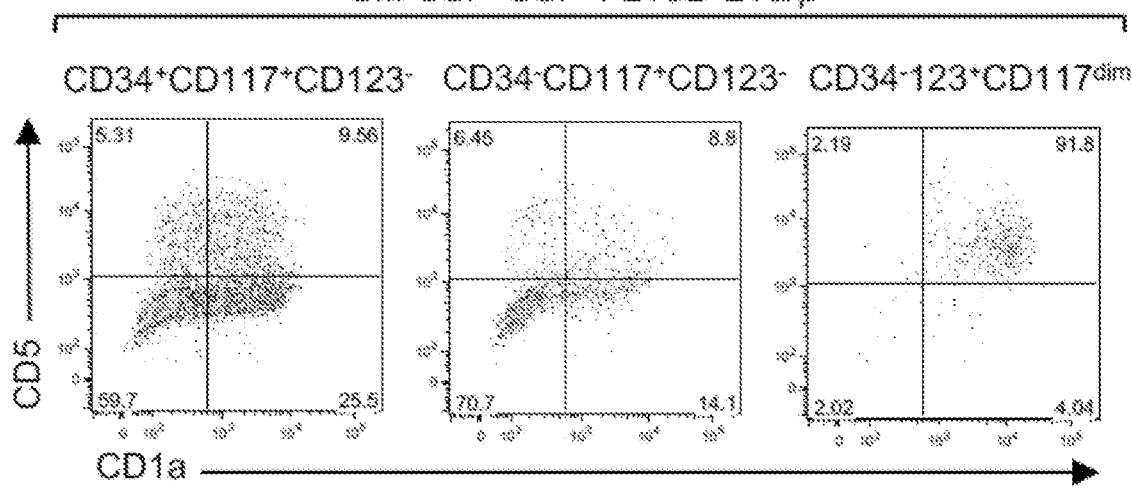
FIG. 7A-FIG. 7B is a series of plots and graphs showing CD34$^-$ CD123$^+$CD117$^{(dim)}$ cells preferentially give rise to the CD5$^+$ DCs.

The fact that only a fraction of CD34+ HPCs differentiated into the CD5+DCs led us to hypothesize that a committed progenitor for CD5+ DCs might exist in the BM. Thus, we assessed whether CD5+ DCs would differentiate from the recently identified pre-cDC CD34− progenitors (Breton et al., 2015b; Lee et al., 2015). Progenitors were sorted from cord blood as Lineage (CD3/19/56/14/66b)− DC(CD1c/141/303)−CD10−: CD34+CD117+CD123− (GMDPs/MDPs) or CD34−CD117+CD123− (pre-cDC) (FIG. 6A) and cultured for seven days on MS-5 cells with GM-CSF, SCF, FLT3-L and LTα/β. Indeed, both CD11c+CD1a+CD5+ and the CD11c+CD1a+CD5− DCs differentiated from the CD34+CD117+ or the CD34−CD117+ DC progenitors (FIG. 7A). We noticed a third progenitor population within the CD34− Lineage (CD3/19/56/14/66b)− DC(CD1c/141/303)−CD10− population which was marked by CD123+ and low levels of CD117 (FIG. 6A; red). Surprisingly, we found that under similar culture conditions, these cells preferentially differentiated into CD11c+CD1a+CD5+ DCs expressing CD5 (FIG. 7A). Thus, the high clonal efficiency and differentiation potential of the CD34− 123+ progenitor cell suggests that it could represent a committed progenitor for the CD5+ DCs.

Figure 7B:
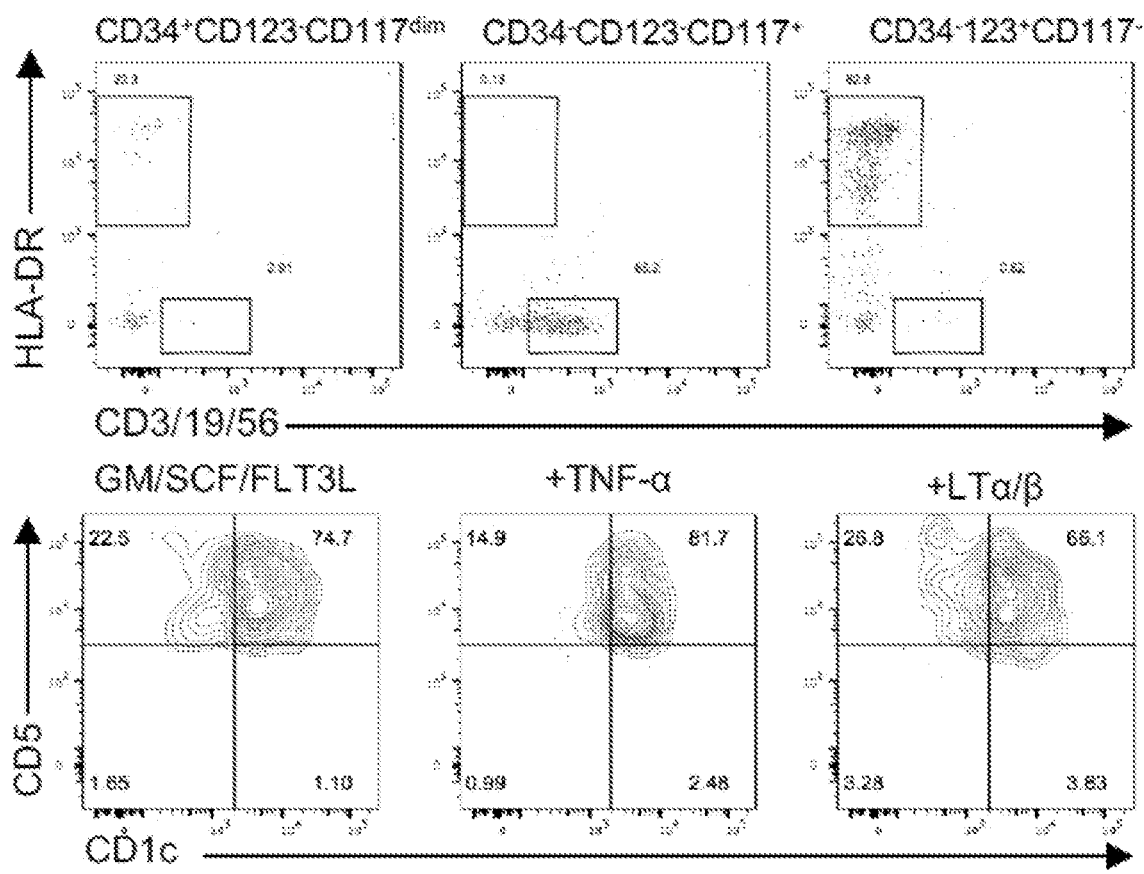

CD34−CD123+CD117$^{(dim)}$Progenitors are Found in Human Dermis and Give Rise to CD5+ DCs We next assessed whether this unique progenitor population can also be found in skin. Thus, cells were isolated from epidermis and dermis of human skin and analyzed for the presence of progenitors in a similar manner to the cord blood within the Lineage (CD3/19/56/14/66b)− DC(CD1c/141/303)−CD10− population. The CD34+ cells could only be found in the dermis and not the epidermis. However, in contrast with cord blood, dermal CD34+ cells expressed intermediate levels of CD117. We next analyzed the cells within the CD34− fraction and found a population that expressed CD117$^{(hi)}$ that lacked CD123, and one marked by CD123 but lacked CD117. Sorted progenitors were cultured on mouse stromal cells as done with the cord blood progenitors in the presence of cytokines for seven days. As shown in FIG. 7B, the CD34+CD117$^{(dim)}$ HPCs gave rise to 20% HLA-DR+ cells and 2% lymphoid cells (CD3/CD19/CD56), the CD34−| CD123−CD117+ gave rise primarily to lymphoid cells (85.2% of CD3/CD19/CD56+| cells). The CD34−CD123+CD117$^{(dim)}$ HPCs gave rise primarily to HLA-DR+ cells (82.6%), and most of these cells expressed CD1c and CD5 (FIG. 7C). The differentiation of the CD1c+CD5+ DCs occurred in the presence or absence of LTα/β or TNF-α (FIG. 7C). Thus, a progenitor for the CD1c+CD5+ DCs is present in human dermis.

Figure 8A:
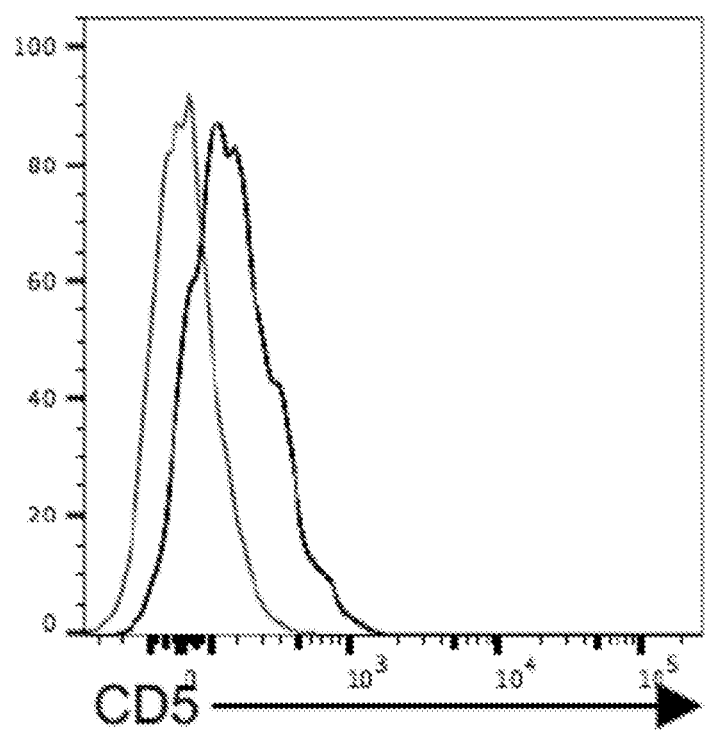
FIG. 8A-FIG. 8E is a series of plots and graphs showing CD5 signals DCs to produce pro-inflammatory cytokines.
Figure 8B:
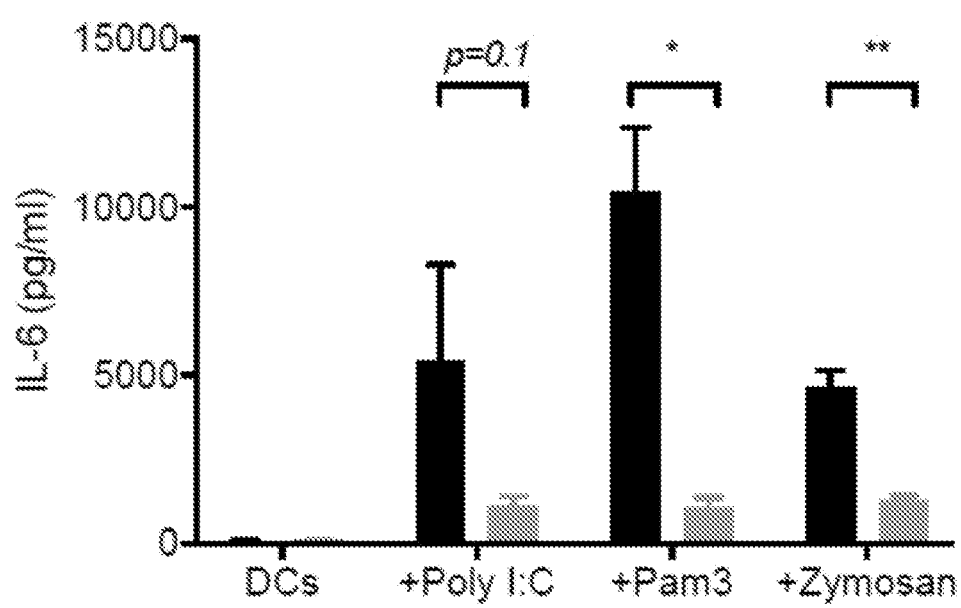
Figure 8C:
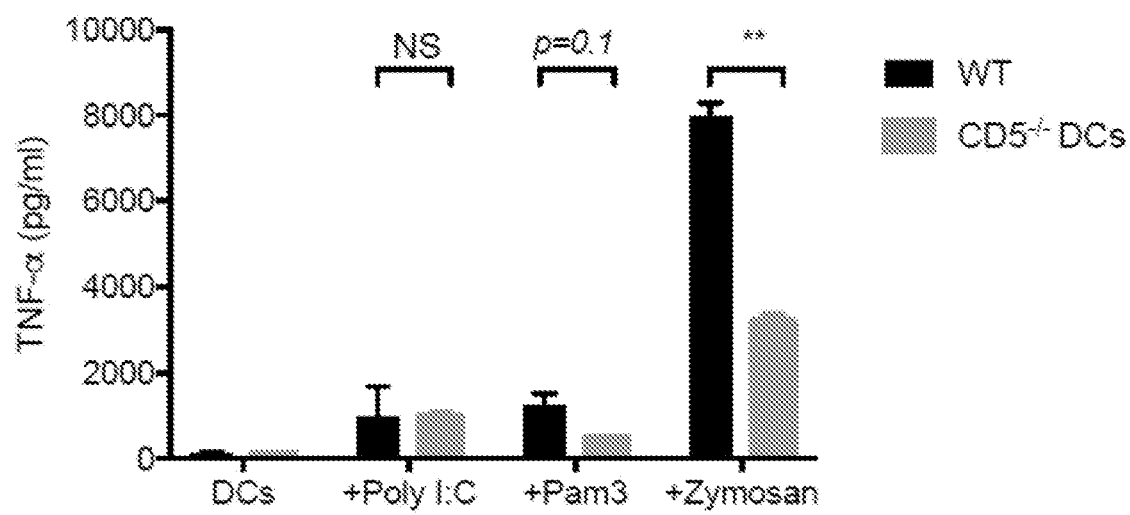
Figure 8D:
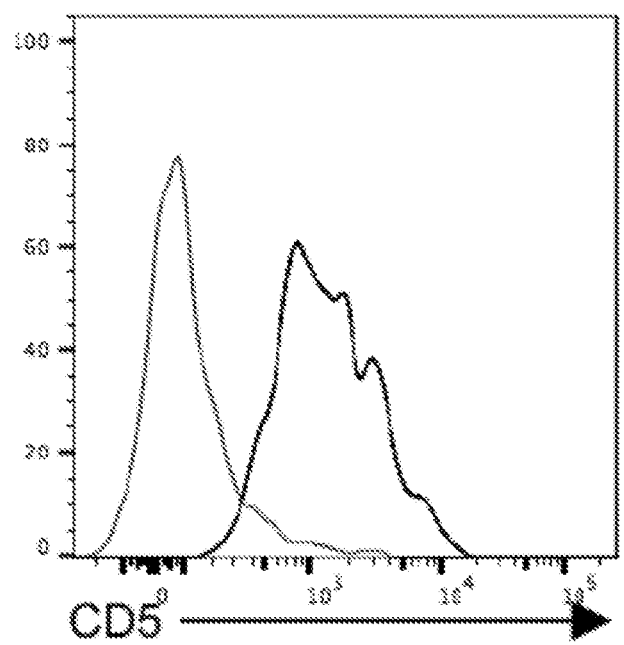
Figure 8E:
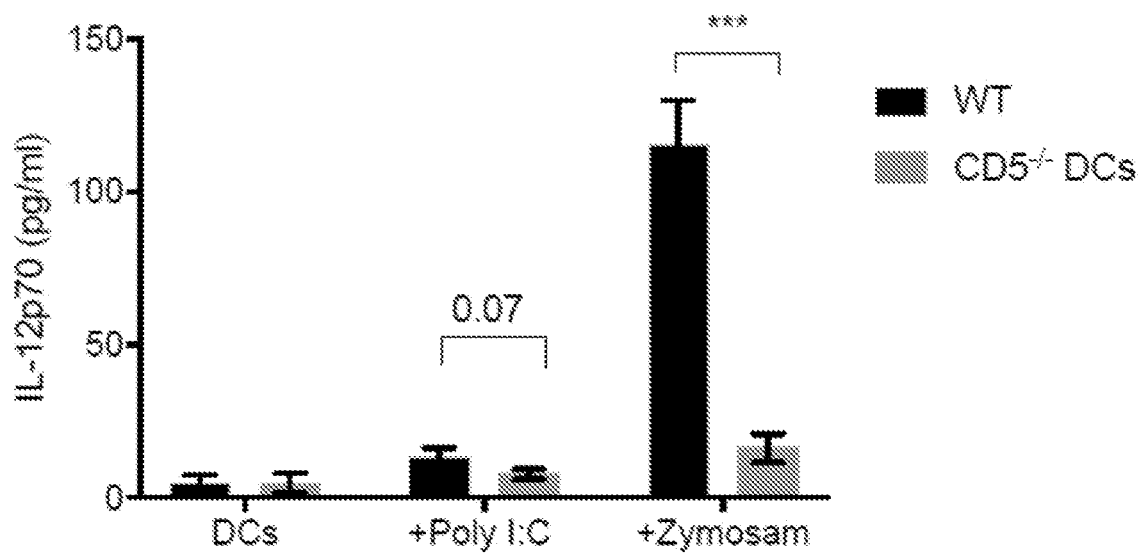

CD5 Expression on DCs is Important for their Production of Pro-Inflammatory Cytokines To understand the role of CD5 on DCs, we differentiated DCs from BM of either wild type or CD5−/− mice using FLT3-L (FIG. 8A). DCs were harvested and activated with either zymosan, Pam3 or Poly I:C. The levels of cytokines were measured in the culture supernatant after 24 hours. We found that CD5−/− DCs produced substantially lower levels of IL-6 (FIG. 8B) and TNF-α (FIG. 8C) compared to WT DCs in response to zymosan. WT DCs that were activated with Pam3 produced higher amounts of IL-6 compared to CD5−/− DCs (FIG. 8B). To further confirm this observation, we used an alternative method to generate DCs in vitro using GM-CSF and FLT3-L (FIG. 8D). These cultures yielded CD103-like DCs which were sorted and activated as described above. As shown in FIG. 8E, WT CD103-like DCs that were activated with zymosan produced higher amounts of IL-12p70 compared to CD5−/− DCs. These findings establish that CD5 contributes to DC subset-specific cytokine secretion upon activation.

CD5−/− Mice are Protected from Psoriasis-Like Disease

Figure 9A:
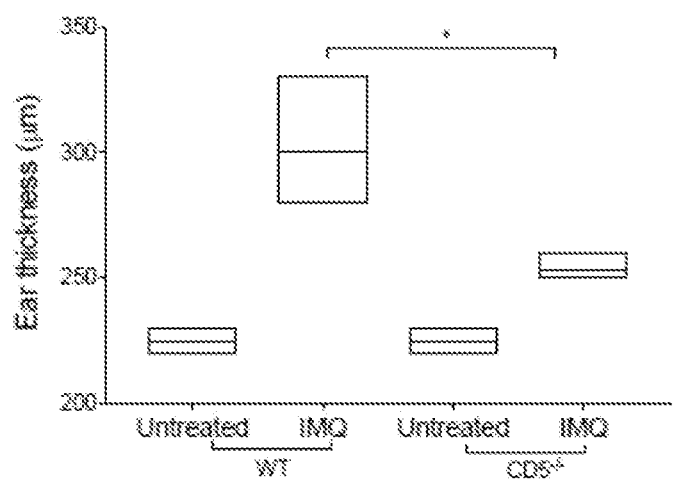
FIG. 9A-FIG. 9G is a series of images and plots showing mice that lack CD5 are protected from psoriasis like disease.
Figure 9B:
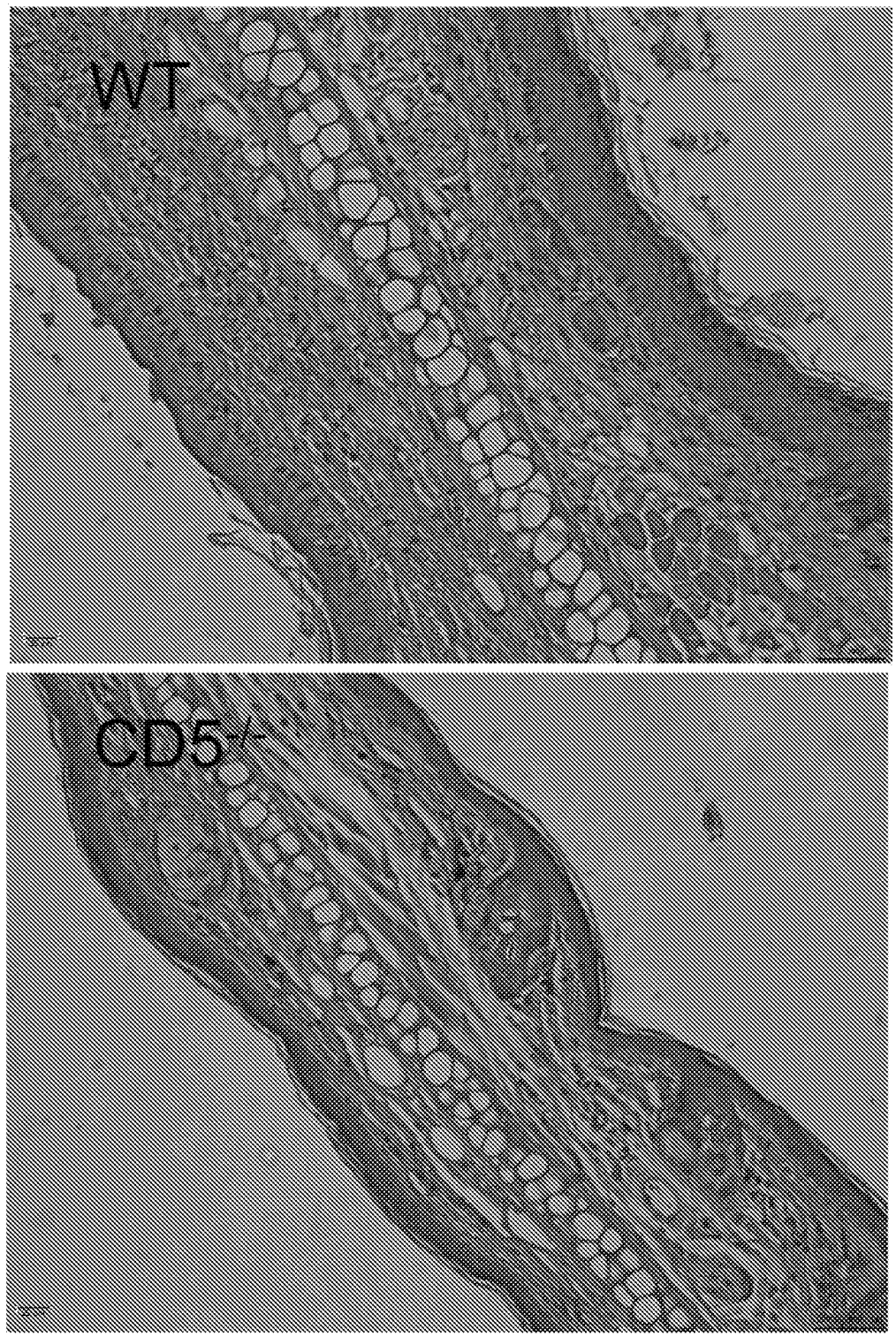
Figure 9C:
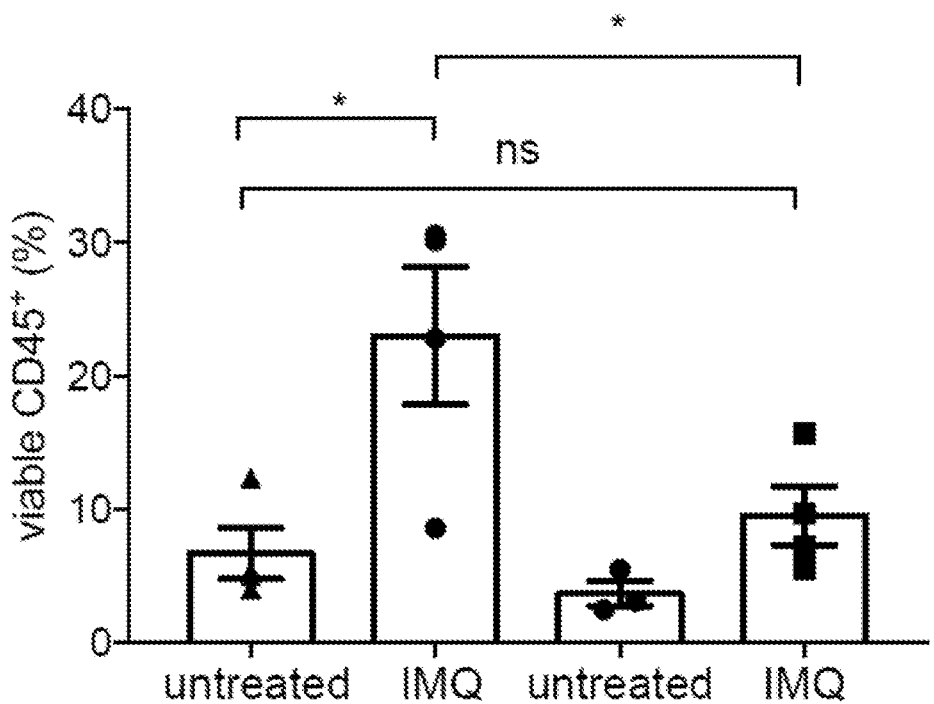
Figure 9D:
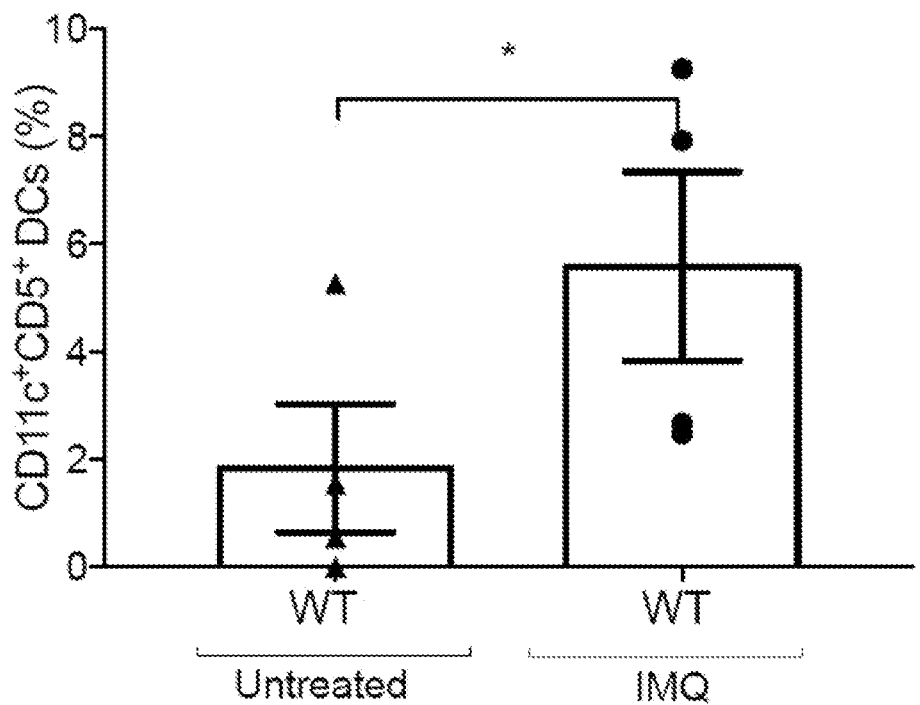
Figure 9E:
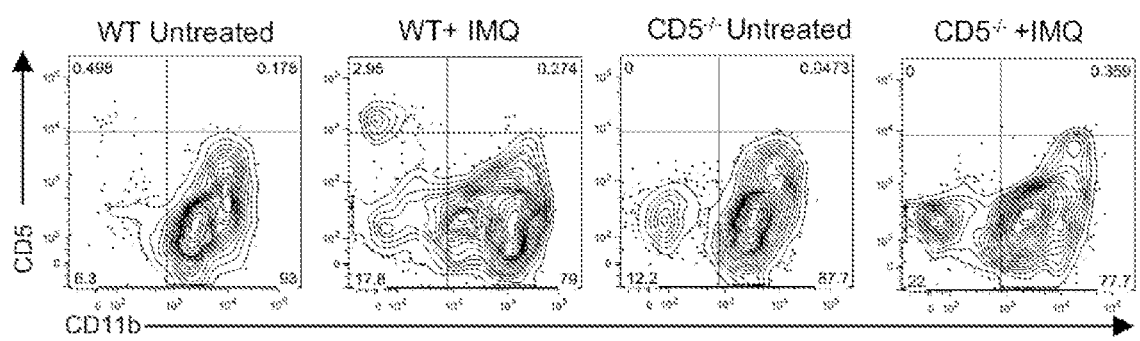
Figure 9F:
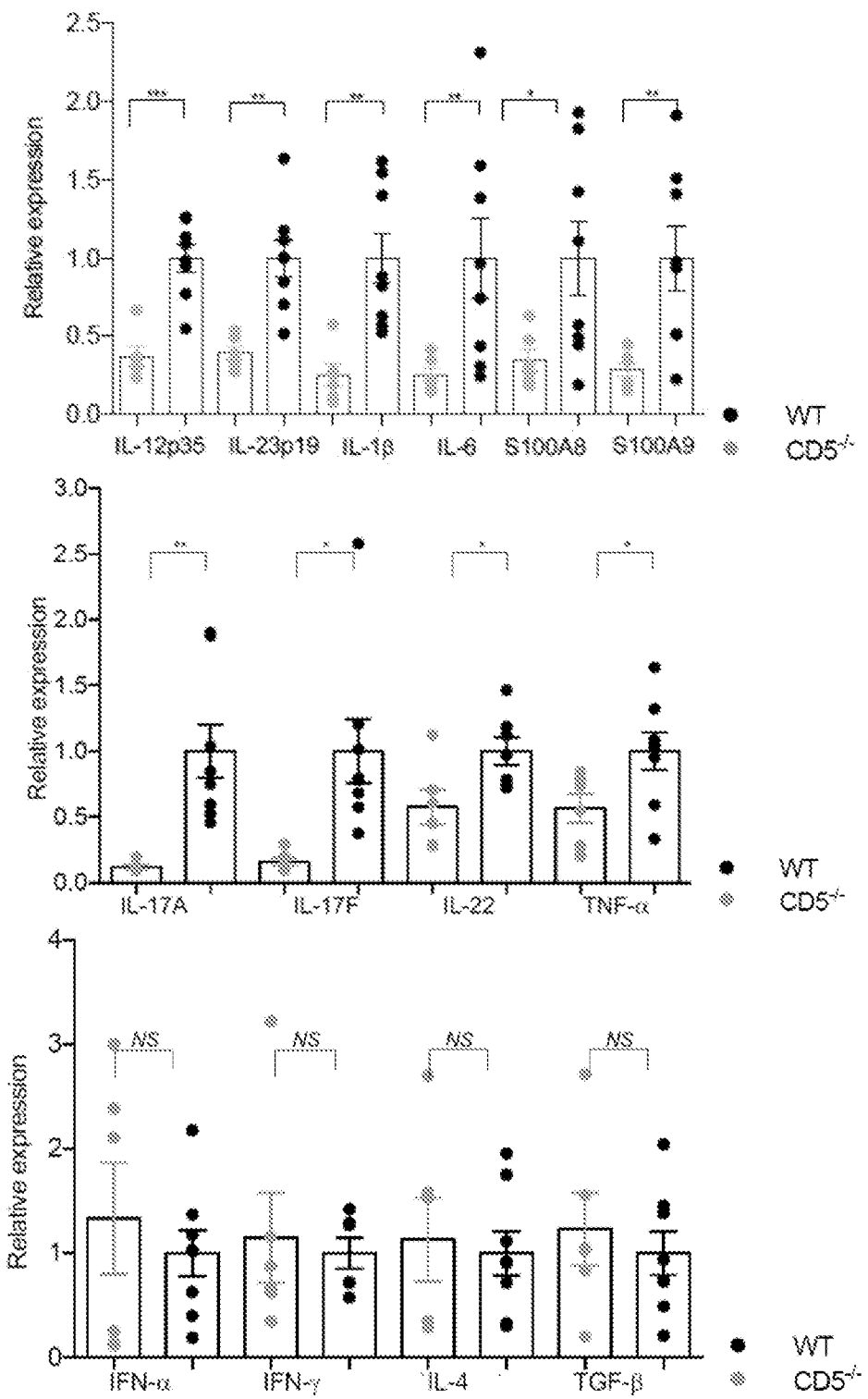
Figure 9G:
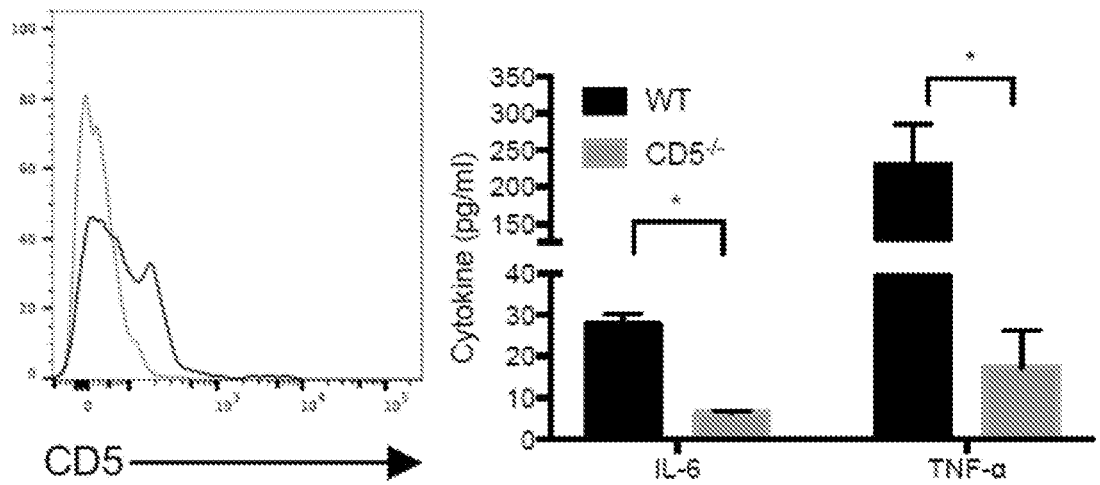

The increased number of CD5+ DCs in the skin of psoriatic patients suggested that these cells might promote disease. This study determined whether CD5−/− (B6.SJL/NCI) mice are protected from psoriasis-like changes. Daily application of 5% Imiquimod cream to the ear skin led to an increase in ear thickness that was nearly 50% less in CD5−/− mice than in wild-type mice at day seven (FIG. 9A). Histological analysis of wild-type ear skin on day seven showed the expected epidermal thickening (acanthosis) (FIG. 9B). In contrast, ear skin from CD5−/− mice had less acanthosis (FIG. 9A and FIG. 9B). The number of CD45+ cells increased in the skin of psoriasis-like disease compared to WT. In contrast, no accumulation of CD45+ cells was observed in the skin of CD5−/− mice after the treatment compared to the wild type mice (FIG. 9C). Flow cytometry identified increased numbers of CD5+CD11c− DCs within the CD11b− population in wild-type ear skin following seven day treatment that was otherwise absent in healthy mouse ear (FIG. 9D and FIG. 9E). After seven days of Imiquimod treatment, CD5−/− ear skin had a lower abundance of transcripts encoding IL-22, IL-6, IL-1β, IL-17F, IL-17A and the antimicrobial peptides S100A9 and S100A8 than did wild-type ear skin (FIG. 9F), while the levels of IFN-α, IFN-γ, IL-4 and TGF-β were similar between the WT and the CD5$^{-/-}$ mice (FIG. 9F). To assess the cytokine production by skin DCs ex vivo, we digested and sorted the CD11c$^+$CD11b$^-$ DCs from the dorsal skin of WT or CD5$^{-/-}$ mice and analyzed their CD5 expression and cytokine production in response to activation (FIG. 9G). Consistent with our results using in vitro DCs, skin DCs from CD5$^{-/-}$ mice expressed lower amount of TNF-α and IL-6 relative to those from wild-type skin in response to zymosan (FIG. 9G). Overall, our findings suggest that the deficiency in CD5 on the DCs is critical for cytokine production by skin cells; this phenomenon contributes to the magnitude of skin inflammation in Imiquimod-induced psoriasis-like disease.

Materials and Methods

Skin and Blood Specimens

Healthy human skin was obtained from donors who underwent cosmetic and plastic surgeries at Washington University in St. Louis School of Medicine (St. Louis, Mo.) and Barnes Jewish Hospital (St. Louis, Mo.) in accordance with Institutional Review Board guidelines. Psoriatic plaque biopsy samples or whole blood samples were acquired at Barnes Jewish West County Hospital (St. Louis, Mo.) in accordance with Institutional Review Board guidelines. Written informed consent was received from each participant prior to collection of psoriatic skin biopsies or blood. Lupus, LC histiocytosis and GvHD skin specimens were obtained from the Dermatopathology center at Washington University School of Medicine in St. Louis. Patient details are listed in a supplemental table (TABLE 1).

CD141$^-$CD5$^-$, CD1a$^{(dim)}$CD141$^+$ or CD14$^+$ DCs. CD40L (100 ng/ml; R&D Systems) were used to activate DCs. The stability of CD5 expression on skin DCs was assessed by culturing sorted CD5$^+$ or CD5$^-$ DCs from the dermis with indicated DC activators for a period of six days. The expression of CD5 was analyzed by flow cytometry.

Human CD34$^+$ and CD34$^-$ HPC Isolation and Differentiation

Cord blood samples were purchased from the St. Louis Cord Blood Bank and processed according to protocols approved by the Institutional Review Board at Washington University in St. Louis School of Medicine. Immediately upon sample arrival, the cord blood was incubated for 20 minutes with RosetteSep Human Hematopoietic Progenitor Cells Enrichment Cocktail (StemCell) to deplete CD2, CD3, CD14, CD16, CD19, CD24, CD56, CD61, CD66b from the cord blood. Further, mononuclear cells were isolated by Ficoll-diatrizoate density gradient centrifugation, using Ficoll-Paque PLUS (GE Healthcare Life Sciences) at 800×g, for 30 minutes with a swing bucket and no brake. CD34$^+$ HPCs were isolated from cord blood mononuclear cells through positive selection using the EasySep Human CD34 Positive Selection Kit (StemCell), Miltenyi Biotec CD34$^+$ microbeads, or labeled with an antibody mix and sorted using a BD Aria II. Progenitor cells were sorted as Live Lin$^-$(CD1c, CD141, BDCA2)$^-$CD10$^-$: CD34$^+$CD117$^+$, CD34$^-$CD117$^+$CD123$^-$, or CD34$^-$CD117$^-$ CD123$^+$ progenitors were cultured as described (Breton et al., 2015a).

TABLE 1

Characteristics and demographic date of patients with psoriasis studied. Psoriasis patient information includes sex, age, anatomical location of the involved and uninvolved biopsy specimens, treatment history and type.

| | | | Biopsy Sections (6 mm) | | |
|---|---|---|---|---|---|
| Patient ID | Sex | Age | Involved Tissue | Uninvolved Tissue | Treatments (previous and current) | Type |
| PS001 | Male | 62 | Unspecified | Unspecified | Unspecified | Plaque |
| PS004 | Male | 70 | Buttock | Buttock | Unspecified | Plaque |
| PS005 | Female | 50 | Left Leg | Right Arm | Humira, Clobetasol Ointment, Methotrexate | Plaque |
| PS007 | Female | 76 | Left Buttock | Left Back | Topical steroids and Enbrel | Plaque |
| PS011 | Female | 57 | Right Forearm | Right Lower Back | NBUVB, MTX, Topicals, Humira, Taclonex | Plaque |
| PS012 | Male | 58 | Right Elbow | Right Upper Arm | NBUVB, Humira, MTX, Clobetasol, Triamcinolone | Plaque |
| PS013 | Female | 47 | Right Forearm | Left Upper Elbow | Triamcinolone | Plaque |
| PS016 | Male | 33 | Left Forearm | Left Arm | Topical steroids | Plaque |
| PS017 | Male | 20 | Right Posterior Medial Leg | Right Posterior Lateral Leg | Methotrexate, Humira | Chronic plaque and Guttate |
| PS018 | Female | 76 | Posterior Neck | Right Inner Arm | Talconex Ointment (Dexamethosone/Dovonex) | Plaque |
| PS019 | Female | 46 | Right Elbow | Right Upper Arm | Topical steroids and Enbrel | Plaque |
| PS025 | Female | 65 | Left letheral lower leg | | Topical steroids | Plaque |

All involved and uninvolved biopsy sections were collected from the patient on the same day.

Dendritic Cell Isolation

Skin DC subsets were isolated as described (Klechevsky et al., 2008). Briefly, tissue specimens were incubated with the bacterial protease, Dispase type II (Roche), for 18 hours at 4° C. Epidermal and dermal sheets were then separated and placed in RPMI 1640 supplemented with 10% fetal bovine serum and incubated for 48 hours at 37° C. The cells that migrated into the medium were enriched using a Ficoll-diatrizoate gradient, Lymphocyte Separation Medium (MP Biomedicals). DCs were further purified by cell sorting using BD FACS Aria II. HLA-DR$^+$CD3$^-$CD19$^-$ DCs subsets are marked in the epidermis as CD1a$^{(hi)}$Langerin$^+$CD5$^+$ or CD1a$^{(hi)}$Langerin$^+$CD5$^-$. In the dermis, the four DC subsets are marked as CD1a$^{(dim)}$CD141$^-$CD5$^+$, CD1a$^{(dim)}$ Briefly, MS-5 stromal cells were maintained in complete alpha-MEM medium supplemented with L-glutamine, but without ribonucleosides and deoxyribonucleosides (Invitrogen), with 10% heat inactivated fetal calf serum (GemCell) and 1% penicillin/streptomycin (Invitrogen). 24 hours prior to co-culture with HPCs, stromal cells were treated with 10 μg/mL of Mitomycin C (Sigma) for three hours at 37° C. and plated at 2.5×10$^4$ cells per 100 μL in a 96-well flat-bottom plate. 1×10$^3$-1×10$^4$ HPCs and cytokines were added in 100 μL supplemented αMEM. FLT3-L (R&D Systems) was used at 200 ng/mL, Stem Cell Factor (SCF) (R&D Systems) at 40 ng/mL, GM-CSF (Sanofi) at 50 ng/mL, TNF-α (R&D Systems) at 10 ng/mL or LTα1/β2 (Sigma) at 50 ng/ml. Cells were cultured for five to ten days. All cytokines were replenished in full dose on day five except for FLT3-L, which was used at 100 ng/mL for replenishment.

Immunofluorescence Analysis of CD5 Expression

Healthy skin and formalin-fixed psoriasis biopsy specimens from plaque (involved) and adjacent skin (uninvolved) were embedded in O.C.T for immunofluorescence staining. Tissue sections were cut into 10-µm sections using the Leica CM 1950. Sections were fixed in 4% PFA for 15 minutes at room temperature and washed with PBS containing 3% Bovine serum albumin (BSA) and 10% saponin. The sections were then quenched with 0.5M Glycine for five minutes, washed, and blocked with PBS/BSA/Saponin for 30 minutes at room temperature. Sections were stained overnight with monoclonal mouse anti-human CD5 (5 µg/ml, UCHT2, eBioscience) or isotype controls, washed and incubated with antimouse Cy3 (3 µg/ml, Jackson Immunoresearch) for two hours. Samples were then washed and stained with mouse anti-human CD1a-FITC (100 mg/ml, NA1/34, DAKO) for two hours followed by 4',6'-diamidino-2-phenylindole (DAPI) for 20 minutes at room temperature. Tissue sections were mounted (ProLong mounting medium, Invitrogen). Images were acquired using an Olympus Confocal Microscope FV1000 using Fluoview software. Image analysis was performed using ImageJ software.

DC/T Cell Co-Cultures

Naive T cells were isolated using Pan Naïve T cell isolation kit (Miltenyi Biotec) according to the manufacturer protocol or sorted as $CCR7^+CD45RA^+CD8^+$ or $CCR7^+CD45RA^+CD4^+$ cells. Isolated T cells were labeled with a CellTrace CFSE cell proliferation kit (Invitrogen) (0.5 µM) CFSE, according to the manufacturer's protocol. The CFSE-labeled T cells were then cultured with sorted skin DCs for seven to ten days. Proliferation was assessed by the percentage of CFSE-labeling dilution. IL-22, IFN-γ and Granzyme B production were assessed by flow cytometry after a short restimulation with PMA (Sigma; 25 ng/ml) and Ionomycin (Sigma; 1 µM). Alternatively, proliferated cells were stimulated overnight with anti-CD3 and anti-CD28 mAbs (DYNAL 8×10^5 beads per 3×10^5 cells) and cytokines produced by the cells were assessed in the supernatant using a Luminex magnetic bead assay.

Microscopy

Cytospins of sorted skin DCs were stained with Wright-Giemsa stain using a Hema 3 kit (Fisher Scientific). Images were acquired using a Leica 63×/1.40 oil objective on a Leica DMIRB microscope with a Leica DFC310 FX camera.

Mice

C57BL/6 mice were obtained from the Jackson Laboratory (Jax; 000664; C57BL/6J). CD5-deficient mice ($CD5^{-/-}$) were obtained as part of the National Institute of Allergy and Infectious Diseases Exchange Program from the transgenic mouse repository maintained by Taconic. As they were extensively backcrossed, all age- and sex-matched mice of a given strain were considered to be identical and were assigned randomly to treatment groups. Breeding, housing and care of all mice was done in specific pathogen-free facilities under a protocol approved by the Washington University Animal Studies Committee.

Mouse DCs

Flt3-L DC: Bone marrow cells were harvested from the tibia and femur of mice. Red blood cells were lysed in ACK buffer, washed and suspended at $2 \times 10^6$/mL in Iscoves complete media (Iscoves, 10% fetal calf serum, L-glutamine, nonessential amino acids, Sodium Pyruvate, 2-βME and gentamycin), and supplemented with 5% human FLT3L-FC fusion protein supernatant (generated by Dr. Marina Cella) per well of a 24-well plate. Cells were incubated at 37° C., 5% $CO_2$ for ten days. CD103-like DCs were differentiated as described (Mayer et al., 2014). Briefly, bone marrow cells were cultured in Iscoves complete media supplemented with 10% human FLT3L-FC fusion protein sup and 5 ng/ml of recombinant GM-CSF per well in 4 mL per well of a 6-well plate. Cells were incubated at 37° C., 5% $CO_2$. Cytokines were replenished on day five and on day eight, and the cells were propagated for another seven days before harvest.

Mouse Tissue Preparation

Ears were split and digested in 1.86 U/mL Dispase type II (Roche). Separated epidermal sheets were digested with trypsin EDTA for 30 minutes. Dermal sheets were digested for 60-120 minutes in RPMI containing 85 µg/ml Liberase™ (Roche Applied Science), 100 µg/ml DNAseI (Sigma), 0.5 mg/ml hyaluronidase (Sigma) and 2% FCS. Alternatively, 125 µg/ml Liberase TL (Roche Applied Science) and 100 µg/ml DNAseI (Sigma) were used for digestion. In addition, whole ear skin was minced and digested with Liberase, DNAse I and hyaluronidase as described above. Digestion enzymes were quenched by the addition of 5 mM EDTA and 1% serum. All tissues were disaggregated by passage through a 70-µm or 100-µm nylon cell strainer (BD Bioscience).

Imiquimod Model of Psoriasis-Like Disease.

B6/NCI and $CD5^{-/-}$ mice between six and twelve weeks of age were treated daily for seven days on each ear with 5 mg of 5% Imiquimod cream (Imiquimod Cream 5%; Perrigo. Co.) or left untreated for control skin. For histological analysis, paraformaldehyde-fixed, paraffin-embedded ear skin sections were prepared and stained with hematoxylin and eosin by the Washington University Digestive Diseases Research Cores Center. For the identification of $CD5^+$ $CD11c^+$ DCs in ear skin, ears were digested as described above and analyzed by flow cytometry. For the analysis of DC activation, primary skin DCs were sorted based on Class $II^+CD11c^+CD11b^-$ expression. Cells were activated overnight as indicated and analyzed for cytokines using BD cytometric bead array.

Quantitative Real Time PCR (qPCR)

qPCR was carried out after Trizol-based RNA extraction using miRNeasy Mini Kit (QIAGEN) and thereafter using SYBR green (BioRad). The results were normalized to HPRT. Quantitative measurements are presented as where $\Delta\Delta Ct = (Ct_{Target} - Ct_{house\ keeping\ gene})_{assay} - (Ct_{Target} - Ct_{house\ keeping\ gene})_{control}$, as described previously (1). The primers used are recited in SEQ ID NO 1-22. The following primers were used to detect the targets of interest:

IL-12p35 F-  (SEQ ID NO: 1)
CCATCAGCAGATCATTCTAGACAA;

IL-12p35 R-  (SEQ ID NO: 2)
CGCCATTATGATTCAGAGACTG;

IL-23p19 F-  (SEQ ID NO: 3)
AGCAACTTCACACCTCCCTAC;

IL-23p19 R-  (SEQ ID NO: 4)
ACTGCTGACTAGAACTCAGGC;

IFN-γ F-  (SEQ ID NO: 5)
ACTGGCAAAAGGATGGTGAC;

-continued

IFN-γ R-
GACCTGTGGGTTGTTGACCT;
(SEQ ID NO: 6)

IFNα F-
CATTCTGCAATGACCTCCAC;
(SEQ ID NO: 7)

IFNα R-
TCAGGGGAAATTCCTGCAC;
(SEQ ID NO: 8)

IL-17A F-
GACTACCTCAACCGTTCCACGTC;
(SEQ ID NO: 9)

IL-17A R-
TCTATCAGGGTCTTCATTGCG;
(SEQ ID NO: 10)

IL-17F F-
CCCAGGAAGACATACTTAGAAGAAA;
(SEQ ID NO: 11)

IL-17F R-
CAACAGTAGCAAAGACTTGACCA;
(SEQ ID NO: 12)

IL-22 F-
TTTCCTGACCAAACTCAGCA;
(SEQ ID NO: 13)

IL-22 R-
CTGGATGTTCTGGTCGTCAC;
(SEQ ID NO: 14)

S100A8 F-
TGCGATGGTGATAAAAGTGG;
(SEQ ID NO: 15)

S100A8 R-
GGCCAGAAGCTCTGCTACTC;
(SEQ ID NO: 16)

S100A9 F-
CACCCTGAGCAAGAAGGAAT;
(SEQ ID NO: 17)

S100A9 R-
TGTCATTTATGAGGGCTTCATTT;
(SEQ ID NO: 18)

IL-1β F-
CAACCAACAAGTGATATTCTCCATG;
(SEQ ID NO: 19)

IL-1β R-
GATCCACACTCTCCAGCTGCA;
(SEQ ID NO: 20)

HPRT F-
TTGCTCGAGATGTCATGAAGGA;
or
(SEQ ID NO: 21)

HPRT R-
AGCAGGTCAGCAAAGAACTTATAGC.
(SEQ ID NO: 22)

The PCR temperature conditions included an initial denaturation at 94° C. for five minutes. Subsequently, 40 cycles of amplification were performed that included denaturation at 94° C. for ten seconds and annealing and elongation at 60° C. for 30 seconds.

Statistical Analysis

GraphPad Prism was used for statistical analyses. Statistical analysis was done using T-test and ANOVA. Significant p-value was lower than 0.05 and labeled as *(p-value≤0.05), (p-value≤0.01), *(p-value≤0.005), and ****(p-value≤0.001).

Discussion

The results presented in this study show that CD5 marks a novel terminally differentiated human DC subset that we found in both skin and blood as a subset of the CD1c-expressing DCs. In the skin, the CD5-expressing population in the dermis is a fraction of the $CD1c^+CD1a^{(dim)}CD141^-$ DCs. Moreover, CD5 is also expressed on a subset of $CD1a^{(hi)}CD1c^+$ LCs, which constitutes a previously unappreciated heterogeneity within human LCs. We found that the $CD5^+$ DCs are highly potent inducers of inflammatory Th22 and CTL responses which have been implicated in psoriasis. $CD5^+$ DCs were significantly elevated in psoriatic plaques. Using DCs from $CD5^{-/-}$ mice we show that CD5 is important for the DCs to secrete pro-inflammatory cytokines, and that CD5-dependent cells contribute to psoriasis-like disease as inflammatory cytokines and skin inflammation are reduced in $CD5^{-/-}$ skin.

Understanding the division of labor and the role of mDC subsets in activating distinct defenses of the adaptive immune system is necessary for the development of new vaccines that address chronic diseases (including cancer, AIDS, malaria, and hepatitis C) or for targeted therapy approaches aiming at inducing tolerance in autoimmunity. We showed that the $CD5^+$ DCs are able to prime Th22 cells, as well as CTLs. We show that CD5 expression on DCs is important for their ability to produce cytokines upon activation. The induction of a unique set of cytokines or co-stimulatory molecules in response to CD5-ligation on skin DCs could explain their ability to prime these responses and is the topic in ongoing studies.

While there is no confirmed ligand for CD5, a recent study suggests that CD5 may be homophilic, binding CD5 on the surface of other cells. In addition, it was also shown that the ligation of CD5 on T cells results in the polarization of naïve T cells into the Th17 pathway, and more recently in the mouse a CD5 molecule Like (CDSL) was shown to regulate the pathogenicity of Th17. Thus, it is currently believed that CD5 on DCs might bind to CD5 (or CDSL) on T cells resulting in Th17 polarization. Initial assessment of the role of CD5 co-stimulation on DCs by using a monoclonal antibody to CD5 during a co-culture led to increased T cell activation, suggesting that ligation of CD5 on DCs may deliver a positive signal or promote their activation.

Using DCs from $CD5^{-/-}$ mice, we show that CD5 might serve as a pattern recognition receptor on DCs and can mediate the production of pro-inflammatory cytokines in response to activation (mainly zymosan). This is consistent with a study showing that CD5 can recognize a fungal cell wall component, zymosan. Thus, it is possible that CD5 expression on DCs, as a scavenger receptor, mediates uptake or pathogen clearance but also serves as a danger receptor. This is intriguing, as none of the other known receptors for zymosan (i.e., TLR-2 or dectin-1) are present on $CD5^+$ LCs and dermal $CD1a^{(dim)}$ DCs, but they are highly abundant on the dermal $CD14^+$ DCs (Artyomov et al., 2015). Whether CD5 recognizes other pathogen-associated molecular patterns (PAMPs) remains to be established. Overall, the rapid proliferation and cytokine production mediated by $CD5^+$ DCs led us to propose that these DCs may be prone to respond faster to a foreign antigen, and that CD5 might facilitate the recognition of a danger signal. If this hypothesis is true, this functionality of the $CD5^+$ DCs could be advantageous, particularly in the skin, which serves as the first line of defense against pathogens. Epigenetic markers underpinning the rapid maturation of $CD5^+$ DCs might further help elucidate their function.

We have noticed that the differences between the dermal CD5$^+$ and the CD5$^-$ DCs in priming allogeneic T cell responses were greater than those between CD5$^+$ LCs and CD5$^-$ LCs. As previously reported, LCs are highly effective initiators of allogeneic T cell responses (Klechevsky et al., 2008) and thus, limiting culture conditions (i.e., high DC:T ratio, low IL-2) permitted to reveal the contribution of CD5 to the outcome of the T cell responses. It is currently believed that CD5$^+$ LCs will be particularly efficient at priming an antigen-specific response where the precursor frequency is low, or when the antigen is of low affinity, like these that are expressed in tumors. Moreover, as a scavenger receptor, CD5 on CD1a$^{hi}$ LCs might also mediate the presentation of lipids and the priming of CD1a-restricted Th22 as seen in patients with psoriasis.

The developmental stages of human DCs are still incompletely defined and the relationships between skin and peripheral blood cDCs are unclear. This is particularly true with respect to the CD1c$^+$CD5$^+$ DCs, which are found in both blood and skin. We used a previously described MS-5 culture system to challenge the differentiation potential of single human progenitors into the CD1a, CD1c and CD5$^+$ DC subsets. We show that CD5$^+$ DCs can be differentiated from human progenitors isolated from cord blood. Interestingly, similar to what was observed in the skin, the differentiated cells represent a subset of the CD1a$^+$CD1c$^+$ DCs and the CD1a$^{(dim\ or\ neg)}$CD1c$^+$ DCs. The former may be similar to the CD1a$^{hi}$CD1c$^+$CD5$^+$ LCs, while the latter may be similar to the blood CD1c$^+$ DCs and to the dermal CD1a$^{(dim)}$CD1c$^+$ DCs. The fact that only a fraction of CD34$^+$ HPCs differentiated into the CD5$^+$ DCs led us to hypothesize that there could be a committed progenitor for CD5$^+$ DCs. To test this, cord blood was analyzed for common myeloid progenitors (Doulatov et al., 2010). Indeed, we discovered a population marked as CD34$^-$CD123$^{hi}$CD10$^-$ in cord blood and human dermis that gave rise primarily to the CD11c$^+$CD1c$^+$CD5$^+$ DCs, which we define as "pre-CD5$^+$ DCs". Interestingly, we found a noticeable increase numbers of these progenitors in patients' blood compared to healthy individuals (not shown), however, conceivably a more significant accumulation of pre-CD5$^+$ DCs will be found in the inflamed dermis. In addition to FLT3-L, we assessed whether some additional signals will promote this terminally CD5-positive differentiated step. It was previously shown that TNF-$\alpha$ will promote the differentiation of CD34$^+$ into DCs characterized by the expression of CD1a. In the mouse, lymphotoxin beta receptor signaling was required for the differentiation step of a subset of the CD11b$^+$ DCs expressing high amounts of ESAM. We found that TNF-$\alpha$ and LT$\alpha$/$\beta$ could significantly enhance CD5$^+$ DC numbers. It is believed that pre-conditioning/exposure of dermal progenitors (CD123$^+$CD117$^{(dim)}$) to LT$\alpha$/$\beta$ in the skin, might prone them to develop into the CD5$^+$ DC subset. Thus, unabated induction of CD5$^+$ DCs from dermal progenitors by TNF-$\alpha$ and lymphotoxin may drive the autoimmune response in psoriasis.

Using a handful of DC activators, inflammatory cytokines, or T cell signals, we show that once differentiated, CD1c$^+$CD5$^-$ DCs from the dermis (FIG. 1E) but also the epidermis (not shown) would not upregulate CD5 upon activation, suggesting that CD5 does not represent an activation marker. Moreover, the presence of CD5$^+$ DCs in blood and more importantly in cord blood (FIG. 10A), which has never been exposed to a foreign antigen further supports our hypothesis that CD5 demarked a unique subset. Nevertheless, this data does not exclude the possibility that within the skin microenvironment or in response to a pathogen CD5 might be induced on the CD5 negative DCs.

Interestingly, we found that monocytes could also differentiate into CD5-expressing APCs, in the presence of GM-CSF. However, these monocyte-differentiated cells lacked CD1c expression, which distinguishes them from the CD34-differentiated subset. The differentiation of monocytes into CD5-expressing DCs may occur in vivo under inflammatory conditions. Indeed, we found that TNF-$\alpha$, LT$\alpha$/$\beta$, and IL-34 supported the differentiation of the CD5$^+$ cells, while IL-4 blocked their differentiation (see e.g., FIG. 17). This suggests that IL-4 could be used therapeutically to control de-novo differentiation of CD5-expressing DCs from monocytes.

Our observation that the numbers of CD5$^+$ DCs were significantly elevated in lesional psoriatic skin suggested their involvement in the disease. To demonstrate feasibility, we asked whether psoriasis-like disease initiation or severity will be affected by the absence of CD5. We found that CD5$^{-/-}$ mice were protected from psoriasis-like disease as inflammatory cytokines and skin inflammation were reduced in CD5$^{-/-}$ skin. Moreover, CD5$^+$ DCs accumulated in lesional skin and produced more pro-inflammatory cytokines (IL-6 and TNF-$\alpha$) compared to CD5-deficient skin DCs. The psoriasis-like disease model is based on the daily application of Imiquimod, a TLR-7-agonist for seven days (Flutter and Nestle, 2013). The murine cell populations that express high levels of TLR7 include macrophages and DCs, which secrete proinflammatory cytokines in response to TLR7 stimulation. Moreover, a clear role for DCs in Imiquimod-induced psoriasis is demonstrated by the response in DC-depleted mice, in which epidermal thickening, cellular infiltrates, and IL-17 are all reduced (Tortola et al., 2012). Similarly, in disease-resistant MyD88 KO mice, restoration of MyD88 specifically in CD11c$^+$ cells clearly shows that danger sensing in conventional DCs is the crucial pathway involved in skin inflammation (Wohn et al., 2013). Interestingly, pDCs and IFN-$\alpha$ signaling are not required for skin inflammation in response to Imiquimod. This is consistent with the similar levels of IFN-$\alpha$ transcripts in the treated skin of WT or CD5KO mice (FIG. 9G). Overall, the murine model coincides with the human data, supporting a critical role for CD5 on DCs in psoriasis, but nevertheless we cannot exclude the possibility of a key role for CD5 on T cells.

Overall, a practical use of our discovery will be the mobilization of CD5$^+$ DCs in vaccines where CTL induction is desired, such as in cancer. In addition, strategies to regulate CD5$^+$ DC composition or function will represent an innovative approach for the treatment of psoriasis and other immune-mediated disorders that are dependent on IFN-$\gamma$ and IL-22 beyond the skin.

REFERENCES

Artyomov, M. N., A. Munk, L. Gorvel, D. Korenfeld, M. Cella, T. Tung, and E. Klechevsky. 2015. Modular expression analysis reveals functional conservation between human Langerhans cells and mouse cross-priming dendritic cells. *J Exp Med* 212:743-757.

Banchereau, J., and R. M. Steinman. 1998. Dendritic cells and the control of immunity. *Nature* 392:245-252.

Banchereau, J., L. Thompson-Snipes, S. Zurawski, J. P. Blanck, Y. Cao, S. Clayton, J. P. Gorvel, G. Zurawski, and E. Klechevsky. 2012a. The differential production of cytokines by human Langerhans cells and dermal CD14 (+) DCs controls CTL priming. *Blood* 119:5742-5749.

Banchereau, J., H. Ueno, M. Dhodapkar, J. Connolly, J. P. Finholt, E. Klechevsky, J. P. Blanck, D. A. Johnston, A. K. Palucka, and J. Fay. 2005. Immune and clinical outcomes in patients with stage IV melanoma vaccinated with peptide-pulsed dendritic cells derived from CD34+ progenitors and activated with type I interferon. *J Immunother* 28:505-516.

Banchereau, J., S. Zurawski, L. Thompson-Snipes, J. P. Blanck, S. Clayton, A. Munk, Y. Cao, Z. Wang, S. Khandelwal, J. Hu, W. H. t. McCoy, K. A. Palucka, Y. Reiter, D. H. Fremont, G. Zurawski, M. Colonna, A. S. Shaw, and E. Klechevsky. 2012b. Immunoglobulin-like transcript receptors on human dermal CD14+ dendritic cells act as a CD8-antagonist to control cytotoxic T cell priming. *Proc Natl Acad Sci USA* 109:18885-18890.

Breton, G., J. Lee, K. Liu, and M. C. Nussenzweig. 2015a. Defining human dendritic cell progenitors by multiparametric flow cytometry. *Nature protocols* 10:1407-1422.

Breton, G., J. Lee, Y. J. Zhou, J. J. Schreiber, T. Keler, S. Puhr, N. Anandasabapathy, S. Schlesinger, M. Caskey, K. Liu, and M. C. Nussenzweig. 2015b. Circulating precursors of human CD1c+ and CD141$^+$ dendritic cells. *J Exp Med* 212:401-413.

Brown, M. H., and E. Lacey. 2010. A ligand for CD5 is CD5. *J Immunol* 185:6068-6074.

Caux, C., C. Massacrier, B. Vanbervliet, B. Dubois, I. Durand, M. Cella, A. Lanzavecchia, and J. Banchereau. 1997. CD34+ hematopoietic progenitors from human cord blood differentiate along two independent dendritic cell pathways in response to granulocyte-macrophage colony-stimulating factor plus tumor necrosis factor alpha: II. Functional analysis. *Blood* 90:1458-1470.

Caux, C., B. Vanbervliet, C. Massacrier, C. Dezutter-Dambuyant, B. de Saint-Vis, C. Jacquet, K. Yoneda, S. Imamura, D. Schmitt, and J. Banchereau. 1996. CD34+ hematopoietic progenitors from human cord blood differentiate along two independent dendritic cell pathways in response to GM-CSF+TNF alpha. *J Exp Med* 184:695-706.

Chamian, F., M. A. Lowes, S. L. Lin, E. Lee, T. Kikuchi, P. Gilleaudeau, M. Sullivan-Whalen, I. Cardinale, A. Khatcherian, I. Novitskaya, K. M. Wittkowski, and J. G. Krueger. 2005. Alefacept reduces infiltrating T cells, activated dendritic cells, and inflammatory genes in psoriasis vulgaris. *Proc Natl Acad Sci USA* 102:2075-2080.

Cheung, K. L., R. Jarrett, S. Subramaniam, M. Salimi, D. Gutowska-Owsiak, Y. L. Chen, C. Hardman, L. Xue, V. Cerundolo, and G. Ogg. 2016. Psoriatic T cells recognize neolipid antigens generated by mast cell phospholipase delivered by exosomes and presented by CD1a. *J Exp Med*

Chu, C. C., N. Ali, P. Karagiannis, P. Di Meglio, A. Skowera, L. Napolitano, G. Barinaga, K. Grys, E. Sharif-Paghaleh, S. N. Karagiannis, M. Peakman, G. Lombardi, and F. O. Nestle. 2012. Resident CD141 (BDCA3)+ dendritic cells in human skin produce IL-10 and induce regulatory T cells that suppress skin inflammation. *J Exp Med* 209:935-945.

de Jong, A., V. Pena-Cruz, T. Y. Cheng, R. A. Clark, I. Van Rhijn, and D. B. Moody. 2010. CD1a-autoreactive T cells are a normal component of the human alphabeta T cell repertoire. *Nat Immunol* 11:1102-1109.

de Wit, J., Y. Souwer, A. J. van Beelen, R. de Groot, F. J. Muller, H. Klaasse Bos, T. Jorritsma, M. L. Kapsenberg, E. C. de Jong, and S. M. van Ham. 2011. CD5 costimulation induces stable Th17 development by promoting IL-23R expression and sustained STAT3 activation. *Blood* 118:6107-6114.

Doulatov, S., F. Notta, K. Eppert, L. T. Nguyen, P. S. Ohashi, and J. E. Dick. 2010. Revised map of the human progenitor hierarchy shows the origin of macrophages and dendritic cells in early lymphoid development. *Nat Immunol* 11:585-593.

Flutter, B., and F. O. Nestle. 2013. TLRs to cytokines: mechanistic insights from the imiquimod mouse model of psoriasis. *Eur J Immunol* 43:3138-3146.

Fujita, H., K. E. Nograles, T. Kikuchi, J. Gonzalez, J. A. Carucci, and J. G. Krueger. 2009. Human Langerhans cells induce distinct IL-22-producing CD4+ T cells lacking IL-17 production. *Proc Natl Acad Sci USA* 106:21795-21800.

Gaublomme, J. T., N. Yosef, Y. Lee, R. S. Gertner, L. V. Yang, C. Wu, P. P. Pandolfi, T. Mak, R. Satija, A. K. Shalek, V. K. Kuchroo, H. Park, and A. Regev. 2015. Single-Cell Genomics Unveils Critical Regulators of Th17 Cell Pathogenicity. *Cell* 163:1400-1412.

Gimferrer, I., M. Farnos, M. Calvo, M. Mittelbrunn, C. Enrich, F. Sanchez-Madrid, J. Vives, and F. Lozano. 2003. The accessory molecules CD5 and CD6 associate on the membrane of lymphoid T cells. *J Biol Chem* 278:8564-8571.

Hope, J. L., B. Pulendran, S. P. Schoenberger, and P. D. Katsikis. 2016. 1st International Conference on Human & Translational Immunology. *Nat Immunol* 18:1-4.

Klechevsky, E. 2013. Human dendritic cells—stars in the skin. *Eur J Immunol* 43:3147-3155.

Klechevsky, E. 2015. Functional Diversity of Human Dendritic Cells. *Adv Exp Med Biol* 850:43-54.

Klechevsky, E., R. Morita, M. Liu, Y. Cao, S. Coquery, L. Thompson-Snipes, F. Briere, D. Chaussabel, G. Zurawski, A. K. Palucka, Y. Reiter, J. Banchereau, and H. Ueno. 2008. Functional specializations of human epidermal Langerhans cells and CD14+ dermal dendritic cells. *Immunity* 29:497-510.

Lee, J., G. Breton, T. Y. Oliveira, Y. J. Zhou, A. Aljoufi, S. Puhr, M. J. Cameron, R. P. Sekaly, M. C. Nussenzweig, and K. Liu. 2015. Restricted dendritic cell and monocyte progenitors in human cord blood and bone marrow. *J Exp Med* 212:385-399.

Lenz, A., M. Heine, G. Schuler, and N. Romani. 1993. Human and murine dermis contain dendritic cells. Isolation by means of a novel method and phenotypical and functional characterization. *J Clin Invest* 92:2587-2596.

Lewis, K. L., M. L. Caton, M. Bogunovic, M. Greter, L. T. Grajkowska, D. Ng, A. Klinakis, I. F. Charo, S. Jung, J. L. Gommerman, Ivanov, II, K. Liu, M. Merad, and B. Reizis. 2011. Notch2 receptor signaling controls functional differentiation of dendritic cells in the spleen and intestine. *Immunity* 35:780-791.

Lowes, M. A., F. Chamian, M. V. Abello, J. Fuentes-Duculan, S. L. Lin, R. Nussbaum, I. Novitskaya, H. Carbonaro, I. Cardinale, T. Kikuchi, P. Gilleaudeau, M. Sullivan-Whalen, K. M. Wittkowski, K. Papp, M. Garovoy, W. Dummer, R. M. Steinman, and J. G. Krueger. 2005. Increase in TNF-alpha and inducible nitric oxide synthase-expressing dendritic cells in psoriasis and reduction with efalizumab (anti-CD11a). *Proc Natl Acad Sci USA* 102:19057-19062.

Lowes, M. A., T. Kikuchi, J. Fuentes-Duculan, I. Cardinale, L. C. Zaba, A. S. Haider, E. P. Bowman, and J. G. Krueger. 2008. Psoriasis vulgaris lesions contain discrete populations of Th1 and Th17 T cells. *The Journal of investigative dermatology* 128:1207-1211.

Mathers, A. R., B. M. Janelsins, J. P. Rubin, O. A. Tkacheva, W. J. Shufesky, S. C. Watkins, A. E. Morelli, and A. T. Larregina. 2009. Differential capability of human cutaneous dendritic cell subsets to initiate Th17 responses. *J Immunol* 182:921-933.

Mayer, C. T., P. Ghorbani, A. Nandan, M. Dudek, C. Arnold-Schrauf, C. Hesse, L. Berod, P. Stuve, F. Puttur, M. Merad, and T. Sparwasser. 2014. Selective and efficient generation of functional Batf3-dependent CD103+ dendritic cells from mouse bone marrow. *Blood* 124: 3081-3091.

Nestle, F. O., C. Conrad, A. Tun-Kyi, B. Homey, M. Gombert, O. Boyman, G. Burg, Y. J. Liu, and M. Gilliet. 2005. Plasmacytoid predendritic cells initiate psoriasis through interferon-alpha production. *J Exp Med* 202:135-143.

Nestle, F. O., X. G. Zheng, C. B. Thompson, L. A. Turka, and B. J. Nickoloff. 1993. Characterization of dermal dendritic cells obtained from normal human skin reveals phenotypic and functionally distinctive subsets. *J Immunol* 151:6535-6545.

Penel-Sotirakis, K., E. Simonazzi, J. Peguet-Navarro, and A. Rozieres. 2012. Differential capacity of human skin dendritic cells to polarize CD4+ T cells into IL-17, IL-21 and IL-22 producing cells. *PLoS One* 7:e45680.

Romani, N., S. Gruner, D. Brang, E. Kampgen, A. Lenz, B. Trockenbacher, G. Konwalinka, P. O. Fritsch, R. M. Steinman, and G. Schuler. 1994. Proliferating dendritic cell progenitors in human blood. *J Exp Med* 180:83-93.

Sabat, R., W. Ouyang, and K. Wolk. 2014. Therapeutic opportunities of the IL-22-IL-22R1 system. *Nature reviews. Drug discovery* 13:21-38.

Seneschal, J., R. A. Clark, A. Gehad, C. M. Baecher-Allan, and T. S. Kupper. 2012. Human epidermal Langerhans cells maintain immune homeostasis in skin by activating skin resident regulatory T cells. *Immunity* 36:873-884.

Tortola, L., E. Rosenwald, B. Abel, H. Blumberg, M. Schafer, A. J. Coyle, J. C. Renauld, S. Werner, J. Kisielow, and M. Kopf. 2012. Psoriasiform dermatitis is driven by IL-36-mediated DC-keratinocyte crosstalk. *J Clin Invest* 122:3965-3976.

Vera, J., R. Fenutria, O. Canadas, M. Figueras, R. Mota, M. R. Sarrias, D. L. Williams, C. Casals, J. Yelamos, and F. Lozano. 2009. The CD5 ectodomain interacts with conserved fungal cell wall components and protects from zymosan-induced septic shock-like syndrome. *Proc Natl Acad Sci USA* 106:1506-1511.

Wang, C., N. Yosef, J. Gaublomme, C. Wu, Y. Lee, C. B. Clish, J. Kaminski, S. Xiao, G. Meyer Zu Horste, M. Pawlak, Y. Kishi, N. Joller, K. Karwacz, C. Zhu, M. Ordovas-Montanes, A. Madi, I. Wortman, T. Miyazaki, R. A. Sobel, H. Park, A. Regev, and V. K. Kuchroo. 2015. CDSL/AIM Regulates Lipid Biosynthesis and Restrains Th17 Cell Pathogenicity. *Cell* 163:1413-1427.

Wohn, C., J. L. Ober-Blobaum, S. Haak, S. Pantelyushin, C. Cheong, S. P. Zahner, S. Onderwater, M. Kant, H. Weighardt, B. Holzmann, B. Reizis, B. Becher, E. P. Prens, and B. E. Clausen. 2013. Langerin(neg) conventional dendritic cells produce IL-23 to drive psoriatic plaque formation in mice. *Proc Natl Acad Sci USA* 110:10723-10728.

Zaba, L. C., J. Fuentes-Duculan, N. J. Eungdamrong, M. V. Abello, I. Novitskaya, K. C. Pierson, J. Gonzalez, J. G. Krueger, and M. A. Lowes. 2009. Psoriasis is characterized by accumulation of immunostimulatory and Th1/Th17 cell-polarizing myeloid dendritic cells. *The Journal of investigative dermatology* 129:79-88.

Example 2: CD5 KO Mice Failed to Reject Tumor

The following example describes studies showing that CD5 deficient mice failed to reject a tumor. Thus, it is currently thought that CD5 is critical for tumor rejection. As such, enhancement of CD5 differentiation (elaborated in Example 1) can be effective in the management and treatment of cancer.

The tumor growth data (see e.g., FIG. 13) from the CD5 knockout mice injected with 1969. 1969 is a regressor tumor derived from a female C57BL6 Rag2-/- mouse. The CD5 KO and WT mice showed differences in tumor size (see e.g., FIG. 13C).

Example 3: IL-18 in CD5

$CD5^+$ DC Express the IFN-γ-Inducing Factor IL-18

Figure 14A:
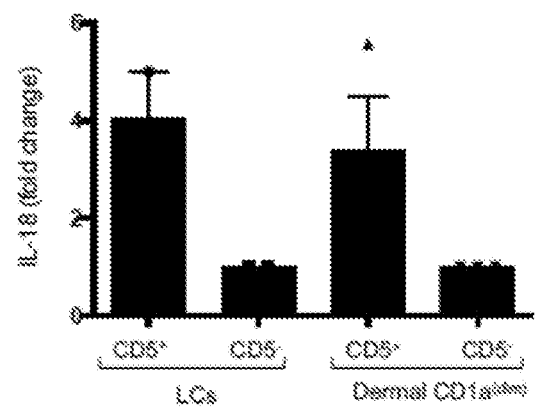
FIG. 14A-FIG. 14D is a series of bar graphs, images, and plots showing CD5$^+$ DCs prime IFN-γ producing CD8$^+$ T cells via IL-18.
Figure 14B:
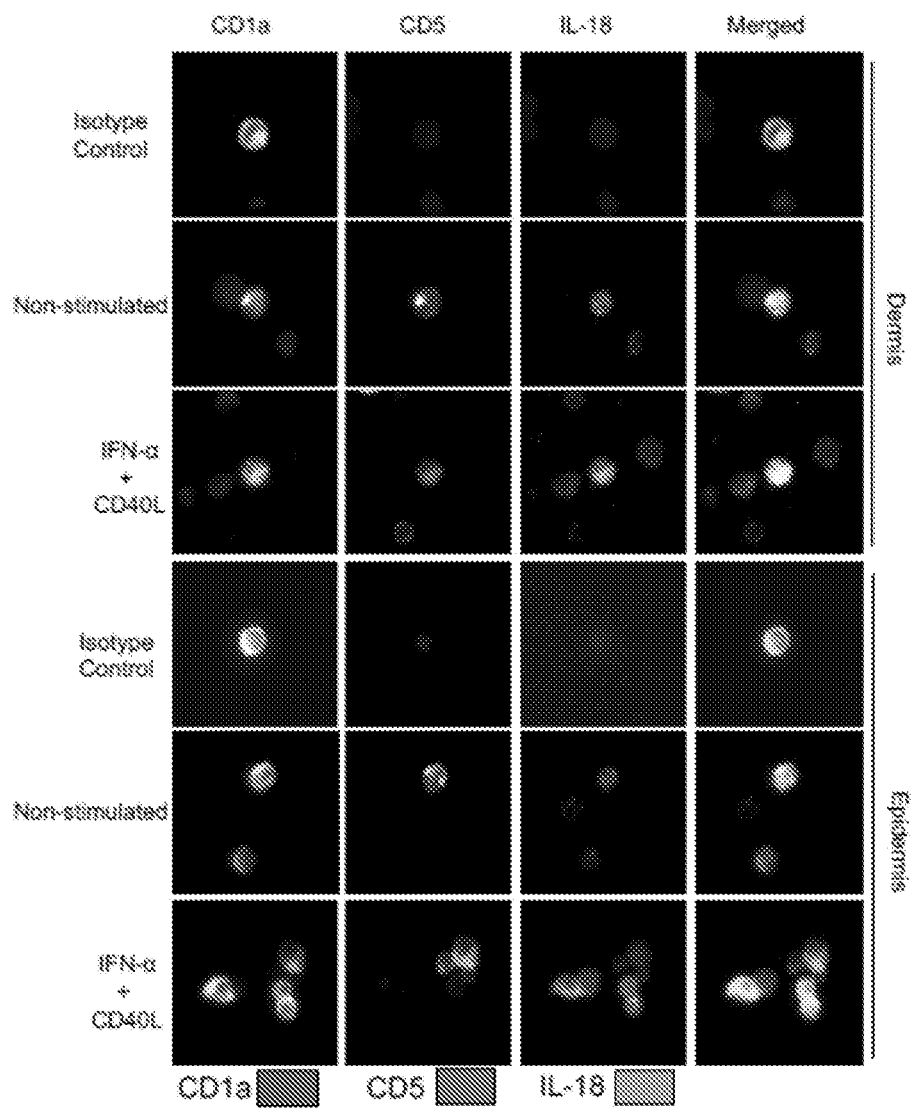
Figure 14C:
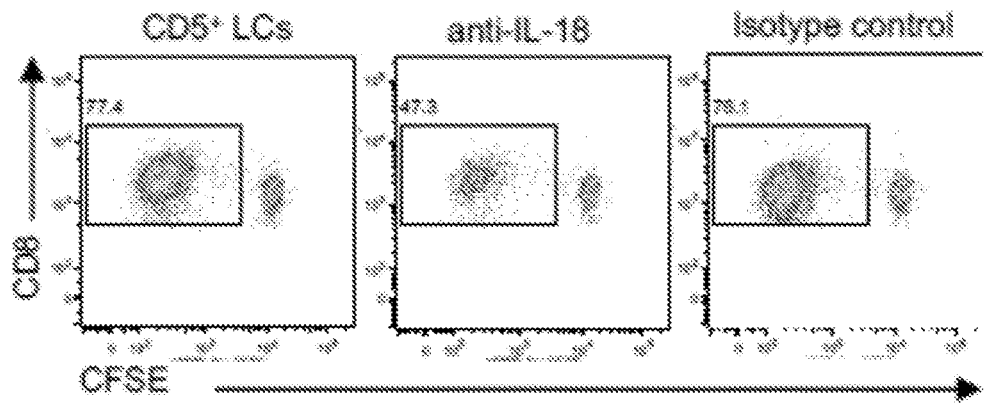
Figure 14D:
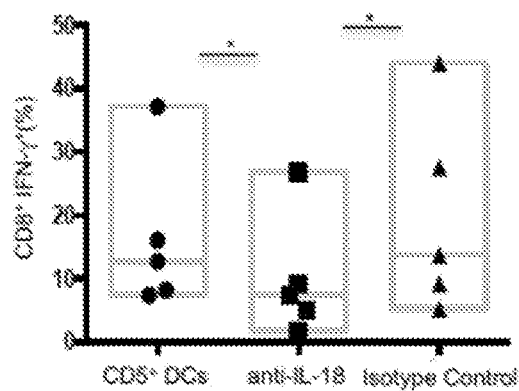
Figure 15:
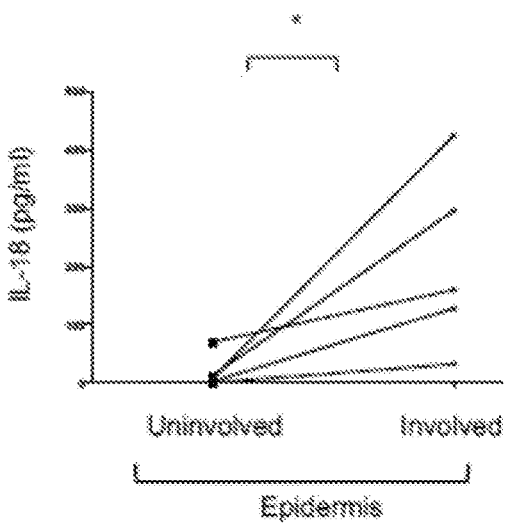
FIG. 15 is a plot showing IL-18 is highly expressed in involved lesions of psoriasis that contains high numbers of CD5$^+$ DCs. IL-18 was measured by luminex in the supernatant of involved and uninvolved skin of psoriasis patients.

To understand the mechanism by which $CD5^+$ DCs polarize specialized T cell responses, the cytokine expression patterns of $CD5^+$ and $CD5^-$ DCs that were sorted from the epidermal or dermal leukocytes were analyzed by quantitative real time PCR (qPCR). As shown in FIG. 14A, $CD5^+$ LCs as well as $CD5^+$ dermal DCs expressed approximately three-fold higher levels of IL-18, compared to their $CD5^-$ counterparts. Immunofluorescence staining of activated skin DCs validated the expression of IL-18 protein by the $CD5^+$ DCs in both epidermis and dermis (FIG. 14B). To establish a role for IL-18 in $CD5^+$ DC-dependent T cell activation, co-cultures of DC subsets and allogeneic naive T cells were supplemented with either a neutralizing anti-IL-18 mAb or an isotype-matched control. Addition of neutralizing anti-IL-18 inhibited the proliferation of $CD8^+$ T cells primed with $CD5^+$ DCs by approximately 40% (FIG. 14C). The $CD8^+$ T cells that were primed in the presence of anti-IL-18 expressed lower levels of IFN-γ compared to those of control cultures (FIG. 14D). Taken together, these data indicate that $CD5^+$ DCs potentiate effector $CD8^+$ T cell responses through the production of IL-18.

DC/T Cell Co-Cultures

Naive T cells were isolated using Pan Naïve T cell isolation kit (Miltenyi Biotec) according to the manufacturer protocol or sorted as $CCR7^+CD45RA^+CD8^+$ or $CCR7^+CD45RA^+CD4^+$ cells. T cells were then CFSE-labeled and cultured with sorted skin DCs for seven to ten days. Proliferation was assessed by the percentage of CFSE-labeling dilution. IL-22, IFN-γ and Granzyme B production were assessed by flow cytometry after a short restimulation with PMA (Sigma; 25 ng/ml) and Ionomycin (Sigma; 1 μM). Alternatively, proliferated cells were stimulated overnight with anti-CD3 and anti-CD28 mAbs (DYNAL beads 2 μl per $3 \times 10^5$ cells) and cytokines produced by the cells were assessed in the supernatant using a Luminex magnetic bead assay. Where indicated blocking IL-18 mAb (5 μg/ml, 125-2H; MLB) or an isotype-matched control were added to the co-culture at equal concentration.

Methods

Immunofluorescence Analysis of CD5 and IL-18 Expression

Healthy skin and formalin fixed psoriasis biopsy specimens from plaque (involved) and adjacent skin (uninvolved) were embedded in O.C.T for immunofluorescence staining. Tissue sections were cut into 10-μm sections using the Leica CM 1950. Sections were fixed in 4% PFA for 15 minutes at room temperature and washed with PBS containing 3%

Bovine serum albumin (BSA) and 10% saponin, they were quenched with 0.5M Glycine for five minutes, washed, and blocked with PBS/BSA/Saponin for 30 minutes at room temperature. Sections were stained overnight with polyclonal rabbit anti-human IL-18 (1 μg/ml, polyclonal; MBL) and monoclonal mouse anti-human CD5 (5 μg/ml; UCHT2, eBioscience) or isotype controls, washed and incubated with antimouse Cy3 (3 μg/ml, Jackson Immunoresearch) and donkey anti-rabbit Alexa Fluor 647 (0.6 μg/ml, Jackson ImmunoResearch) for two hours, followed by 4',6'-diamidino-2-phenylindole (DAPI) for 20 minutes at room temperature. Intracellular IL-18 expression was assessed in epidermal and dermal cell suspension. Cells were activated overnight with IL-15 and IFN-α in the presence of monensin in a similar manner to that described above. Stained cells or tissue sections were mounted (ProLong mounting medium, Invitrogen). Images were acquired using an Olympus Confocal Microscope FV1000 using Fluoview software. Image analysis was performed using ImageJ software.

Quantitative Real Time PCR (qPCR)

mRNA expression of IL-18 was assessed by qPCR. In brief, reverse transcription of 350 ng of RNA was performed to obtain cDNA using oligo(dT) primers and Superscript III transcriptase (Life Technology). qPCR measurement was assessed using SYBR Green Fast Master Mix (Roche Diagnostics) and an AB17900 Fast Real-Time PCR System (Life Technologies). The primers used are recited in SEQ ID NO 23-28. The results of IL-18 expression were normalized to the housekeeping genes: β-actin (ACTB) and GAPDH. The following primers were used:

IL-18 F-GCCTAGAGGTATGGCTGTAACTATCTCTG (SEQ ID NO: 23); IL-18 R-CATGTCCTGGGACACTTCTCTGAAAG (SEQ ID NO: 24); β-actin (ACTB) F-AGGCACCAGGGCGTGAT (SEQ ID NO: 25); β-actin (ACTB) R-GCCCACATAGGAATCCTTCTGAC (SEQ ID NO: 26); GAPDH F-ATGGTGAAGGTCGGTGTG (SEQ ID NO: 27); or GAPDH R-CATTCTCGGCCTTGACTG (SEQ ID NO: 28). The results were normalized to the housekeeping genes: β-actin (ACTB), GAPDH and 18S. Results are expressed as the median of fold change=2-ΔΔCt, where $\Delta\Delta Ct = (Ct_{Target} - Ct_{house\ keeping\ gene})_{assay} - (Ct_{Target} - Ct_{house\ keeping\ gene})_{control}$, as described previously.

Discussion

Our analysis of cytokine expression revealed that the $CD5^+$ subsets in the epidermis and dermis express higher amounts of IL-18 compared to their CD5− counterparts, which contributes to their ability to prime greater CTL responses. We have previously established that LCs and dermal CD1a(dim) DCs express IL-15 (Banchereau et al., 2012a), which is important for their ability to prime CTL responses, thus it is conceivable that IL-18 will synergize with IL-15 in this process. Interestingly, IL-18 expressed at higher levels by LCs compared to dermal DCs. Consistent with the increased numbers of $CD5^+$ DCs, we also found elevated amounts of IL-18 in the epidermis of psoriatic plaques. Therefore, the attenuation of IL-18 produced by this DC subtype can be evaluated as a novel therapy. Interestingly, IL-18 was not detected in the dermis of psoriasis plaques, however, this could be due to a significantly low numbers of cells recovered from the dermis compared to the epidermis and which was below our detection limit. In addition, we showed that the $CD5^+$ DCs are able to prime Th22 cells that express IL-22 independently of IL-17. We could not find any role for IL-18 in this process, thus at present, the precise mechanism for how Th22 cells are primed by the $CD5^+$ DCs is unclear. Potential differences in the expression of other proteins between the $CD5^+$ and $CD5^-$ DCs may well relate to differences in their ability to stimulate IL-22 production in T cells.

Example 5: CD5+ DCs Responsible for Priming Polycytotoxic CD8+ T Cells

This example describes an experiment showing that the CD5+ DCs are also the only cell that could prime polycytotoxic CD8+ T cells (cells expressing granzyme perforin and granulysin) (see e.g., FIG. 16) that are critical for fighting mycobacteria infections.

What is claimed is:

1. A method of modulating CD5 in a cell of a subject comprising:
   (A) modulating CD5 in the cell of a subject, wherein the cell is a progenitor cell, a dendritic cell (DC), or a langerhans cell (LC), wherein
      (i) modulating CD5 comprises administering a CD5 inhibiting agent comprising IL-4 in an amount effective to reduce CD5 expression or CD5+ cell quantity; the subject has psoriasis; and reducing CD5 expression or CD5+ cell quantity reduces pathogenesis of psoriasis by reducing TH1 and TH22 and CTL responses.

2. The method of claim 1, wherein administering the CD5 agent comprising IL4 blocks monocyte call differentiation.

3. A method of differentiating progenitor cells into CD5+ dendritic cells comprising:
   obtaining or having obtained a progenitor cell from a subject; or isolating or having isolated a progenitor cell from a biological sample from the subject; and
   activating CD5 on a progenitor cell, wherein activating CD5 induces differentiation of the progenitor cell, wherein
   (A) CD5 s activated with:
      (i) FLT3-L and SCF;
      (ii) FLT3-L, GM-CSF, and SCF;
      (iii) TNF-α, FLT3-L, GM-CSF, and SCF;
      (iv) LTα/β, FLT3-L, GM-CSF, and SCF;
      (v) TNF-α and LTα/β; and
   (B) the progenitor cell comprises CD34-CD123(hi)CD117(dim) and the progenitor cells are differentiated into CD11c+CD1c+CD5+ DCs.

4. The method of claim 3, wherein the biological sample comprises a blood sample, a biopsy sample, or a tumor sample.

5. The method of claim 3, further comprising administering the activated progenitor cell to the subject, a target, or a tumor site, wherein CTL response is enhanced.

6. The method of claim 1, wherein the cell is not a B cell.

7. The method of claim 3, wherein the cell is not a B cell.

* * * * *